US008414542B2

(12) United States Patent
Stroup

(10) Patent No.: US 8,414,542 B2
(45) Date of Patent: *Apr. 9, 2013

(54) DEVICES, ASSEMBLIES, AND METHODS FOR CONTROLLING FLUID FLOW

(75) Inventor: David K. Stroup, El Cajon, CA (US)

(73) Assignee: Infusion Innovations, Inc., La Jolla, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/920,807

(22) PCT Filed: Mar. 4, 2009

(86) PCT No.: PCT/US2009/036088
§ 371 (c)(1),
(2), (4) Date: Sep. 2, 2010

(87) PCT Pub. No.: WO2009/111596
PCT Pub. Date: Sep. 11, 2009

(65) Prior Publication Data
US 2011/0015580 A1 Jan. 20, 2011

Related U.S. Application Data

(60) Provisional application No. 61/033,702, filed on Mar. 4, 2008.

(51) Int. Cl.
*A61M 5/00* (2006.01)
*F16L 37/28* (2006.01)
(52) U.S. Cl. ............. 604/246; 604/249; 251/149.5
(58) Field of Classification Search .......... 604/533–537, 604/236–238, 246–250
See application file for complete search history.

(56) References Cited

U.S. PATENT DOCUMENTS 3,931,992 A 1/1976 Coel
4,694,856 A 9/1987 Leibinsohn
(Continued)

FOREIGN PATENT DOCUMENTS
WO 2009052433 4/2009
WO 2009111596 9/2009

OTHER PUBLICATIONS

International Search Report and Written Opinion for PCT/US2009/036088 dated Sep. 30, 2009.

(Continued)

*Primary Examiner* — Kevin C Sirmons
*Assistant Examiner* — Andrew Gilbert
(74) *Attorney, Agent, or Firm* — Stephen C. Beuerle; Procopio Cory Hargreaves & Savitch LLP

(57) ABSTRACT

Connector assemblies are provided for controlling flow in a fluid line that include an outer shell, an inner housing, and a tubular member. The inner housing is disposed within the outer shell and includes a boss disposed adjacent a first end of the outer shell. The inner housing is movable axially within the outer shell between first and second positions when a device is connected to the first end. The tubular member is carried by the inner housing and includes a fluid passage extending between a second end of the outer shell. The tubular member moves axially as the inner housing moves between the first and second positions, and cam features on the outer shell and the tubular member cause the tubular member to rotate as the inner housing moves between first and second positions, thereby opening a fluid path between the fluid passage and the first end.

15 Claims, 71 Drawing Sheets

U.S. PATENT DOCUMENTS

| | | | |
|---|---|---|---|
| 5,255,734 A | 10/1993 | Leonard et al. | |
| 5,755,269 A | 5/1998 | Venooker et al. | |
| 5,989,223 A * | 11/1999 | Chu et al. | 604/167.05 |
| 6,892,998 B2 * | 5/2005 | Newton | 251/149.1 |
| 7,140,592 B2 * | 11/2006 | Phillips | 251/149.6 |
| 7,559,530 B2 * | 7/2009 | Korogi et al. | 251/149.6 |
| 7,645,274 B2 * | 1/2010 | Whitley | 604/537 |
| 7,815,614 B2 * | 10/2010 | Fangrow, Jr. | 604/256 |
| 7,976,532 B2 * | 7/2011 | Kitani et al. | 604/533 |
| 8,066,692 B2 * | 11/2011 | Simpson et al. | 604/537 |
| 8,251,346 B2 * | 8/2012 | Stroup | 251/149.5 |
| 2003/0066978 A1 * | 4/2003 | Enerson | 251/86 |
| 2003/0199835 A1 | 10/2003 | Leising | |
| 2004/0172006 A1 * | 9/2004 | Bonaldo | 604/523 |
| 2007/0088293 A1 * | 4/2007 | Fangrow, Jr. | 604/246 |
| 2007/0255229 A1 * | 11/2007 | Kane et al. | 604/248 |

OTHER PUBLICATIONS

International Search Report and Written Opinion for PCT/US2011/040583 dated Feb. 23, 2012, 10 pages.

International Search Report and Written Opinion for PCT/US2009/36088 dated Mar. 4, 2009.

* cited by examiner

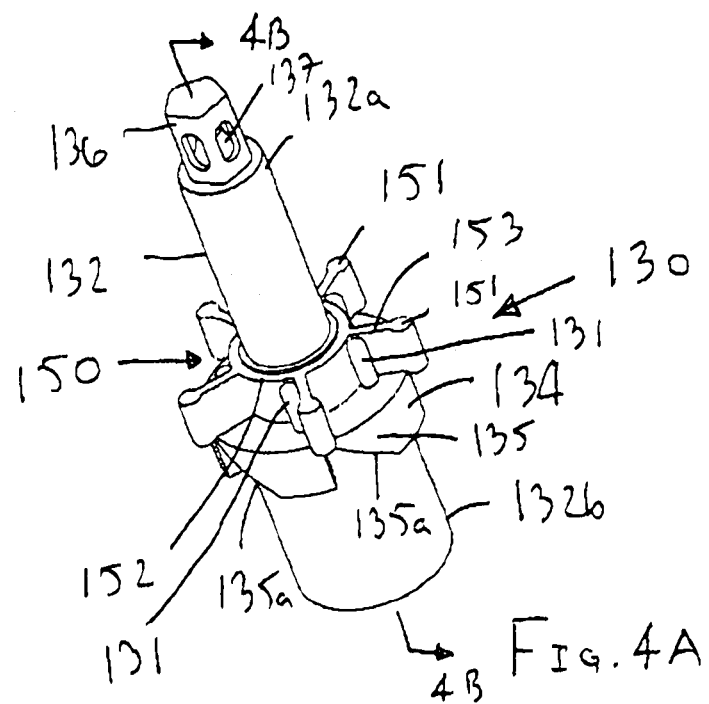
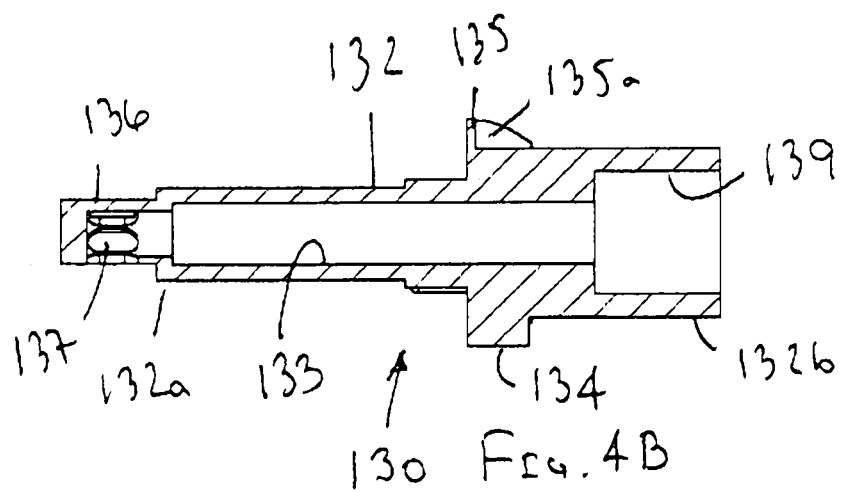
Fig. 4A
Fig. 4B

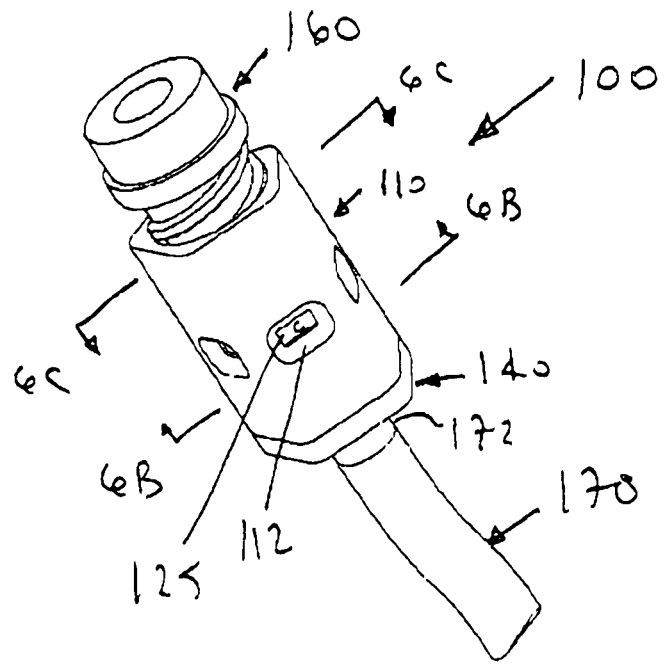
FIG. 6A(1)
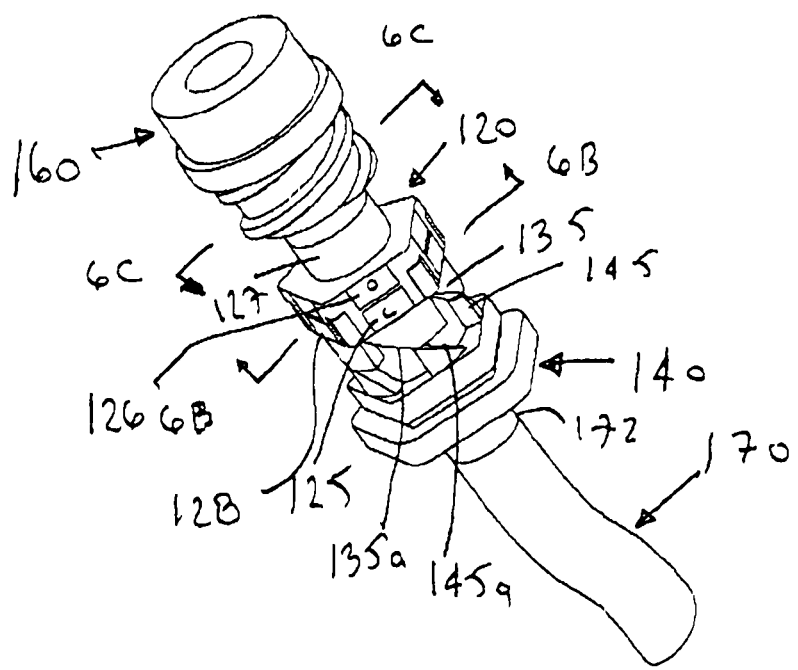
FIG. 6A(2)

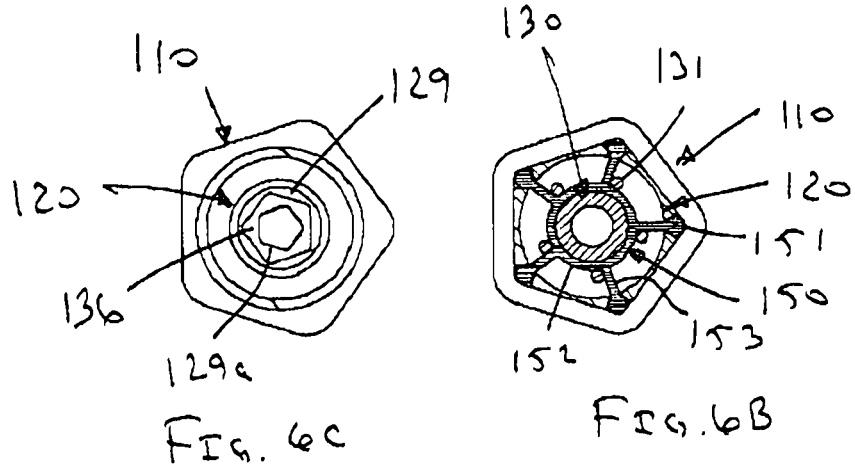

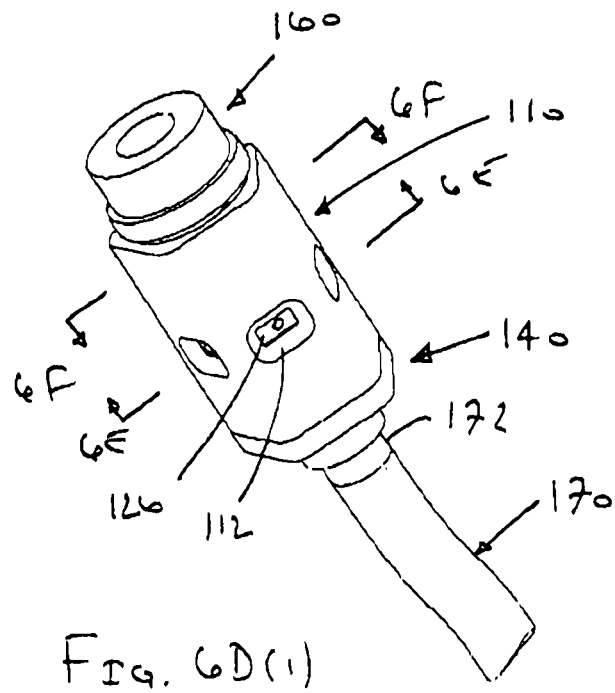
FIG. 6D(1)
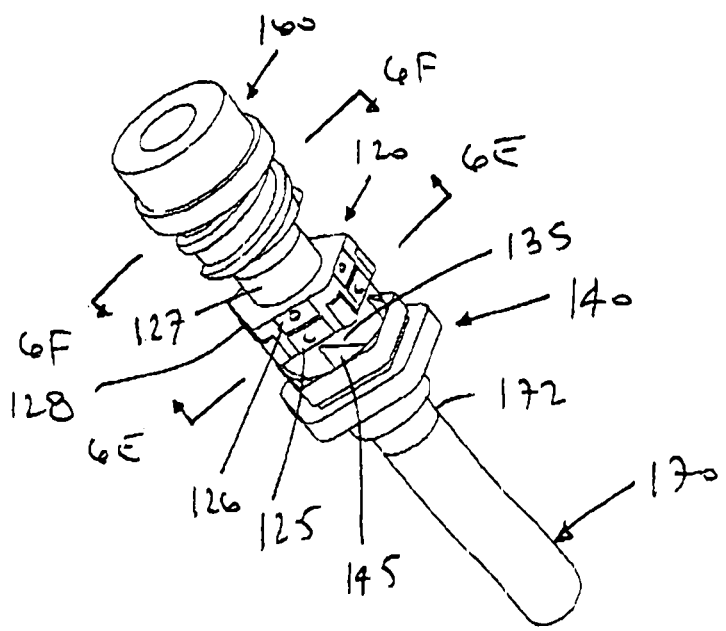
FIG. 6D(2)

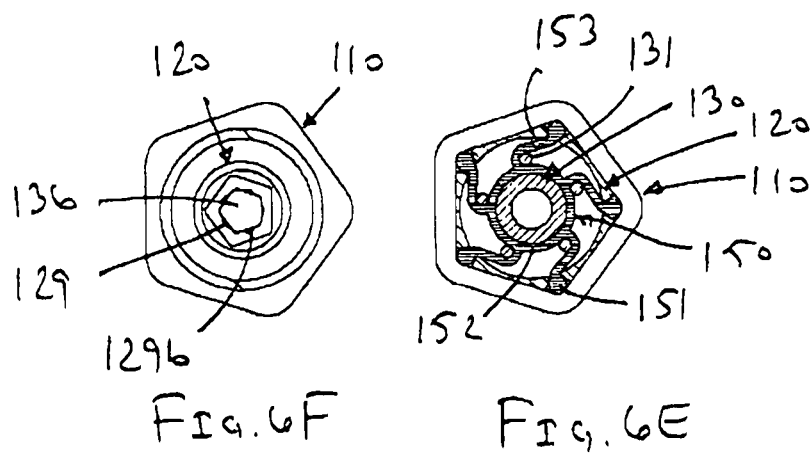

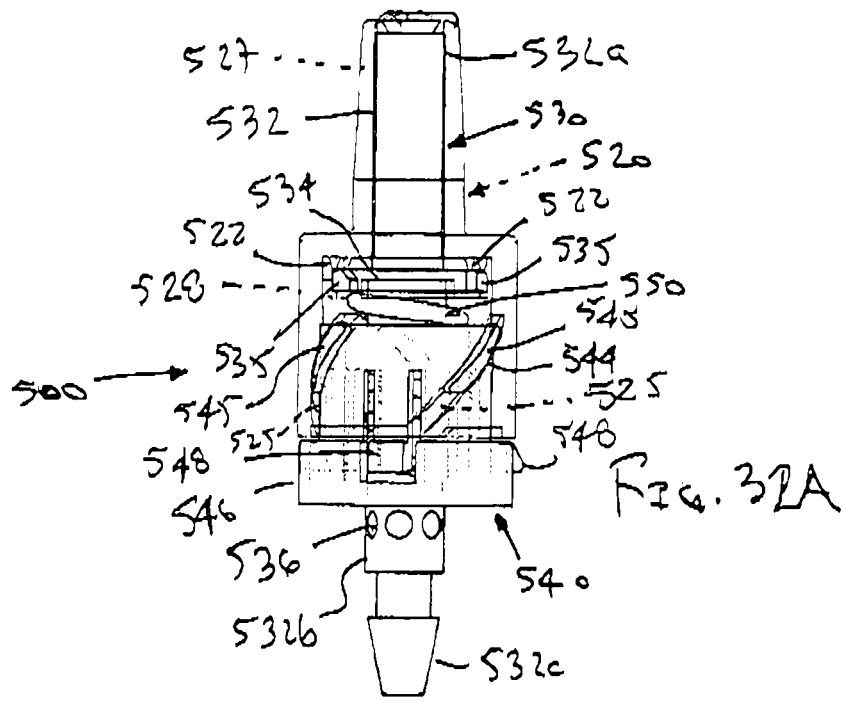
FIG. 32A
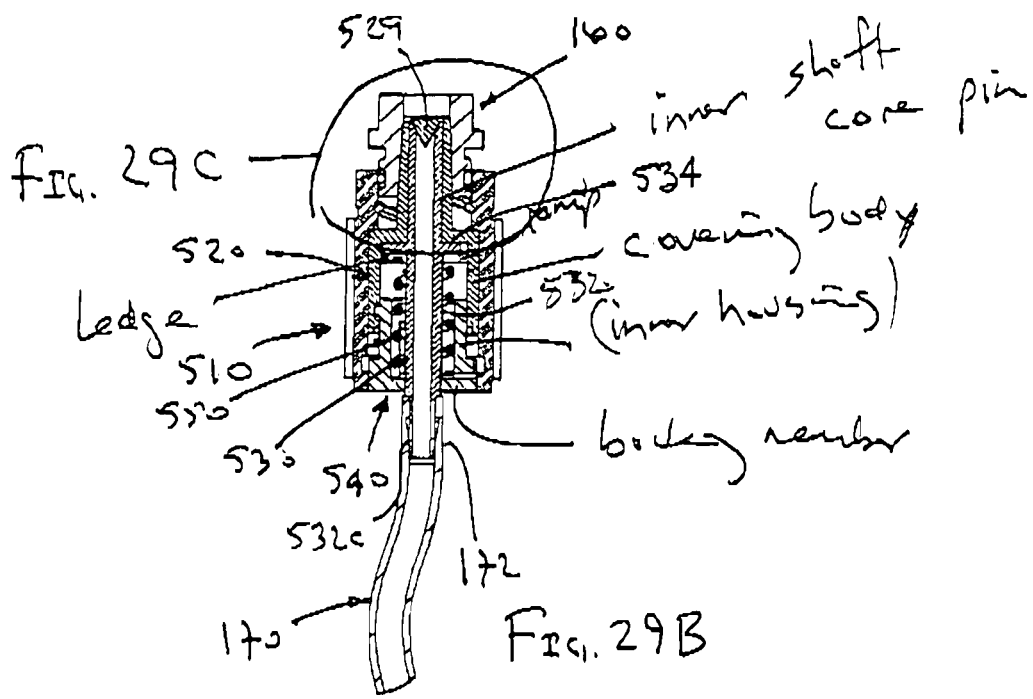
FIG. 29C
FIG. 29B

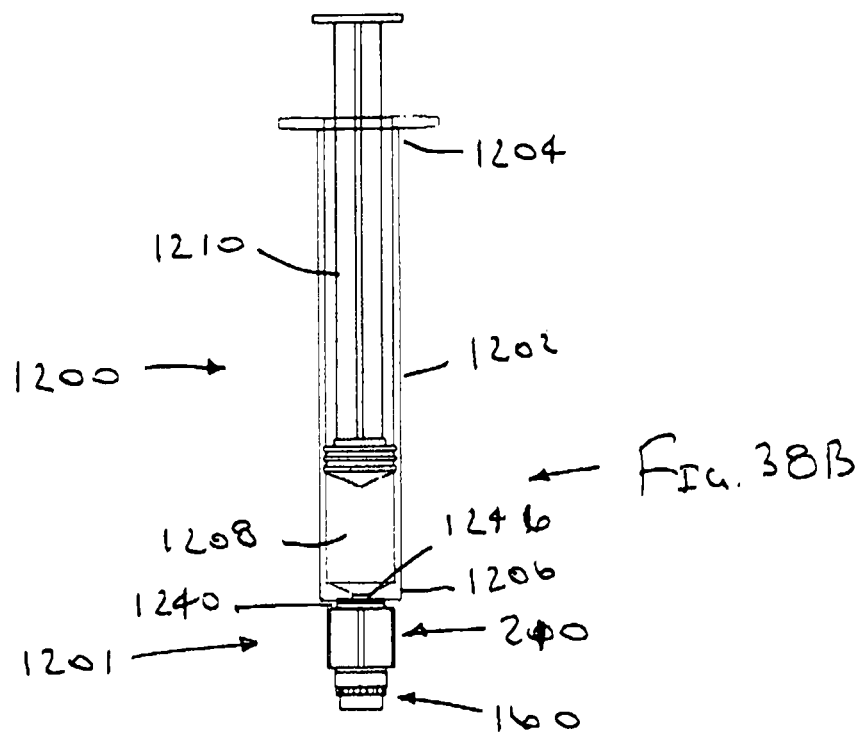
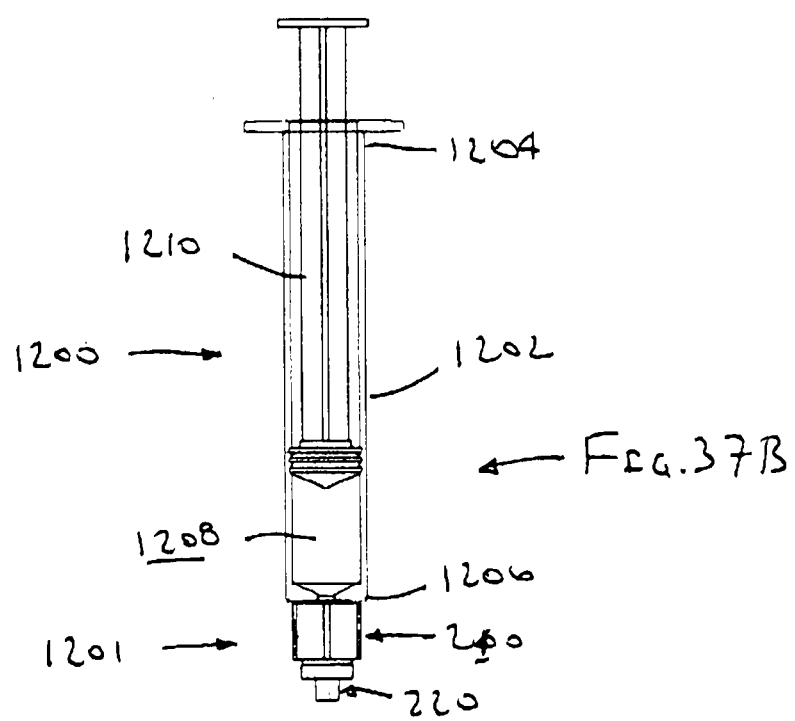

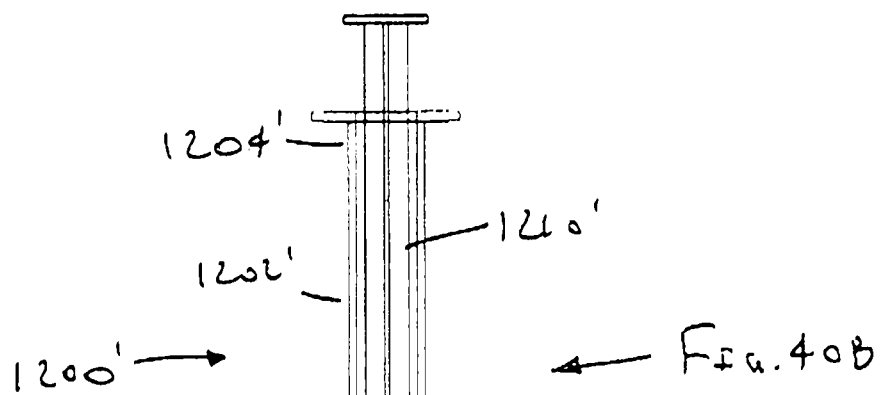
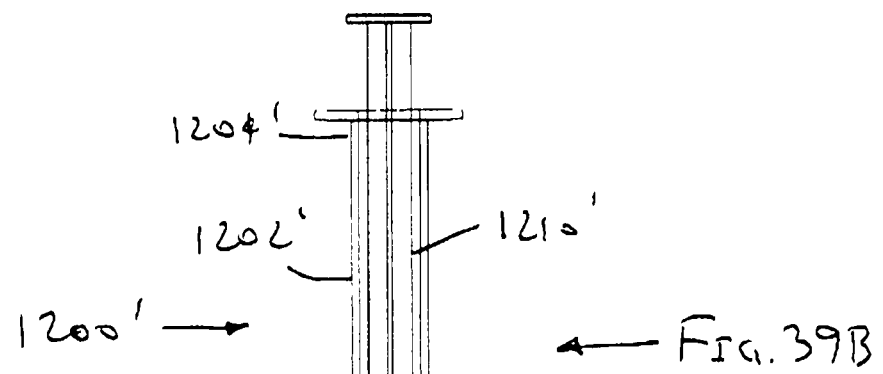
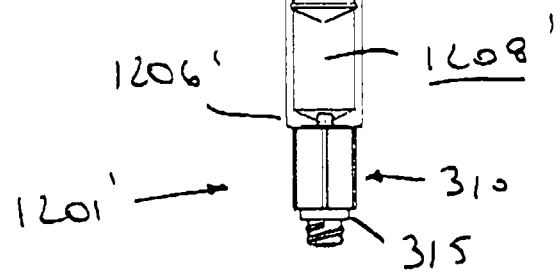

DEVICES, ASSEMBLIES, AND METHODS FOR CONTROLLING FLUID FLOW

FIELD OF THE INVENTION

The present invention relates generally to apparatus and methods for controlling flow. More particularly, the present invention relates to devices, assemblies, and/or methods for controlling fluid flow, e.g., to connectors and/or valves for controlling flow through an IV or other fluid line into a patient, a syringe, container, and/or other medical device, and/or to systems including such connectors and/or valves.

BACKGROUND

Controlling flow is an important and useful tool in virtually all scientific fields. One such field where controlling flow is highly useful is in the medical arena. For example, it may be useful to control flow during infusion, e.g., when introducing fluid into a blood vessel, such as a vein, via a fluid line for therapeutic and/or diagnostic purposes. The fluid introduced may be saline solution, plasma solution, glucose solution, antibiotics, pain relievers, nuclear medicine agents, and the like. Infusion may involve many fluid doses into a patient over long periods of time. Early in the infusion field, each fluid dose required a new needle to be inserted into the vein. Repeated insertion of a needle into the same vein of a patient, however, may damage the vein, increase the potential for bruising, and/or inflict pain on or discomfort to the patient.

Health professionals quickly changed this routine by inserting one needle into the patient's vein, and leaving it there for initial and subsequent fluid dose introductions. This stationary needle could be connected to a first or proximal end of a catheter that had an opening at a second or distal end for receiving fluid from a syringe or other device. For example, a latex cap was placed over the distal end of the catheter, which could be penetrated by a beveled hollow needle. Once inserted into the patient's vein, the stationary needle could be secured with tape, but was prone to disconnection from the patient. From this basic concept, a range of needleless connectors were developed capable of linking the fluid line to the patient's catheter directly thereby bypassing needle use. Further industry directive and federal regulation encouraged this alternative technique of promoting needleless connectors' use, thereby promoting removal of sharp instruments from the patient area.

Early needleless connectors featured a split septum on the female end (e.g., the end closer to the patient during connection). The split septum could be opened by inserting a cannula. The male end featured a blunt cannula, which was inserted into the split-septum on the female end. This method relieved some of the disconnection problems, but a new problem emerged. Removing the blunt cannula created a negative pressure inside the catheter, which caused a small amount of blood from the patient to flow into the proximal end of the catheter. These small amounts of blood would accumulate in the catheter, thereby clogging the fluid pathway. The consequence of this negative pressure, or negative bolus effect, was to require a new, clean catheter. The replacement of these clogged catheters may be expensive and/or painful to the patient.

The split septum on the female end was then replaced with an anti-reflux valve activated by the use of a male-female Luer configuration, also termed sequential valving. This male-female Luer connection has been standardized by the industry, e.g., through international standard ISO 594-2 "Conical fittings with a 6% (Luer) taper for syringes, needles and certain other medical equipment", Part 2: Lock fittings.

The demand for closed needleless systems for fluid administration is driven, at least partially, by the safety concerns associated with medications that are toxic to healthcare workers that prepare and administer these medications. These medications include chemotherapy and radiotherapeutic agents. Key industry organizations, such as the National Institute for Occupational Safety and Health (NIOSH), Oncology Nursing Society (ONS), and American Society of Health System Pharmacists (ASHP), recommend adopting closed systems to minimize drips, leaks, or spills of the drug to help eliminate surface contamination and exposure.

The vast majority of the self-sealing medical connectors that are used for the administration of parenteral fluids are designed with an unsealed male Luer connector on the end that remains connected to the patient's IV line, fluid source, etc., and a female connector on the opposite free end of the connector through which a syringe or other types of devices is connected. In many devices on the market, there is a self sealing valve built into the female connector. The male Luer typically does not have an internal valve, and as such, any remaining fluid is capable of being exposed to care providers and/or patients upon disconnection of the unsealed male Luer. As mentioned above, for certain applications, the fact that residual volume of the fluid may be unsealed and/or exposed to individuals around the IV system may pose significant health hazards. Additionally, these conventional Luer connectors may have a larger internal volume in which fluid may collect, and also employ many parts thereby increasing the potential for error in manufacturing or during use.

The standard connection mechanism for these Luer connectors involves aligning the threads together by a helical threading action. This threading action is meant to establish a connection between (e.g., engage) the two Luer ends, and is not the force used to open or close (e.g., actuate) fluid pathways. As the two Luer connectors are being connected together, there is a separate translational (e.g., on a vertical axis) action within these connection assemblies that acts to engage the fluid pathways. Traditionally, the female end has a thread on the outside while the male has a thread on the inside. Since most female ends have self-sealing valves, the user may open the fluid path with the translational force during engagement or after the male end is completely engaged and locked inside the female end. Thus, the user may not know at what point the fluid path is sufficiently opened or closed during connection and disconnection of the two connectors. The user only knows that the fluid path is closed (e.g., the two connectors are deactuated), when the two connectors are completely disengaged, or disconnected, and separated.

Thus, there is a need in the art for a connector and/or connecting assembly that may effectively avoid uncertainty in the actuation process, avoid certain undesired pressure effects, create certain desired pressure effects, reduce the internal volume of the assemblies, and/or decrease the number of members required for manufacturing.

SUMMARY OF THE INVENTION

The present invention is directed to apparatus and methods for controlling flow through a fluid line or device, for example, to connectors and/or valves for delivering fluid via an intravenous ("IV") or other medical fluid line into a patient, a syringe, container, and/or other medical device, and to systems including such connectors and/or valves.

Conventional devices and assemblies for establishing medical connections are not completely effective and are potentially unsafe. For example, conventional medical connectors may expose the user to harmful agents during disconnection as a result of undesired bolus effects, may collect undesired fluid within their internal volumes after disconnection, may not notify the user of the actuation status during connection and disconnection, and/or may include many parts thereby making manufacture expensive. In contrast, embodiments herein may use fewer parts, may minimize and/or eliminate residual fluid within the connectors after disconnection, may utilize a rotational actuation force as opposed to translation force to avoid or create a desired bolus effect, and/or may incorporate actuation status indicators to notify the user when actuation is complete.

In exemplary embodiments, medical connectors disclosed herein may be used for the administration of parenteral fluids, such as needleless connectors that may offer alternative mechanisms to conventional Luer connectors, may utilize a visual indicator that provides instant feedback to an operator regarding actuation status, and/or may employ alternative ways for energy storage, including rotational force, electromagnetic, polymer torsion spring, and/or spring washers for actuation.

As used herein, "proximal" refers to a first end of the device, e.g., the portion of the device or component that is closer to the patient when the device or component is properly positioned, for example, on a patient's IV line. "Distal" refers to a second opposite end of the device, e.g., the portion of the device or component that is farther from the patient when the device or component is properly positioned, for example, on a patient's IV line. For reference, the female end may be upstream in an IV flow circuit and the male may be downstream or vice versa. "Actuated" refers to the condition in which the fluid path is opened to allow fluid to transfer freely along the fluid path, while "deactuated" refers to the condition in which the fluid path is closed and fluid transfer is not permitted. "Engaged" refers to the condition in which two members that are designed for connection, for example, Luer connectors, are physically connected to each other in a manner in which they are designed to be connected, while "disengaged" refers to the condition in which two members, for example, Luer connectors, are physically disconnected from one another. When two members are referred to as "engaged," they may or may not be "actuated." The two members are "actuated" only when they are fully engaged, and fluid transfer is permitted between them. Alternatively, one member may use one valve component (male or female) and a passive (non-valved) element of opposite gender. "Female" Luer connector refers to a connecting member that includes a Luer thread on its outer surface. "Male" Luer connector refers to a connecting member that includes a Luer thread on its inner surface. "Passive" refers to the conditions under which a connector or assembly functions, and signifies that the assembly is capable of deactuating automatically as it is disengaged. "Non-Passive" refers to the conditions under which a connector or assembly functions, and signifies that the assembly does not automatically deactuate as it is disengaged, but requires a separate action. Optionally, in the embodiments herein, there may be sequential valving, resulting in co-dependent or independent actuation of male and/or female sides of valves.

In accordance with an exemplary embodiment, a connector assembly is provided for controlling flow in a fluid line. The connector assembly may include an outer shell, an inner housing, and a tubular member. The outer shell may include a first end, a second end, and a passage extending therebetween. The inner housing is disposed within the outer shell and may include a boss disposed adjacent the first end. The inner housing may be movable axially within the outer shell between a first position adjacent the first end and a second position further from the first end than the first position when a device is connected to the first end of the outer shell.

The tubular member may be disposed within the inner housing and may include a fluid passage therein extending between the second end of the outer shell and the boss of the inner housing. The tubular member may be carried by the inner housing such that the tubular member moves axially as the inner housing moves between the first and second positions. The connector assembly may also include cam features on the outer shell and/or the tubular member for causing the tubular member to rotate as the inner housing moves between the first and second positions, thereby opening a fluid path between the fluid passage in the tubular member and the first end of the outer shell.

For example, when a device is connected to the first end of the outer shell, the tubular member may rotate relative to the inner housing to allow fluid flow through the assembly with the device connected to the first end of the outer shell. Optionally, the inner housing may be biased to the first position, e.g., to bias the tubular member to close the fluid path.

In accordance with another embodiment, a connector and/or valve assembly is provided for controlling flow in a fluid line that includes an outer shell including a first end, a second end, and a passage extending therebetween, the first end including a connector for connecting the assembly to a fluid line; an inner housing disposed within the outer shell and including a boss disposed adjacent the first end, the inner housing being movable axially within the outer shell between a first position adjacent the first end and a second position further from the first end than the first position when a device is connected to the connector on the first end of the outer shell; a tubular member disposed within the inner housing and including a fluid passage therein extending between the second end of the outer shell and the boss of the inner housing, the tubular member carried by the inner housing such that the tubular member moves axially as the inner housing moves between the first and second positions; and cam features on the inner housing and the tubular member for causing the tubular member to rotate as the inner housing moves between the first and second positions, thereby opening a fluid path between the fluid passage in the tubular member and the first end of the outer shell to allow fluid flow through the assembly with the device connected to the first end of the outer shell.

In accordance with another embodiment, a connector assembly for controlling flow in a fluid line is provided that includes an outer shell or bezel including a first end, a second end, and a passage extending therebetween, the first end including a connector for connecting the assembly to a fluid line. An inner housing may be disposed within the outer shell that includes a boss disposed adjacent the first end, the inner housing being movable axially within the outer shell between a first position adjacent the first end and a second position further from the first end than the first position when a device is connected to the connector on the first end of the outer shell. A backing member may be coupled to the second end of the outer shell such that the outer shell is substantially axially fixed relative to the backing member and rotatable relative to the backing member, the backing member slidably coupled to the inner housing such that the inner housing moves helically relative to the backing member when the inner housing is directed from the first position towards the second position. A tubular member may include a first end disposed within the inner housing and a second end extending through the backing member, the tubular member slidably coupled to the backing member such that the tubular member substantially rotationally fixed relative to the backing member and is movable axially relative to the backing member, the tubular member comprising a fluid passage therein extending between the first and second ends. A seal on the boss may engage the first end of the tubular member in the first position to substantially seal the fluid passage, and cam features may be provided on the inner housing and the tubular member for coupling axial movement of the tubular member to axial movement of the inner housing when the inner housing is initially moved from the first position towards the second position, the cam features causing the tubular member to move distally relative to the inner housing immediately before the inner housing reaches the second position, thereby disengaging the seal from the first end of the tubular member and opening the fluid passage.

In accordance with still another embodiment, a dual valve assembly is provided that includes first and second valves coupled to a common backing member and/or sharing a common fluid path. The fluid path may remain substantially closed until both valves are opened, e.g., when a complementary Luer fitting or other connector is coupled to respective ends of the first and second valves. Each valve may include an outer housing or bezel, an inner housing or covering body, a tubular member, a camming member, and a spring or other elastic member. For example, the elastic member may bias the tubular member to a closed position within the respective bezel, while the camming member may cooperate to open the respective valve, e.g., during connection of a Luer fitting to the bezel. The valves may be configured to provide a positive, negative, or substantially zero pressure differential within the assembly and/or within the adjacent fluid line during actuation and/or deactuation of the valves of the assembly.

Methods for using such connector and/or valve assemblies are also provided.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which:

FIG. 4A is a perspective view of an exemplary embodiment of the shaft of the connecting assembly of FIG. 1B that includes a conduit, a fluid post with openings, and a mating member with pegs on its proximal side and cam features on its distal side.

FIG. 4B is a cross-section of the shaft of FIG. 4A taken along line 4B-4B.

FIGS. 6A(1) and 6A(2) are perspective views of the connecting assembly of FIGS. 1A and 1B in a deactuated condition, with the outer shell included and removed, respectively, showing a Luer connector mating with the outer shell; the covering body with status indicators that indicate the deactuated condition; the cam features of the shaft; and the backing member with its cam elements spaced apart from the cam features.

FIG. 6B is a cross-sectional view of the deactuated connecting assembly shown in FIGS. 6A(1) and 6A(2), taken along line 6B-6B.

FIG. 6C is a cross-sectional view of the deactuated assembly shown in FIGS. 6A(1) and 6A(2), taken along line 6C-6C.

FIGS. 6D(1) and 6D(2) are perspective views of the connecting assembly of FIGS. 1A and 1B in an actuated condition, with the outer shell included and removed, respectively, showing the Luer connector; the covering body status indicators that indicate the actuated condition; the cam elements on the shaft engaging with the cam elements on the backing member.

FIG. 6E is a cross-sectional view of the actuated connecting assembly shown in FIGS. 6D(1) and 6D(2), taken along line 6E-6E.

FIG. 6F is a cross-sectional view of the actuated assembly shown in FIGS. 6D(1) and 6D(2), taken along line 6F-6F.

FIGS. 29B and 29C are cross-sectional views of the assembly of FIG. 29A, taken along lines 29B-29B.

FIGS. 32A and 32B are side and perspective views, respectively, of the assembly of FIG. 30A with the outer shell removed to show the position of the internal components of the assembly after actuation.

FIGS. 37A and 37B are perspective and side views, respectively, of an exemplary embodiment of a syringe including an integral valve in a deactuated condition.

FIGS. 38A and 38B are perspective and side views, respectively, of the syringe of FIGS. 37A and 37B with the valve in an actuated condition after being connected to a female Luer fitting.

FIGS. 39A and 39B are perspective and side views, respectively, of another exemplary embodiment of a syringe including an integral valve in a deactuated condition.

FIGS. 40A and 40B are perspective and side views, respectively, of the syringe of FIGS. 39A and 39B with the valve in an actuated condition after being connected to a male Luer fitting.

FIG. 45C is an exploded view of the assembly of FIG. 45A, including an outer shell with a proximal throughbore containing a Luer thread and a distal throughbore; a covering body including a male boss with openings and an outer mating surface; and an elastic member between a camming element and a backing member.

DETAILED DESCRIPTION OF THE EXEMPLARY EMBODIMENTS

Apparatus and methods described herein may relate to connecting devices and assemblies that, among other things: utilize a rotational force for actuation to avoid or create a desired bolus effect, minimize the number of parts necessary for manufacture, decrease the internal volume of the devices and assemblies, and/or use status indicators to signify when actuation and deactuation are complete. Also, in some embodiments, the apparatus described herein may create and maintain a flat (planar) surface that is easily swabbed for cleaning and sterilization purposes. Although embodiments of connecting devices and assemblies are described herein with respect to medical connections, such connecting devices and assemblies are not limited to medical connections alone but may be applicable to any connection device or assembly that could benefit from the use of a rotational actuation force, status indicators, and/or any of the other features described herein.

For the following description, it should be noted that correspondingly labeled structures across the figures (e.g., 132 and 232, etc.) may possess the same general characteristics and/or may be subject to the same basic structure and function.

Figure 1A:
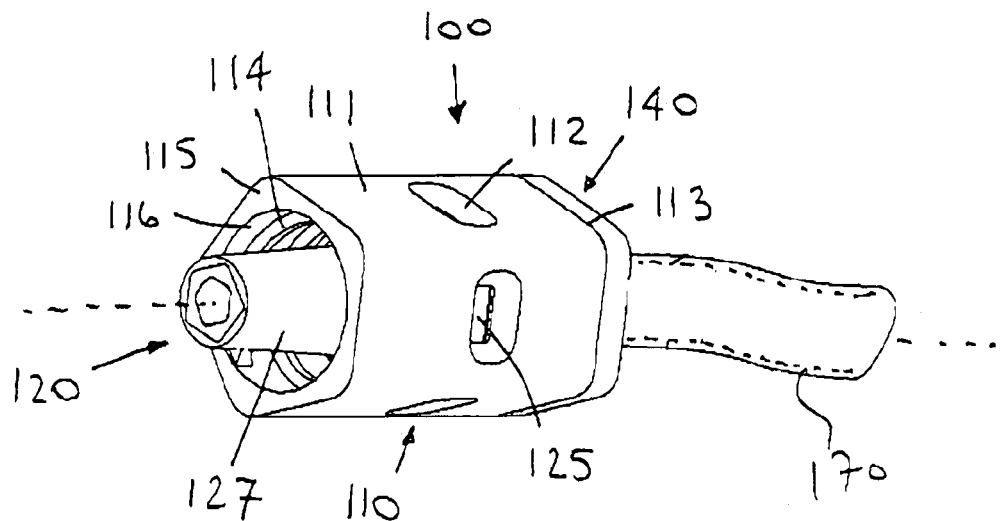
FIG. 1A is a perspective view of an exemplary embodiment of a passive connecting valve assembly including an outer shell or bezel with a Luer thread and status windows, and a section of tubing extending from a distal end of the outer shell.
Figure 1B:
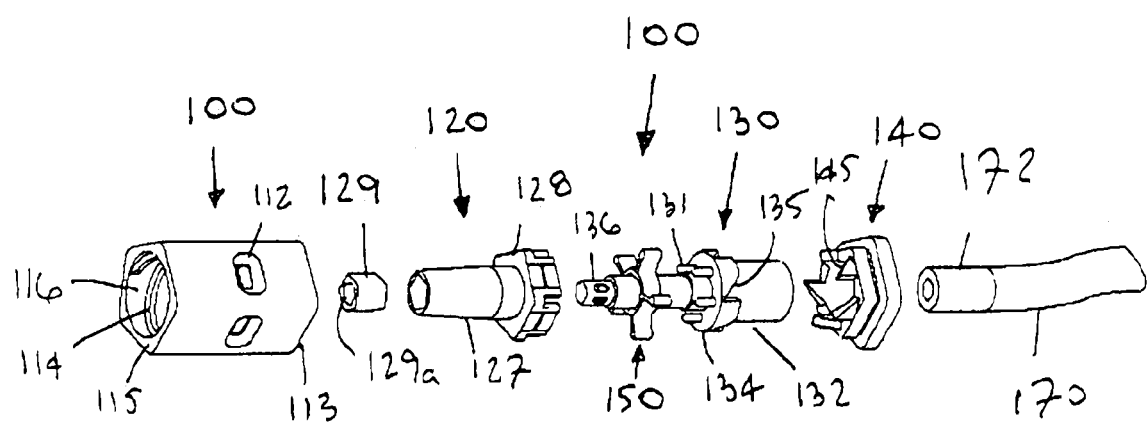
FIG. 1B is an exploded view of the passive connecting assembly of FIG. 1A, showing the outer shell with a proximal throughbore including a Luer thread, a distal fluid path and status windows; a covering body including a male boss with a deformable membrane and an outer mating surface including status indicators; a shaft with an elastic member and a mating member; a backing member with cam elements for interacting with the mating member, and the section of tubing.

An exemplary embodiment of a passive connection assembly 100 is shown in FIGS. 1A and 1B that generally includes a shaft, core pin, conduit, or other tubular member 130, a backing member or cover 140, a covering body or inner housing 120, and an outer shell or bezel 110. As explained further below, the shaft 130 may interact with the covering body 120 and backing member 140 to provide a selectively opened fluid path through the assembly 100. The assembly 100 includes interacting cam elements and/or features, which may translate axial action, e.g., when the assembly 100 is connected to a fluid line, into rotational movement, or rotational action into axial movement to open and/or close the fluid path. The assembly 100 may be biased to close or open the fluid path, and the bias may be overcome by the axial or rotational action to open or close the fluid path. The outer shell 110 may include one or more windows 112 that may indicate when the assembly 100 is in open and/or closed conditions, and/or the assembly 100 may include other indicators that may indicate when the assembly 100 is in the open and/or closed conditions. The assembly 100 may include one or more Luer or other connectors, e.g., a male Luer thread 114 as shown on the outer shell 110, for connecting the assembly 100 to a fluid line (not shown). It will be appreciated that other connectors may also be provided instead of the Luer thread 114.

FIG. 1B is an exploded view of the assembly 100 showing the outer shell 110, along with the covering body 120 with a deformable sleeve or membrane 129, the shaft 130 with an elastic member 150, and the backing member 140. The various components of the assembly 100 shown in FIG. 1B are shown in further detail in FIGS. 2-5 and described further below.

Figure 2:
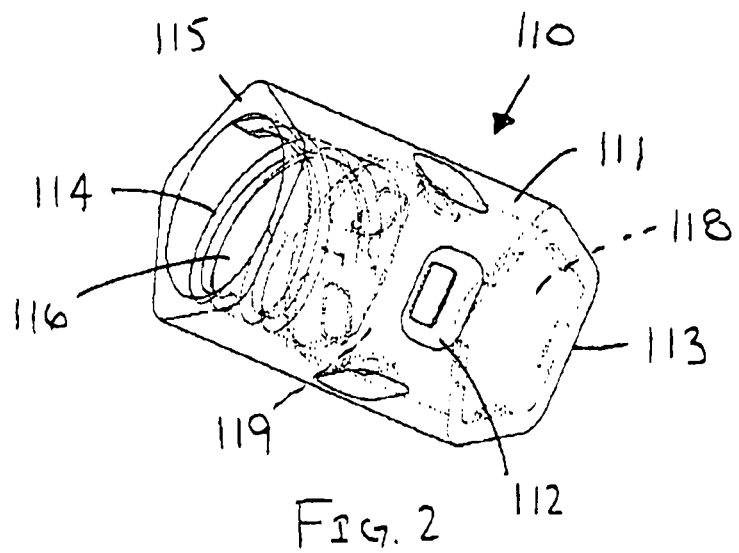
FIG. 2 is a perspective view of an exemplary embodiment of the outer shell of the connecting assembly of FIGS. 1A and 1B that includes proximal and distal throughbores, a proximal Luer thread, and status windows.

FIG. 2 shows the outer shell 110, which includes one or more status windows 112 in an outer surface 111 thereof, an unthreaded portion 115 with a distal throughbore 118, and a proximal throughbore 116, e.g., for receiving the covering body 120 and shaft 130 therethrough. The proximal throughbore 116 may include the male Luer thread 114 therein. As shown, the outer shell 110 includes a pentagon shaped outer surface 111, although alternatively the outer surface 111 may include other shapes, e.g., to facilitate a user easily gripping and/or manipulating the outer shell 110, for example, to engage the male Luer thread 114 with a female Luer connector (not shown) via a threading action. Exemplary shapes include a triangle, square, hexagon, heptagon, and other suitable polygons.

The distal throughbore 118 extends through the unthreaded portion 115 from distal end 113 of the outer shell 110 to an intermediate location 119, which may be situated as shown at or near the midpoint of the length of outer shell 110, e.g., such that the distal throughbore 118 communicates with proximal throughbore 116. The longitudinal distance of distal throughbore 118 from the distal end 113 to the intermediate location 119 is sufficient to accommodate the outer mating surface 128 of covering body 120 (See FIG. 3) and shaft 130 (See FIG. 4A).

The distal throughbore 118 may be pentagonal in shape as shown, or it may be any other shape (e.g., a triangular, square, pentagonal, hexagonal, heptagonal, octagonal, or other polygonal shape) as long as it is able to receive, effectively contact, and limit movement of the covering body 120 (See FIG. 3) and the backing member 140 (See FIG. 5) relative to the outer shell 110 when the assembly 100 is being engaging, e.g., with a female Luer connector 160 of a fluid line (not shown, see FIGS. 6A(1) and 6A(2)). For example, this polygonal shape may ensure that the outer shell 110, covering body 120, and backing member 140 all rotate substantially in unison. The polygonal shape may also ensure that the backing member 140 does not move axially relative to the outer shell 110 and/or may allow limited axial motion of the covering body 120 within the outer shell 110. The same shape may be used for the distal throughbore 118 and the outer surface 111 of the outer shell 110, e.g., for manufacturing convenience, but the device may still function even if these shapes are different. The shape and size of the distal throughbore 118, however, should correspond substantially to the shape and size of both the outer mating surface 128 of the covering body 120 and proximal end segment 144 of the backing member 140, as explained further elsewhere herein. Thus, the outer shell 110, covering body 120, and backing member 140 rotate together, while the shaft 130 (See FIG. 4A) may rotate independently of the other components, also as described further elsewhere herein.

The proximal throughbore 116 may be circular in shape and include the Luer threads 114, as shown in FIG. 2. This facilitates mating the outer shell 110 with a female Luer connector 160 (not shown, see FIGS. 6A(1) and 6A(2)), e.g., when engaging the two connectors to couple the assembly 100 with an IV or other fluid line (also not shown). The longitudinal distance or depth of the proximal throughbore 116 is sufficient to accommodate the male boss 127 of the covering body 120 (See FIG. 3) being received therethrough with the proximal end of the male boss 127 projecting past the proximal end 115 of the outer shell 110 when the male boss 127 is fitted within the proximal throughbore 116. The Luer thread 114 may have conventional dimensions, such as those of the ISO industry standards, e.g., to allow compatibility with standard Luer connectors. The diameter of the distal throughbore 118 may be large enough to accommodate receiving the covering body 120 therethrough, to make contact with and mate with the outer mating surface 128 (See FIG. 3) of the covering body 120, and/or to fit over and mate with the proximal end segment 144 of the backing member 140.

The status windows 112 may be arranged circumferentially around outer surface 111 of the outer shell 110, as shown in FIG. 2. The windows 112 may be rectangular in shape as shown, or may have any other shape including but not limited to circles, triangles, etc., as long as the windows 112 may fit over and reveal deactuated status indicators 125 and/or actuated status indicators 126 on the surface of the covering body 120 (See FIG. 3). Although five windows are shown in FIG. 2, any number of windows may be provided, e.g., that allow a user to easily see at least one status indicator 125, 126 during actuation and/or deactuation. The status windows 112 may be located on the outer surface 111 at or near a mid-point along a length of the outer shell 110, or they may be located elsewhere on the outer surface 111 of the outer shell 110 as long as they are capable of revealing one or more of the status indicators 125, 126 when in the actuated and/or deactuated states. It will be appreciated that the assembly 100 may include other status indicators (not shown) in addition or instead of the status windows 112 and status indicators 125, 126, as described elsewhere herein.

Figure 3:
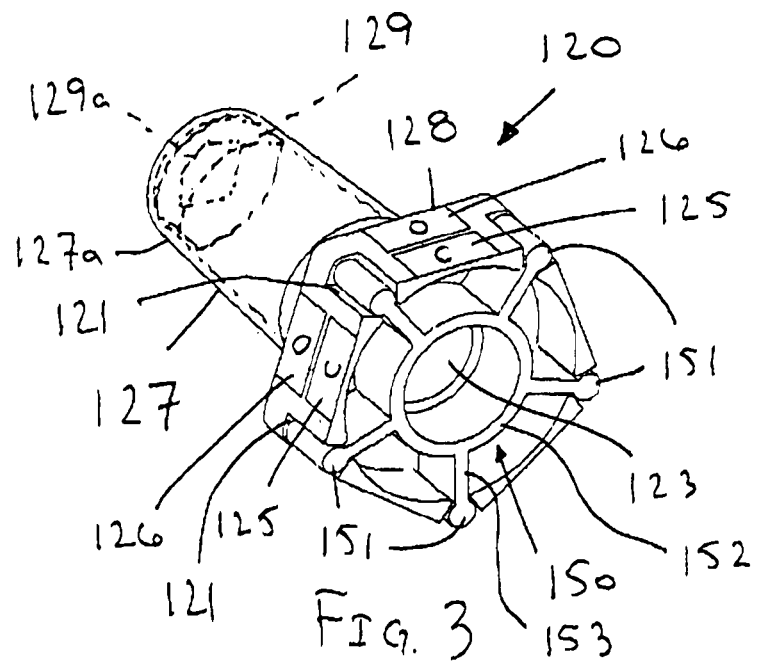
FIG. 3 is a perspective view of an exemplary embodiment of the covering body of the connecting assembly of FIG. 1B that includes a male boss with a deformable membrane, an outer mating surface possessing status indicators, recesses on a distal side of the outer mating surface for receiving an elastic member, and a throughbore.

FIG. 3 shows the covering body 120, which includes a male boss 127 with a deformable housing 129, a throughbore 123, and status indicators 125, 126 disposed on an outer mating surface 128. Also shown in FIG. 3, the covering body 120 includes recesses 121 for receiving end hubs 151 of the elastic member 150, as described further below. Alternatively, the covering body 120 may include projections (not shown) around which an elastic band or member (not shown) may be secured. In an exemplary embodiment, the male boss 127 may be dimensioned per ISO industry standards, and may be cylindrical in shape with a tapered proximal end 127a. During assembly, the outer mating surface 128 may contact the distal throughbore 118 of the outer shell 110 at or near location 119 (not shown, see, e.g., FIG. 2) when the covering body 120 is inserted into the outer shell 110 (See FIGS. 1A and 1B). The outer mating surface 128 may have the same shape and size as the distal throughbore 118 of outer shell 110 in order for the outer mating surface 128 to fit within and make contact with the distal throughbore 118 of the outer shell 110, i.e., to allow axial movement but prevent rotation of the covering body 120 within the outer shell 110.

The status indicator(s) 125, 126 may be seen in FIG. 3 on the outer mating surface 128. The status indicator(s) 125, 126 may signify to a user when actuation and/or deactuation is complete, as described elsewhere herein. The color or design of the deactuated status indicator(s) 125 may represent deactuation or a "closed" no-flow condition for the assembly 100 while the color or design of the actuated status indicator(s) 126 may represent actuation or an "open" or flow condition for the assembly 100. For simplicity, the deactuated status indicator 125 is shown with the letter "C" (for "closed") while the actuated status indicator 126 is shown with the letter "O" (for "open"), although color indicators may be more easily identified during use (e.g., red for closed and green for open). These indicators 125, 126 may be painted, glued, etched, and/or attached to the outer mating surface 128 via any method known in the art. The status indicators 125, 126 may have very minimal thickness so as not to increase the girth of the outer mating surface 128, i.e., to avoid any increased resistance between the outer mating surface 128 and the outer shell 110.

As the fluid path is actuated during use, the status windows 112 on the outer shell 110 may reveal one or more actuated status indicators 126 (see, e.g., FIG. 6D(1)). This signifies that actuation is complete and that the user should not detach the two mated Luer connectors 114, 160 (unless it is desired to close the fluid path). When the user wishes to close the fluid path, the user may unthread the two Luer connectors and when the status windows 112 reveal one or more deactuated status indicators 125, then deactuation is complete (see, e.g., FIG. 6A(1)). The actuation and deactuation processes are described further below with respect to the other structural components. It will be appreciated that, optionally, only one set of status indicators may be provided, if desired (not shown), e.g., to indicate only the actuated or deactuated state, rather than the two sets shown.

The recesses 121 may be located at each corner of the distal side of the outer mating surface 128 (e.g., forming apices of the star-shape), as shown in FIG. 3. The recesses 121, along with their counterpart pegs 131 described further below, hold elastic member 150 in place. The recesses 121 may have a height such that they are capable of stably holding the hubs 151 of the elastic member 150 in place. As shown, the elastic member 150 includes a central annular base 152 from which spokes 153 extend to the hubs 151. The hubs 151 may be securely received in the recesses 121, e.g., by using an interference fit, bonding with adhesive, sonic welding, and the like. The spokes 153 may be used to store energy, i.e., to bias the elastic member 150, and consequently the shaft 130 towards a position corresponding to the closed (or optionally open) condition. For example, as explained elsewhere herein (and shown in FIGS. 6G and 6H), during use, e.g., when connecting and/or opening the fluid path of the assembly 100, the pegs 131 may deform the spokes 153 radially when the shaft 130 is rotated, thereby storing energy, which may be released when the assembly 100 is closed and/or disconnected.

The elastic member 150 may be composed of any commonly used material in the art such that it is capable of maintaining a stable, and slightly stretched state (e.g., while in the undeformed star-shape shown in FIG. 3), and thereafter being deformed to the configuration illustrated in FIG. 6F. Thus, the elastic member 150 should be strong enough to avoid tearing or breakage when in the deformed state shown in FIG. 6F, be elastic enough to pull itself back into the undeformed star-shape shown in FIG. 3 when allowed, yet not be too resistant to prevent a user from manipulating it successfully between the two states (e.g., expanded and star-shapes). It will be appreciated that other energy storage devices or biasing mechanisms may be provided instead of the elastic member 150, e.g., an elastic band, spring, and the like, as described elsewhere herein.

The throughbore 123 runs the entire length of the covering body 120, e.g., from the outer mating surface 128 through the male boss 127 to the deformable membrane 129, as shown in FIG. 3. The throughbore 123 may be circular and/or have a diameter exactly or substantially equal to the outer diameter of the conduit 132 of the shaft 130 (not shown, see, e.g., FIG. 4A). The deformable membrane 129 may be located inside the proximal end of the throughbore 123, as shown in FIG. 3, or may be disposed over the proximal end of the throughbore 123 (not shown). The deformable membrane 129 may have a polygonal shaped hollow center 129a that matches the size and shape of fluid cap 136 of the shaft 130.

The deformable membrane 129 is fixedly attached to the male boss 127, e.g., about its outer circumference, such that the opening 129a in the deformable membrane 129 remains substantially stationary while the fluid cap 136 of the shaft 130 rotates, i.e., is capable of being deformed while remaining attached to the male boss 127, as described elsewhere herein. For example, the proximal end 127a of the male boss 127 may have a polygonal or other noncircular recess therein and the outer surface of the deformable membrane 129 may have a similar shape. This may provide an interference fit when the deformable membrane 129 is inserted into the male boss 127, i.e., preventing rotation of the deformable membrane 129 relative to the male boss 127. Optionally, the deformable membrane 129 may be attached to the male boss 127 by bonding with adhesive, sonic welding, fusing, and the like in addition to or instead of the interference fit. The deformable membrane 129 is durable enough to resist ripping or tearing during actuation, yet strong and resilient enough to assume its original polygonal shape after deactuation. Similar to the elastic member 150, the deformable membrane 129 may be composed of an elastomeric material, e.g., silicone, or any other suitable material capable of performing the functions described herein.

FIGS. 4A and 4B show the shaft 130, which includes a conduit or tubular body 132 including first and second ends 132a, 132b, a throughbore 133 (shown in FIG. 4B) extending therebetween, a mating member 134 with cam features 135, pegs 131, and a fluid post 136 with one or more side openings 137 on the first end 132a. Optionally, the second end 132b may include one or more connectors (not shown), a length of tubing, and the like. As shown in FIG. 4B, the second end 132b includes an enlarged recess 139, which may be sized for receiving an end 172 of a section of tubing 170 (not shown, see FIG. 1B). The tubing 170 may be substantially permanently or removably received in the recess 139, e.g., using an interference fit, one or more mating connectors (not shown), bonding with adhesive, sonic welding, and the like. The shaft 130 and the mating member 134, together with their respective components may be substantially permanently connected to one another, e.g., by integrally molding the shaft 130, the mating member 134, and pegs 133 from a single piece, or by forming the components separately and attaching them together, e.g., by interference fit, mating connectors, bonding with adhesive, sonic welding, and the like.

Also shown in FIG. 4A is the elastic member 150, which is the same as elastic member 150 shown in FIG. 3, but here it is shown with the pegs 131 disposed adjacent to and/or between the spokes 153. Thus, the elastic member 150 resides both around the shaft 130, e.g., above the proximal surface of the mating member 134, and on the distal underside of the outer mating surface 128 (not shown, see FIG. 3), e.g., when the shaft 130 is inserted into the covering body 120 (e.g., before or after inserting the covering body 120 into the outer shell 110), e.g., for elastically coupling the covering body 120 with the shaft 130. FIG. 4B also shows the throughbore 133 extending through the length of the conduit 132, which extends almost the entire length of the shaft 130. The fluid post 136 resides at the proximal end of the conduit 132 and the opening(s) 137 communicate with the throughbore 133. The fluid post 136 has a corresponding polygonal shape that matches the inside opening 129a of the deformable membrane 129 (not shown, see, e.g., FIG. 6C). The polygonal shape used for the fluid post 136 is shown as a pentagon, but alternatively, any other geometric shape as described above for the outer mating surface 128 may be used for both the fluid post 136 and the opening 129a in the deformable membrane 129.

The outer mating member 134 is shown located near the midpoint of the conduit 132. The mating member 134 may be positioned along the external surface of the conduit 132 so that when the shaft 130 is inserted into the covering body 120, as shown in FIGS. 1A and 1B, the distal side of the outer mating surface 128 makes contact with the proximal side of the mating member 134. In this position, the recesses 121 and pegs 131 hold the elastic member 150 in the star-shape, as shown in FIGS. 3 and 4A. The star-shape assumes five recesses 121 on the covering body 120 and five pegs on the mating member 134, as well as five spokes 153 and hubs 151 on the elastic member 150 due to the pentagonal shape shown, but the number of recesses and pegs. Thus the shape of the elastic member 150 may be changed, e.g., to correspond with the selected polygonal shape used for the outer mating surface 128 and its matching components.

The pegs 131 are attached to and/or otherwise extend from the proximal side of the mating member 134, as shown in FIG. 4A. The pegs 131 may couple rotational motion of the annular base 152 of the elastic member 150 to rotation of the shaft 130.

Triangular indentations or cam features 135 are located on the distal side of the mating member 134. These cam features 135 may mate with triangular projections, splines or other mating cam elements 145 located on the backing member 140 shown in FIG. 5 in order to effect actuation. The angle of each hypotenuse of these cam components (e.g., cam features 135 and cam elements 145) may be changed to correspond to the selected polygonal shape of the fluid post 136 in order to maximize fluid flow upon actuation of the assembly 100. Also, the size and depth of the cam features 135 may be changed with the polygonal shape of the fluid cap 136 to successfully effect or maximize actuation flow. The relationship of the sizes and hypotenuse angles are further described below.

Figure 5:
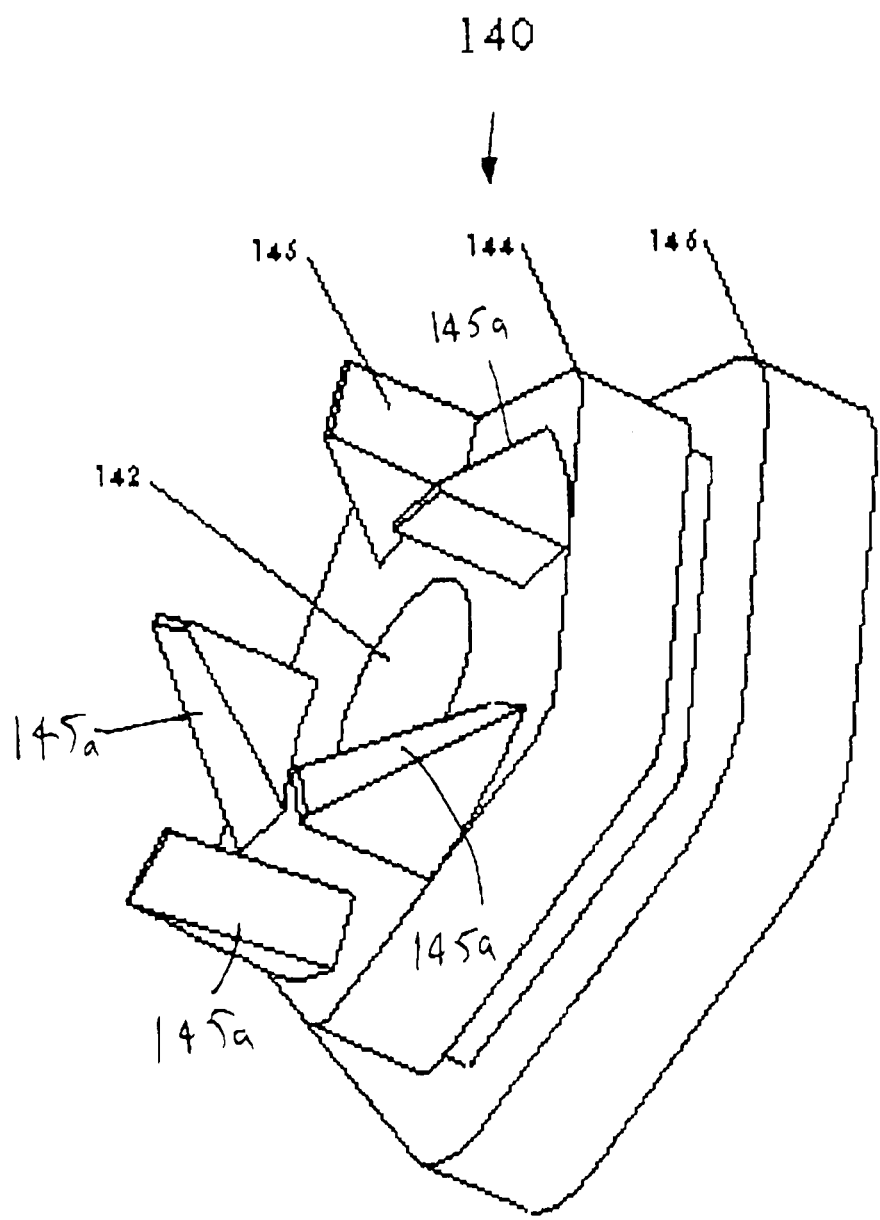
FIG. 5 is a perspective view of an exemplary embodiment of the backing member of the connecting assembly of FIG. 1B that includes cam elements, a throughbore, and proximal and distal end segments.

FIG. 5 shows the backing member 140, which includes the cam elements 145, a proximal, relatively small end segment 144, a distal, relatively large end segment 146, and a throughbore 142. The cam elements 145 are attached to and/or otherwise extend from the proximal side of the proximal end segment 144 and are designed to mate with the cam features 135 shown in FIG. 4A, e.g., when the covering body 120 is directed towards the backing member 140 during actuation, as explained elsewhere herein. Generally, the cam elements 145 and cam features 135 include ramped or angled surfaces 145a, 135a that interact to cause rotational motion of the shaft 130 relative to the backing member 140 in response to axial movement of the covering body 120 (or vice versa), as explained elsewhere herein. The proximal end segment 144 has a corresponding polygonal shape and size such that it matches the shape and size of the distal throughbore 118 of outer shell 110. Thus, the proximal end segment 144 may be received within the distal throughbore 118, thereby coupling rotation of the outer shell 110 to the backing member 140. The proximal end segment 144 (or other features of the backing member 140) may be substantially permanently attached to the outer shell 110, e.g., using an interference fit, one or more mating connectors (not shown), bonding with adhesive, sonic welding, and the like. It will also be appreciated that other interlocking features and/or shapes may be provided for coupling the outer shell 110 to the backing member 140.

The distal end segment 146 of the backing member 140 has an outer surface that has substantially the same polygonal shape and size of the outer surface 111 of the outer shell 110 in order for it to fit against the distal end 113 of the outer shell 110, e.g., to provide a continuous outer surface for the assembly 100. The throughbore 142 may be circular and/or have the same or substantially the same diameter and/or shape as the conduit 132 of the shaft 130.

Figure 6G:
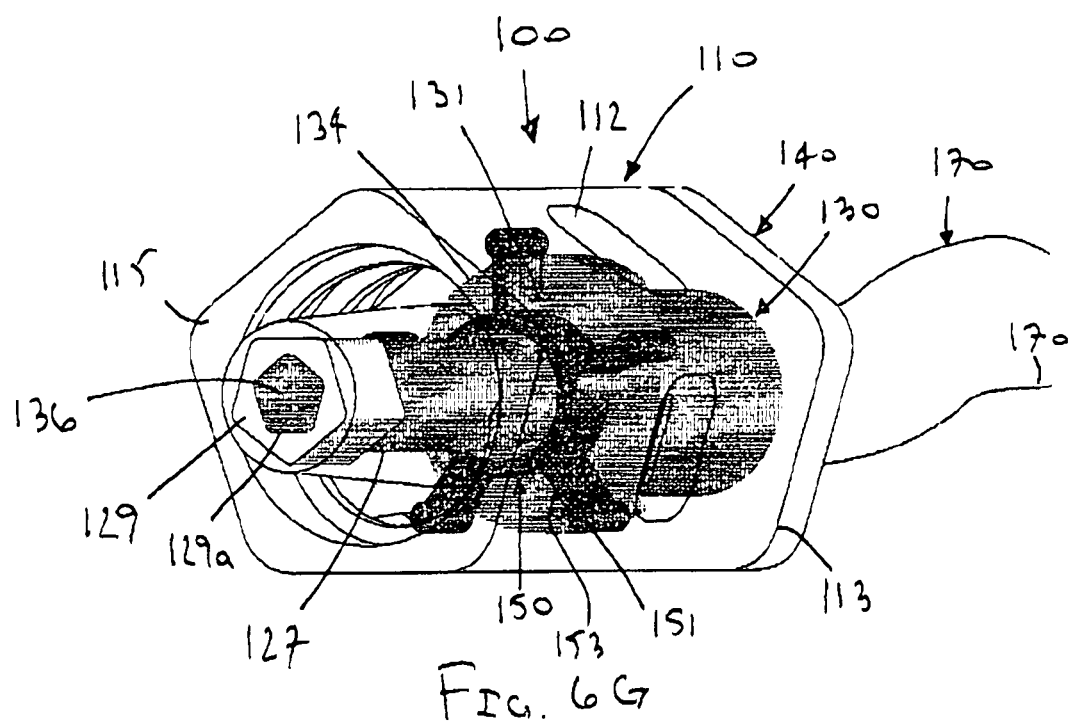
FIG. 6G is a perspective view of the deactuated connecting assembly shown in FIGS. 6A(1) and 6A(2) with the outer shell shown in phantom for clarity.

FIGS. 6A-6H show the assembly 100 of the covering body 120, shaft 130, backing member 140, and elastic member 150. The outer shell 110 is shown in FIGS. 6A(1) and 6D(1), but has been excluded from FIGS. 6A(2) and 6D(2) for simplicity, e.g., to show the inner workings of the assembly 100. During manufacturing, the various components of the assembly 100 may be formed, e.g., by injection molding, machining, forming, and the like. The components may be formed from metal, plastic, and/or composite materials, as desired. Once the components are made, they may be assembled into the assembly 100.

In an exemplary method, the annular base 152 of the elastic member 150 may advanced over the fluid cap 136 onto the shaft 130, e.g., until the spokes 153 are disposed between the pegs 131. The shaft 130 may then be inserted into the covering body 120, e.g., until the hubs 151 of the elastic member are received in the recesses 121 in the outer mating surface 128. The deformable membrane 129 may be inserted into the male boss 127 of the covering body 120. The covering body 120 may then be inserted into the distal end 113 of the outer shell 110, e.g., after aligning the outer mating surface 128 with the distal throughbore 118 of the outer shell 110. The backing member 140 may then be connected to the outer shell 140 to close the distal throughbore 118. The backing member 140 may be substantially permanently attached to the outer shell 110, e.g., using cooperating connectors, bonding with adhesive, sonic welding, fusing, and the like.

Optionally, a section of tubing 170 may be attached to the shaft 130, e.g., through the backing member 140. Alternatively, a portion of the shaft 130 (not shown) may extend through the backing member 140, e.g., terminating in a connector (not shown), to allow a section of tubing or other device (also not shown) to be attached to the shaft 130. The resulting assembly 100 provides a covering body or inner housing 120 contained within the outer shell 110 and backing member or cover 140 such that the male boss 127 is disposed adjacent the Luer thread 114 in the outer shell 110. The covering body 120 may be movable axially, e.g., when the male boss 127 is contacted and pushed axially into the outer shell 110. The shaft 130 may be free to rotate within the assembly 100, e.g., limited by the interaction of the cam features 135 and cam elements 145 as described further below.

During use, as shown in FIGS. 6A-6H, a female Luer fitting 160 may be connected to the Luer thread 114 in the outer shell 110. The female Luer fitting 160 may be connected to a length of tubing, piece of equipment, container, and the like (not shown), which may be part of the IV or fluid line to which the assembly 100 is to be connected. The outer shell 110 (not shown) has the inner thread from male Luer 116 into which the female Luer fitting 160 may be threaded.

Initially, in the deactuated condition shown in FIGS. 6A(1) and 6A(2), the covering body 120 is biased away from the backing member 140. This is due to the securing of the hubs 151 of the elastic member 150 in the recesses 121 and the position of the pegs 131, as best seen in FIGS. 6B and 6G. Although the angled surfaces 135a, 145a of the cam features 135 and cam elements 145 may contact one another, the elastic member 150 may bias the shaft to slide up the surfaces 135a, 145a, i.e., away from the backing member 140 and towards the male Luer thread 114 on the outer shell 110. In this deactuated condition, the deactuated status indicators 125 may be aligned axially with the status windows 112.

As the female Luer fitting 160 threads into the outer shell 110, it contacts the male boss 127. Due to the tapered design of the male boss 127, the female Luer fitting 160 pushes the covering body 120 axially towards the distal end 113 of the outer shell 110, thereby directing the shaft 130 within the covering body 120 also to be directing axially towards the backing member 140. As the covering body 120 is pushed towards the backing member 140 by the female Luer fitting 160 contacting the male boss 127, the mating member 134 and shaft 130 are pushed along with the covering body 120. As the covering body 120 is directed axially, as best seen in FIG. 6D(1), the actuated status indicators 126 become aligned with and can be seen through the status windows 112.

The resulting axial movement of the shaft 130 causes the cam features 135 to interact with the cam elements 145 to rotate the shaft 130 relative to the backing member 140 and, consequently, the outer shell 110 and covering body 120. More specifically, the ramped surfaces 135a of the cam features 135 slide along the ramped surfaces 145a of the cam elements 145, thereby translating the axial movement of the covering body 120 into axial and rotational movement of the shaft 130. The proximal tips of the cam elements 145 are lined up with the sloping corners of each hypotenuse of the cam features 135 before actuation, as shown in FIG. 6A(2). As the shaft 130 is pushed distally, the cam features 135 are forced to mate with the cam elements 145, which forces the mating member 134 along with the rest of the shaft 130 to rotate.

As the shaft 130 rotates, the fluid cap 136 rotates inside the opening 129a in the deformable membrane 129. Before rotation, the polygonal shape of the fluid cap 136 is matched up with the polygonal shape of the opening 129a in the deformable membrane 129, thereby providing a substantially fluid-tight seal between the deformable member 129 and the fluid cap 136, i.e., sealing a fluid inside throughbore 133, as shown in FIG. 6C. Rotation of the shaft 130 causes the fluid cap 136 and deformable membrane 129 to mismatch, thereby creating gaps 129b between the deformable membrane 129 and the fluid cap 136, as shown in FIG. 6F. The elasticity of the deformable member 129 allows the fluid cap 136 to twist freely within the opening 129a. Once mismatched, gaps 129b are created between the fluid cap 136 and the deformable membrane 129, and fluid inside the throughbore 133 may now flow through the gaps 129b and into the female Luer fitting 160. At this point, the actuated status indicator 126 is seen through the status windows 112, as shown in FIG. 6D(1).

The angle of each hypotenuse of the cam elements 145 and cam features 135 are such that when the shaft 130 is rotated to the point where the cam elements 145 are mated with the cam features 135, the fluid cap 136 is evenly mismatched with the deformable membrane 129. Evenly mismatched, in this sense, means that each of the points of the fluid cap 136, which is selectively shaped from the polygonal shapes mentioned above, are in substantially the midpoint of the sides of the opening 129a in the deformable membrane 129. Thus, with the use of pentagonally shaped members, there are five substantially equal triangular gaps 129b formed when the assembly 100 is in the actuated condition. Each point of the pentagonally shaped fluid cap 136 is situated on the midpoint of the sides of the pentagonally shaped opening 129a in the deformable membrane 129, as best seen in FIG. 6F. Although other degrees of deformation may work, the described deformation of the deformable membrane 129 may maximize the rate of fluid flow.

Figure 6H:
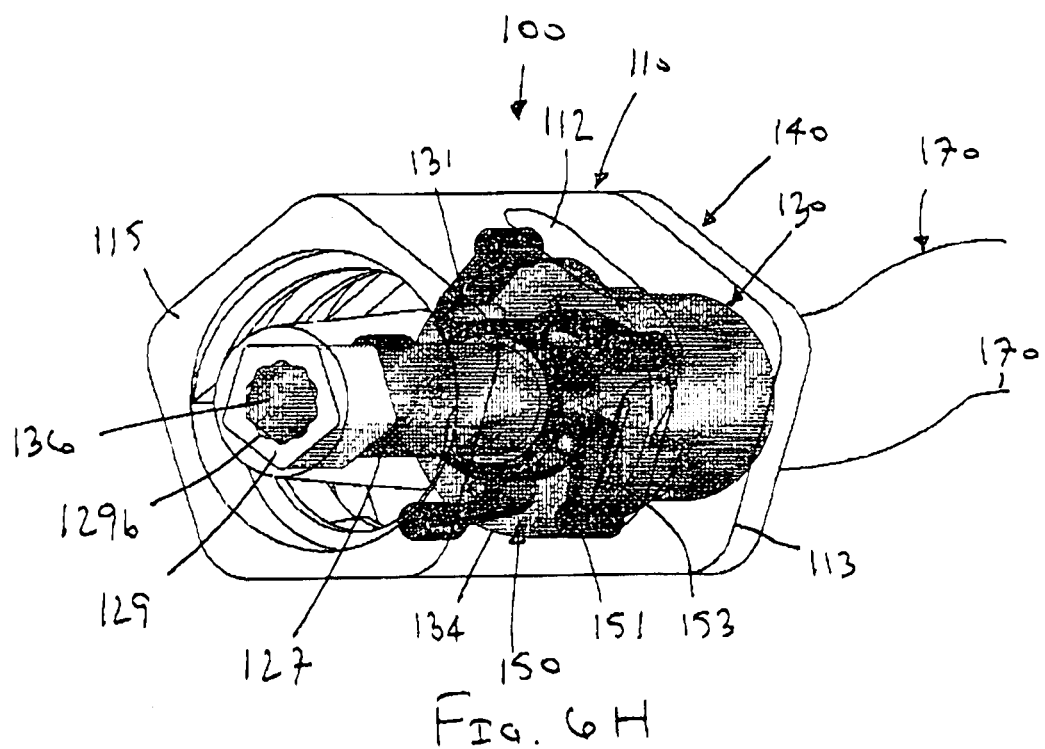
FIG. 6H is a perspective view of the actuated connecting assembly shown in FIGS. 6D(1) and 6D(2) with the outer shell shown in phantom for clarity.

As the shaft 130 rotates, the spokes 153 of the elastic member 150 become stretched or deformed, as shown in FIGS. 6E and 6H, e.g., storing potential energy in the elastic member 150. The elastic member 150 is held in this stretched state by virtue of the mating between the cam features 145 and the cam elements 135. When the female Luer fitting 160 is disconnected, the energy stored in the spokes 153 of the elastic member 150 on the shaft 130 is not impeded anymore, and the shaft 130 is free to rotate back to its original position. During this deactuation process, the cam features 135 slide along the cam elements 145 causing the shaft 130 to move axially away from the backing member 140 as the shaft 130 rotates. This separation allows the shaft 130 and the covering body 120 to reassume their original relative rotational position, and causes the covering body 120 to move axially away from the backing member 140. After the covering body 120 is pushed back towards the proximal end 115 of the outer shell 110 through this deactuation process, the status windows 112 reveal the deactuated status indicator 125 once again.

Turning to FIGS. 7A-12D, another embodiment of a valve/connector assembly 200 is shown that includes an outer shell or bezel 210 and backing member 240, together providing an outer package or housing for the assembly 200, a covering body or inner housing 220, a shaft, core pin, or tubular member 230, and an elastic member 250. These components are generally similar to the similarly identified components of the assembly 100 (with like components having their reference numbers increased by 100 for simplicity). Unlike the assembly 100, the assembly 200 also includes a gear-shaped camming element 260 that may be coupled to the outer shell 110 and backing member 240, as described further below.

Figure 8:
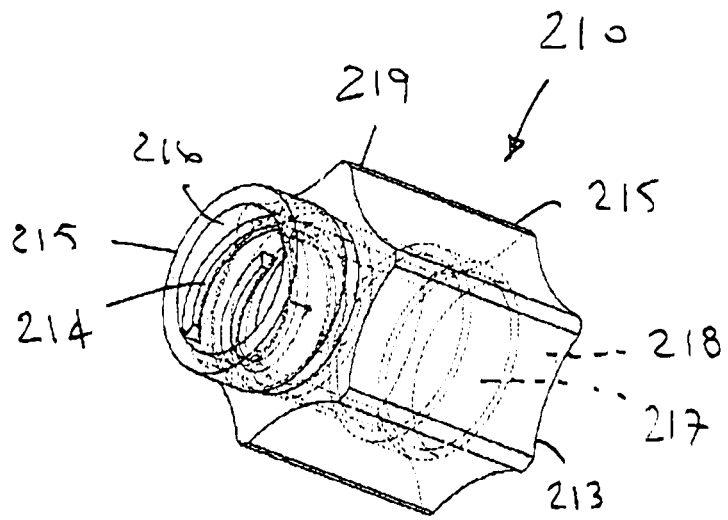
FIG. 8 is a perspective view of the outer shell of the assembly of FIGS. 7A-7C.

With particular reference to FIG. 8, the outer shell 210 includes proximal and distal ends 215, 213, an unthreaded portion 215 adjacent the distal end 213 with a distal throughbore 218 having an annular recess 217 therein, and a proximal throughbore 216 including a male Luer thread 214 therein adjacent the proximal end 215. As shown, the outer shell 210 has a hexagonal shaped outer surface 211, although, alternatively, the outer surface may have any other shape, similar to the previous embodiment. The outer surface 211 may facilitate a user gripping and/or manipulating the outer shell 210, e.g., to engage and/or disengage the male Luer thread 214 with a female Luer connector from a fluid line or other device (not shown).

The distal throughbore 218 extends from the distal end 213 of the outer shell 210 to intermediate location 219. The length, size, and/or shape of the distal throughbore 218 is sufficient to accommodate at least a portion of the covering body 220 and shaft 230 therein (not shown, see FIGS. 7A-7C). The diameter or other cross-section of the distal throughbore 218 may be larger than the proximal throughbore 216, e.g., to provide an abutment surface at the intermediate location 219 for limiting proximal movement of the covering body 220 into the distal throughbore 218, as explained further below.

The annular recess 217 may be disposed between the abutment surface at the intermediate location 219 and the distal end 213, e.g., closer to and/or immediately adjacent the distal end 213. The annular recess 217 may have a slightly larger diameter than the rest of the distal throughbore 218, e.g., having a height and diameter substantially similar to the camming element 260 so that the camming element 260 may be captured within the annular recess 217, e.g., to prevent removal of the camming element 260 while allowing it to spin within the annular recess 217. Thus, as described further below, the outer shell 210 may rotate relative to the camming element 260 and backing member 240, without separating the outer shell 210 from the camming element 260 and backing member 240 (but allowing the outer shell 210 to slide axially relative to the backing member 240).

The dimensions of the proximal throughbore 216 and male Luer thread 214 may be provided according to ISO standards for Luer connectors. Alternatively, other connectors (not shown) may be provided on the proximal end 215, if desired.

Returning to FIGS. 7B and 7C, the covering body 220 includes an elongated male boss 227 with a deformable membrane 229 attached thereto (similar to the previous embodiments), a throughbore 223, and a mating disc 228 including a plurality of teeth or tabs 225 and one or more lips or tabs 221. The male boss 227 may be dimensioned per ISO industry standards, e.g., having a cylindrical shape with a tapered proximal end. The male boss 227 and mating disc 228 of the covering body 220 may be integrally molded or otherwise formed from a single piece or may be separate pieces substantially permanently attached to one another.

Figure 7A:
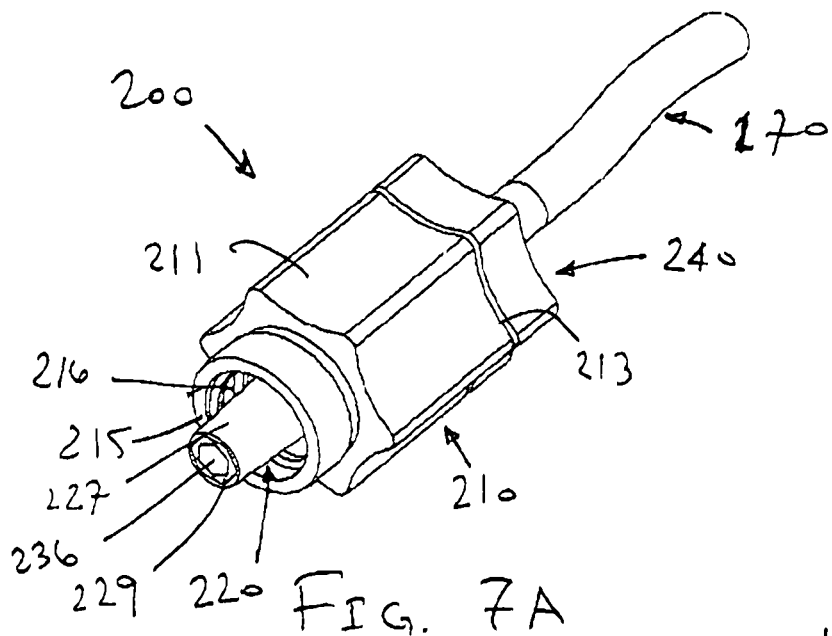
FIG. 7A is a perspective view of another embodiment of a passive connecting assembly including an outer shell with a male Luer thread connected to an distal end of a length of tubing.
Figure 7B:
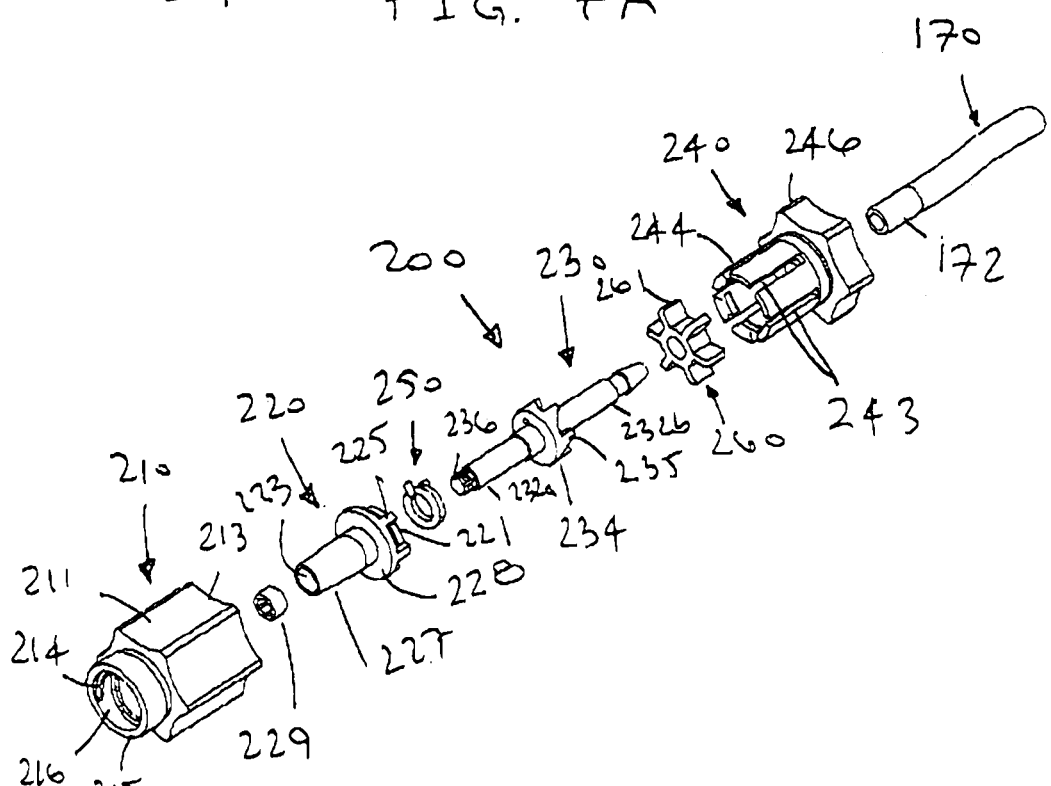
FIGS. 7B and 7C are exploded views of the assembly of FIG. 7A, including an outer shell with a proximal throughbore containing a Luer thread and a distal throughbore; a covering body including a male boss with a deformable membrane and an outer mating surface; a shaft with an elastic member and a mating member; and a backing member.
Figure 7C:
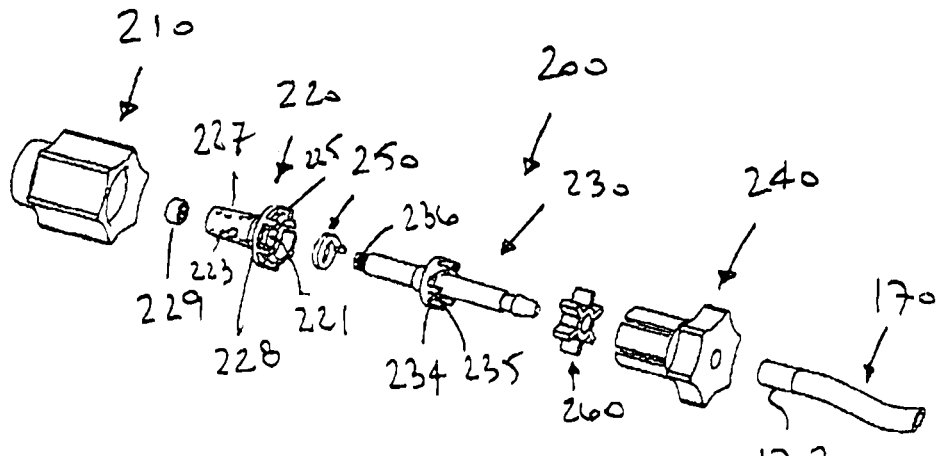

Similar to the previous embodiments, the covering body 220 may be received within the outer shell 210, e.g., by inserting the male boss 227 through the distal throughbore 218 into the proximal throughbore 216, as shown in FIGS. 7A-7C. When the male boss 227 is received in the proximal throughbore 216, the mating disc 228 may be received in the distal throughbore 218, e.g., contacting the abutment surface at the intermediate location 219 (see FIG. 8).

The mating disc 228 may have a diameter that substantially matches that of distal throughbore 218. The teeth 225 are attached to or otherwise extend from the distal side of the mating disc 228 and are configured to match gaps 243 in the backing member 240 (see FIG. 10A), as described further below. Between the teeth 225 is a recessed portion of the mating disc 228 that includes the one or more tabs 221, which are configured to match and/or be received in indentation 241 of the backing member 240. As explained further below, the tabs 225 and tabs 221 may provide detents or connectors for attaching the covering body 220 to the backing member 240. It will be appreciated that other cooperating detents or connectors (not shown) may be provided on the covering body 220 and/or backing member 240 for this purpose.

The throughbore 223 runs the entire length of covering body 220, e.g., through the mating disc 228 and male boss 227. As shown, the throughbore 223 is substantially circular and may have a diameter similar to the outer diameter of conduit 232 of the shaft 230 (except for the proximal-most portion, which may have a polygonal shape for receiving the deformable membrane 229). The deformable membrane 229 may be attached to the male boss 227, e.g., inserted into the proximal portion of the throughbore 223 as shown in FIG. 7A. The deformable membrane 229 may have a polygonal shaped hollow center that matches the size and shape of fluid cap 236 of the shaft 230, as described further elsewhere herein. The deformable membrane 229 may be fixedly attached to the inside of the male boss 227 such that the deformable membrane 229 cannot rotate therein, e.g., when the deformable membrane 229 is being deformed, similar to the previous embodiments.

Figure 9A:
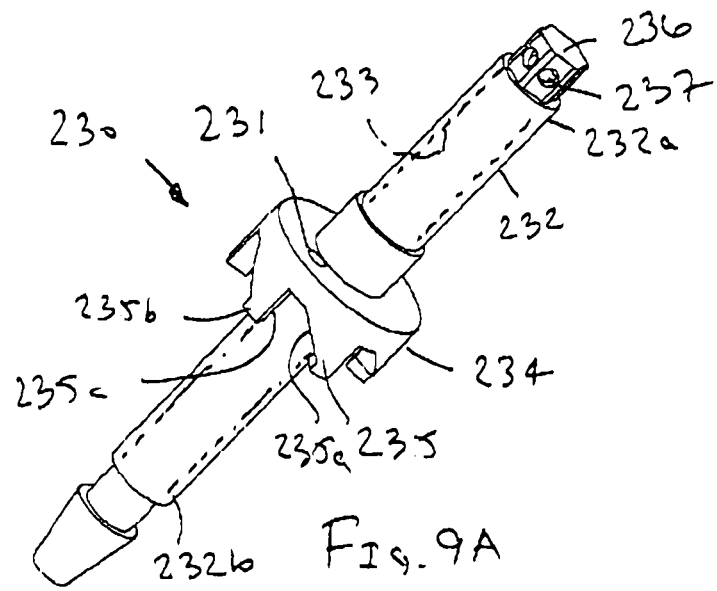
FIGS. 9A and 9B are perspective views of the shaft of the assembly of FIGS. 7A-7C.
Figure 9B:
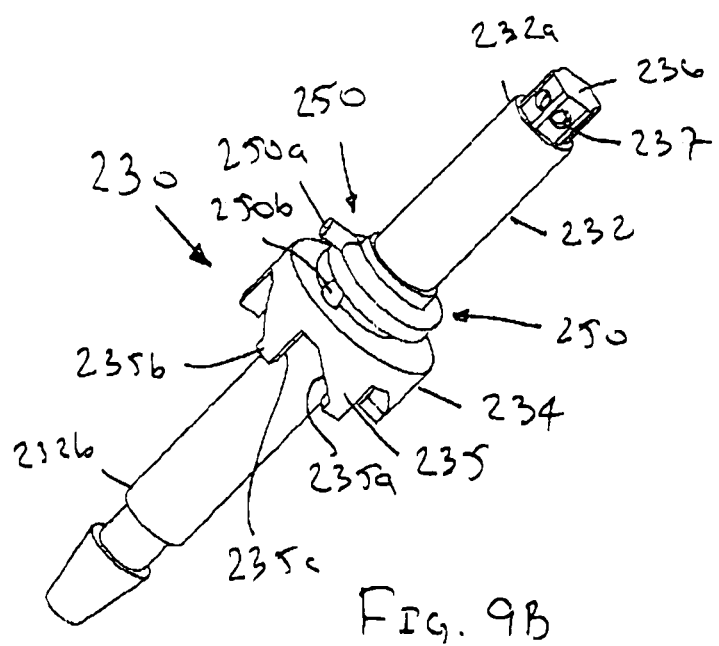

Turning to FIGS. 9A and 9B, the shaft 230 generally includes a conduit 232, a throughbore 233 extending between first and second ends 232a, 232b of the conduit 232, a mating member 234 with a plurality of cam features 235, and a fluid cap 236 with openings 237, similar to previous embodiments. The throughbore 233 extends through conduit 232, e.g., into the fluid cap 236. The fluid cap 236 has a polygonal shape that substantially matches the opening 229a in the deformable membrane 229, and may include one or more openings 237, e.g., on each face of its polygonal shape, e.g., to allow fluid to flow through the openings 237 after actuation of assembly 200, as described elsewhere herein.

Figure 11B:
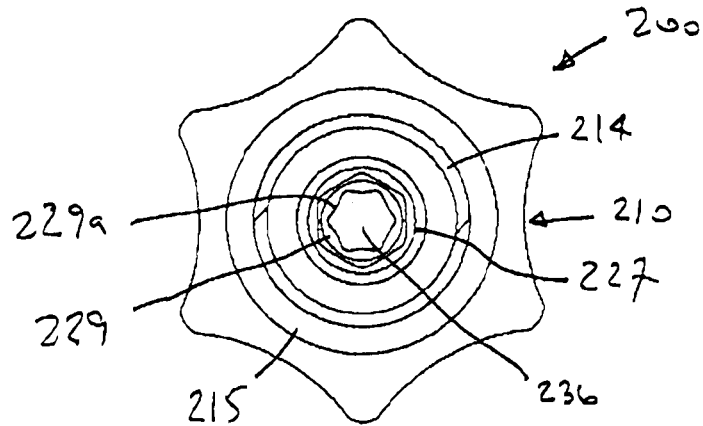
FIGS. 11B and 11C are cross-sectional views of the assembly of FIG. 11A, taken along lines 11B-11B and 11C-11C, respectively.
Figure 11D:
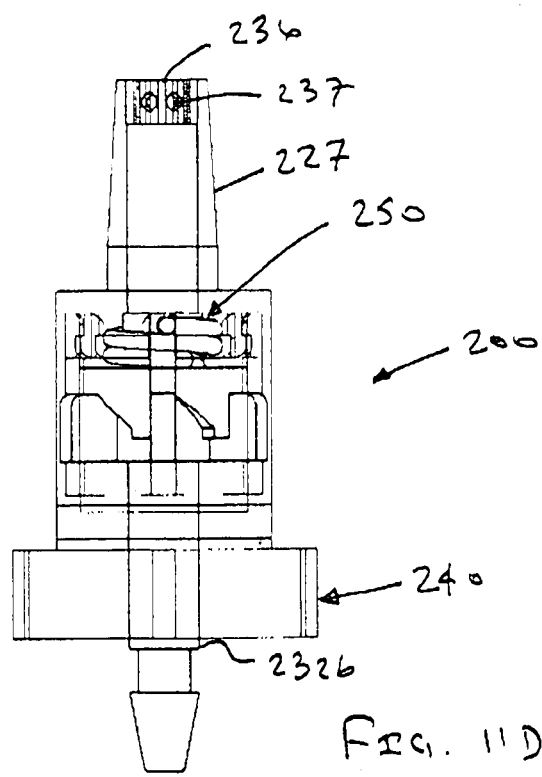
FIG. 11D is a side view of the assembly of FIG. 11A with the outer shell shown in phantom.
Figure 12B:
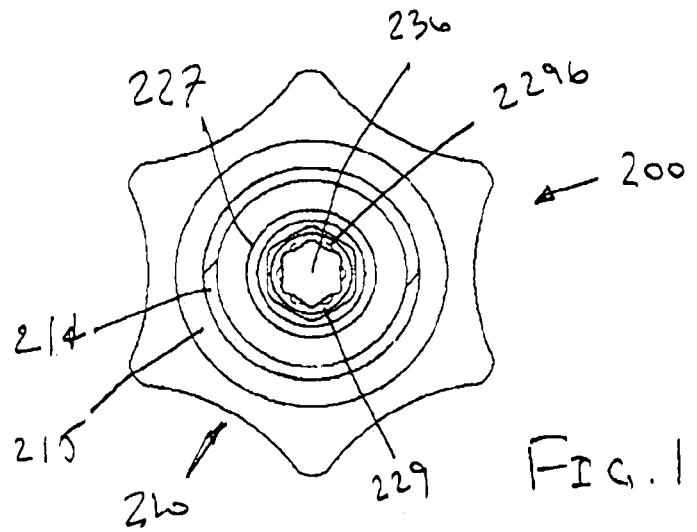
FIGS. 12B and 12C are cross-sectional views of the assembly of FIG. 12A, taken along lines 12B-12B and 12C-12C, respectively.
Figure 12A:
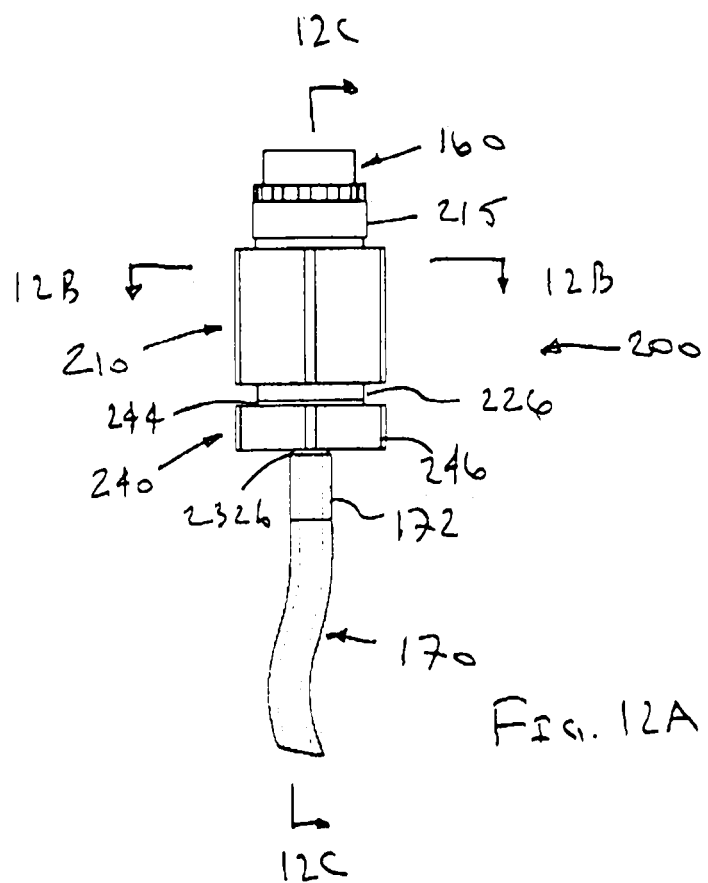
FIG. 12A is a side view of the assembly of FIGS. 7A-7C in an actuated condition after the Luer fitting has been connected to the assembly.
Figure 12C:
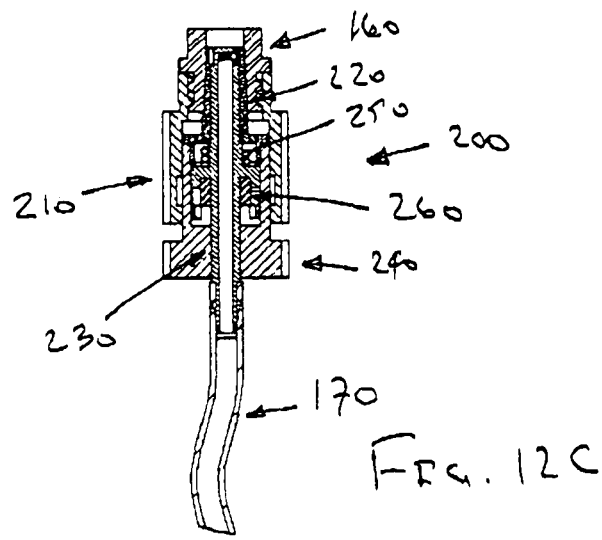
Figure 12D:
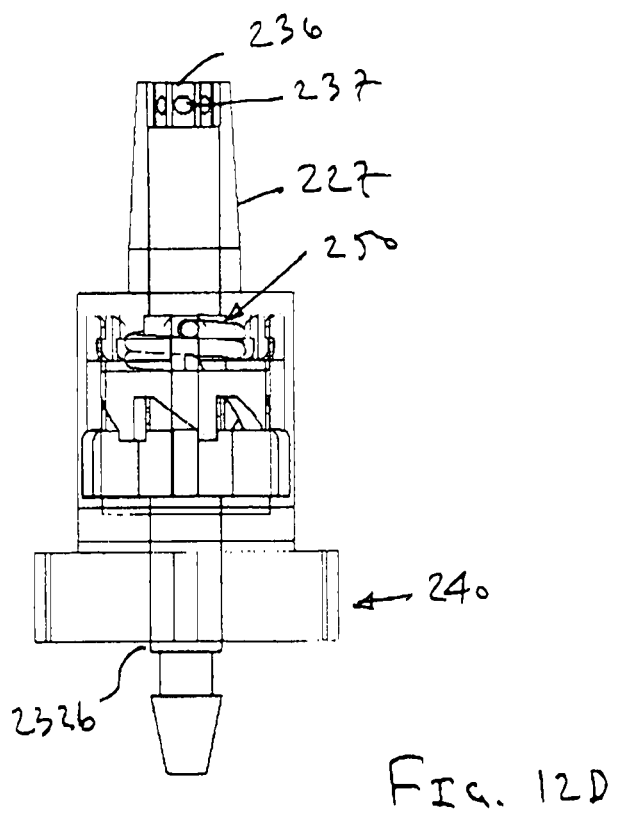
FIG. 12D is a side view of the assembly of FIG. 12A with the outer shell shown in phantom.
Figure 13B:
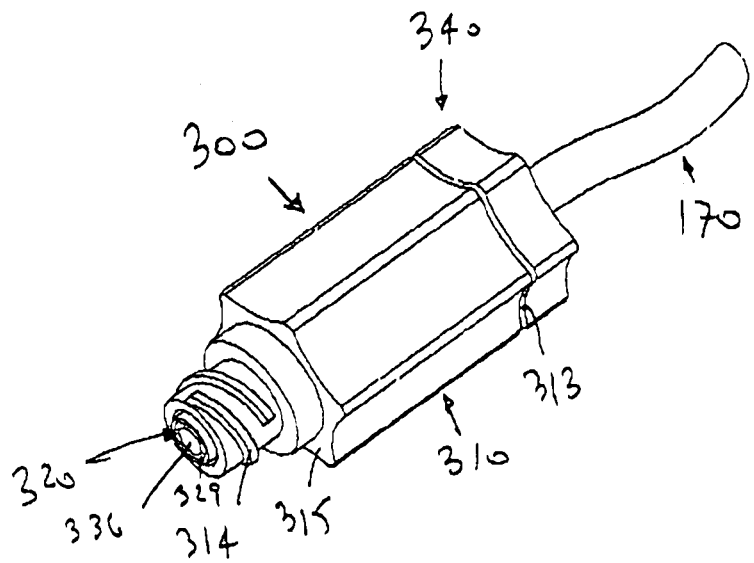
FIGS. 13A-13C are perspective views of yet another embodiment of a valve/connector assembly including a female Luer fitting, shown before and after connection to a male Luer fitting.
Figure 13A:
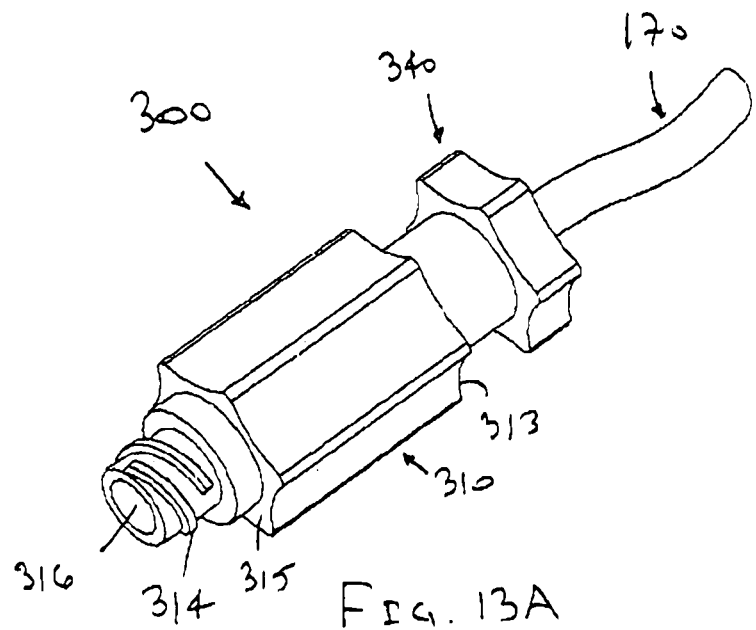
Figure 13C:
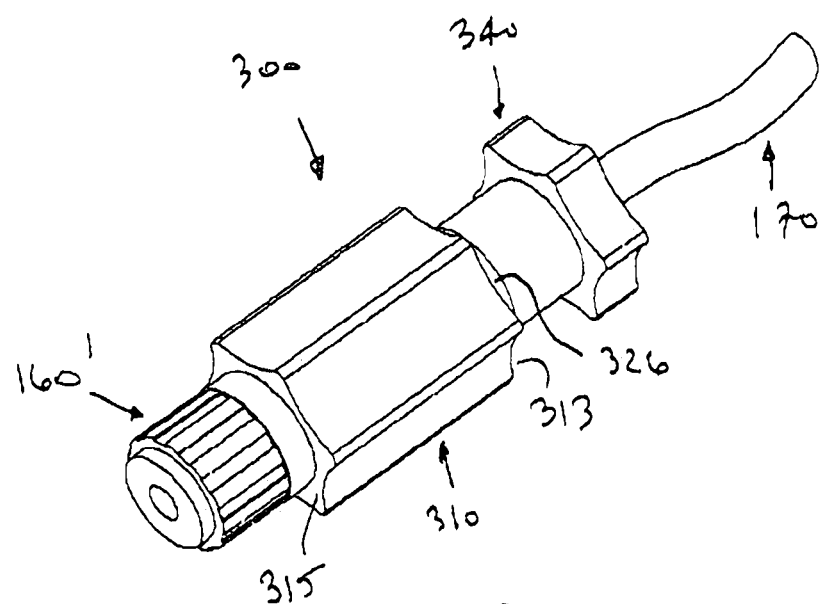

The mating member 234 may be located near the midpoint of the conduit 232. For example, the mating member 234 may be located along a length of the conduit 232 such that, when the shaft 230 is inserted into the covering body 220, as shown in FIGS. 11D and 12D, a distal side of the mating disc 228 may contact a proximal side of the mating member 234, e.g., to limit insertion of the shaft 230 into the covering body 220. The mating member 234 may include one or more holes or other anchor points 231, e.g., located on a proximal side of the mating member 234 to receive a portion of the elastic member 250 and/or otherwise limit movement of the elastic member 250 relative to the shaft 230.

The cam features 235 are located on the distal side of mating member 234, and generally include ramped surfaces 235a, similar to the previous embodiments. The cam features 235 may be configured to contact and/or otherwise interact with the camming element 260, e.g., to effect actuation and/or deactuation of the assembly 200, as described elsewhere herein. Similar to the assembly 100, the angle of each hypotenuse of the cam features 235 may be changed, e.g., to correspond to the selected polygonal shape for the fluid cap 236 and opening 229a, for example, to maximize fluid flow upon actuation. Unlike the assembly 100, each cam feature 235 may also include a tooth or extension 235b on the distal side, which is described further below.

Also shown in FIG. 9B, the elastic member 250 is shown as a coil spring that includes first and second ends 250a, 250b. The elastic member 250 may be sized to be received around the conduit 232 of the shaft 230, e.g., above the mating member 234. As shown, the first end 250a may extend radially outwardly from the shaft 230, and the second end 250b is received in the hole 231 (best seen in FIG. 9A). After assembly, the first end 250a of the elastic member 250 may be captured or otherwise engaged to the covering body 220 and/or backing member 240 to bias the shaft 230 relative to the covering body 220. Alternatively, other elastic members may be provided, similar to the other embodiments described herein.

Figure 10B:
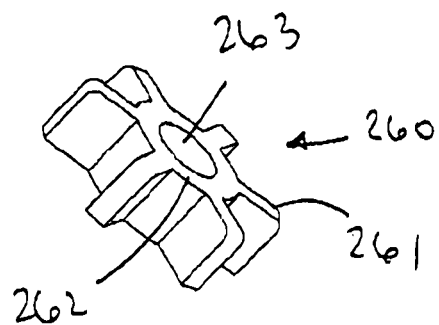
FIGS. 10A and 10B are perspective views of components of a backing member of the assembly of FIGS. 7A-7C.
Figure 10A:
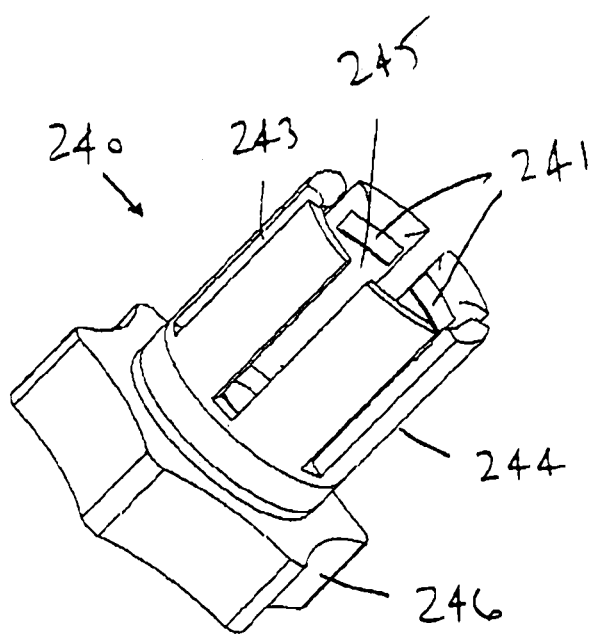

Turning to FIG. 10A, the backing member 240 includes a base portion 246, and an annular portion 244 extending from the base portion 246, together defining a throughbore 245 for receiving the shaft 232 and/or tubing 270 therein. The annular portion 244 includes a plurality of relatively narrow gaps or slots 243 extending axially from the base portion 246, thereby dividing the annular portion 244 into fingers. In addition, the annular portion 244 includes one or more annular recesses or grooves 241 disposed within the throughbore 245. For example, each finger may include a recess 241, which may be shaped to receive a corresponding tab 221 on the mating disc 228.

As shown, the base portion 246 includes an outer shape substantially similar to the outer shell 210, e.g., to define an outer housing for the assembly 200. In contrast, the annular portion 244 has a relatively smaller outer diameter or cross-section, e.g., similar to that of the mating disc 228. As best seen in FIGS. 11C and 12C, the annular portion 244 may be sized to be received in the distal throughbore 218 of the outer shell 210, as described further below.

The slots 234 are sized and/or shaped to received the teeth 225 on the covering body 220 and/or the extensions 235b on the camming features 235. For example, during assembly, the teeth 225 on the mating disc 228 may be received in respective slots 243 while the tabs 221 are received within the throughbore 245 of the annular portion 244, e.g., such that the tabs 221 are received in and/or otherwise engage the recesses 241, e.g., to substantially permanently attach the covering body 220 to the backing member 240. It will be appreciated that other mating connectors (not shown) may be provided on the covering body 220 (e.g., on the mating disc 228) and/or on the backing member 240 (e.g., on the annular portion 244) to substantially permanently or removably attach the covering body 220 to the backing member 240. In addition or alternatively, the covering body 220 may be attached to the backing member 240 by bonding with adhesive, sonic welding, fusing, and the like.

Turning to FIG. 10B, the camming element 260 includes a plurality of spokes 261 extending from a central hub 262 including a passage 263 therethrough. The passage 263 has a diameter larger than the conduit 232 of the shaft 230, e.g., to allow the conduit 232 to be slidable through the camming element 260. The spacing and configuration of the spokes 261 may correspond to the slots 243 in the backing member 240, e.g., such that spokes 261 may be slidably received in the slots 243, thereby allowing the camming element 260 to slide axially relative to the backing member 240.

In addition, the spokes 261 may be sufficiently long such that, when the camming element 260 is inserted into the distal end 213 of the outer shell 210, the spokes 261 may be snapped, captured, or otherwise received in the annular recess 217 such that camming element 260 is substantially fixed axially within the outer shell 210. The outer diameter defined by the spokes 261 may be slightly smaller than the annular recess 217, thereby allowing the camming element 260 and outer shell 210 to rotate relative to each other. The width of the spokes 261 may also substantially match or be slightly narrower than the height of the annular recess 217 in the outer shell 210.

FIGS. 11A-12D show the assembly 200, including the outer shell 210, covering body 220, shaft 230, backing member 240, elastic member 250, and camming element 260 assembled together, in a deactuated or closed (no-flow) position (FIGS. 11A-11D) and an actuated or open (flow) position.

Before use, as shown in FIGS. 7A-7C, the components of the assembly 200 may be assembled together, e.g., during manufacturing. Although exemplary methods are described herein, it will be appreciated that the order of the various stages or steps and/or the particular steps used may be changed, as desired, e.g., based upon manufacturing convenience and/or other factors. With additional reference to FIG. 9B, the elastic member 250 may be received around the shaft 230, e.g., around the conduit 232 above the mating member 234. The second end 250b of the elastic member 250 may be received in the hole 231, thereby preventing subsequent rotation of the elastic member 250 relative to the shaft 230.

The proximal end 232a of the shaft 230 may be inserted into the covering body 220, e.g., into the throughbore 223 through the mating disc 228 until the fluid cap 236 is received within the opening 229a of the deformable membrane 229, as best seen in FIG. 7A. During this stage, the mating member 234 of the shaft 230 may be spaced apart from the mating disc 228 of the covering body 220, e.g., such that the elastic member 250 is spaced away from the mating disc 228. Alternatively, the relative length of the male boss 227 and conduit 232 may be such that the mating member 234 contacts or is received within the mating disc 228 (not shown). In this alternative, the covering body 220 may include an internal axial slot or peripheral hole (not shown) for receiving the first end 250a of the elastic member 250. This configuration may allow the shaft 230 to rotate within the covering body 220 yet the elastic member 250 may bias the shaft 230 to return to a desired rotational position (e.g., where the assembly 200 is closed, as explained elsewhere herein).

The covering body 220 (with the shaft 230 therein) may be inserted into the outer shell 210, e.g., into the distal throughbore 218 until the male boss 227 enters the proximal throughbore 216 and/or the mating disc 228 abuts the abutment surface at the intermediate location 219. The camming element 260 may be inserted over and around the distal end 232b of the shaft 230 and into the distal throughbore 218 of the outer shell 210, e.g., until the spokes 261 snap into or are otherwise captured or received within the annular recess 217.

The backing member 240 may be inserted into the distal end 213 of the outer shell 210, e.g., around the shaft 230 and camming element 260. This may involve aligning the slots 233 in the annular portion 244 of the backing member 240 with the spokes 261 on the camming element 260. The backing member 240 may be advanced until the annular portion 244 is connected to the mating disc 228 on the covering body 220. This connection may also require rotating the backing member 240 to ensure that the teeth 225 on the mating disc 228 are aligned with the slots 243 on the annular portion 244 and the tabs 221 enter the throughbore 245 of the annular portion 244, e.g., to engage the tabs 221 with the recesses 241.

If the assembly 200 is to be connected to tubing 170 (or another container or device, not shown), the end 172 of the tubing 170 may be connected to a connector on the distal end 232b of the shaft 230.

In an alternative procedure, the camming element 260 may be inserted into the throughbore 245 of the annular portion 244 of the backing member 240, i.e., after aligning the spokes 261 with the slots 243. The covering body 220, with the shaft 230 and elastic member 250 therein, may then be attached to the annular portion 244, e.g., by aligning the teeth 255, tabs 221, slots 243 and recesses 241, as described elsewhere herein. During this step, the first end 250a of the elastic member 250 may be received in one of the slots 243 in the annular portion 244. The outer shell 210 may then be received over this subassembly, e.g., by inserting the male boss 227 into the distal throughbore 218 of the outer shell 210 until the camming element 260 is captured in the annular recess 217.

During use, the assembly 200 may be provided as shown in FIGS. 7A and 11A-11D. In this condition, a fluid path through the assembly 200 may be biased to a closed position, e.g., with the shaft 230 in a rotational position such that the fluid cap 236 is aligned with and received in the opening 229a of the deformable membrane 229, as best seen in FIG. 7A. The outer shell 210 may be freely rotated relative to the backing member 240 and the internal components of the assembly 200. This may facilitate rotating the outer shell 210 to attach the assembly 200 to a fluid line or other device (not shown).

The outer shell 210 may also be free to move axially, although the axial movement is limited by the movement of the camming element 260 axially within the annular portion 244 of the backing member 240. For example, the outer shell 210 may be directed distally until the camming member 260 and/or outer shell 210 contacts the base portion 246. In this distal position, the male boss 227 may extend to and/or partially out of the proximal end 215 of the outer shell 210, e.g., similar to a conventional male Luer connector. This position may facilitate cleaning the male boss 227, fluid cap 236, and/or deformable membrane 229, e.g., during use. In addition, the outer shell 210 may be directed proximally away from the base portion 246 of the backing member 240 until the camming element 260 contacts the cam features 235 on the mating member 234 of the shaft 230.

Figure 11A:
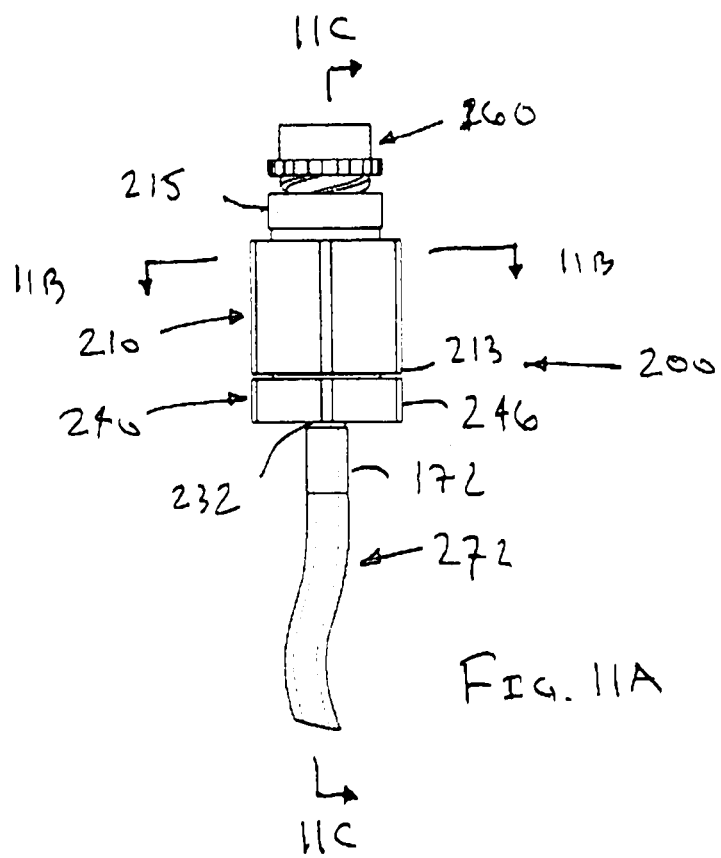
FIG. 11A is a side view of the assembly of FIGS. 7A-7C in a deactuated condition before a Luer fitting has been connected to the assembly.
Figure 11C:
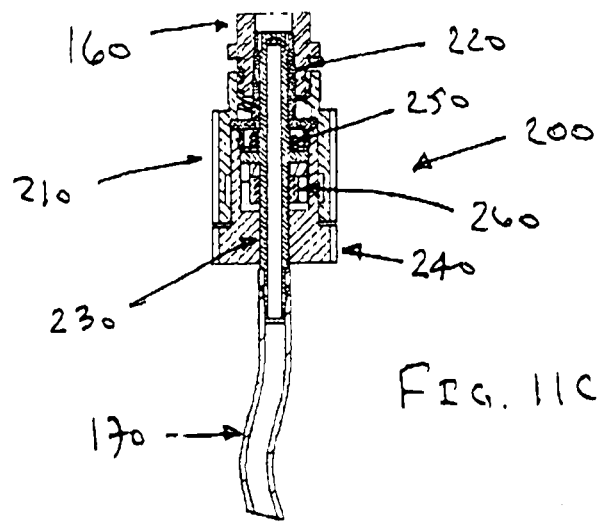

Turning to FIG. 11A, a female Luer 160 is shown, which includes an external Luer thread that is partially inserted into the proximal end 215 of the outer shell 210. In this position, the outer shell 210 may remain movable axially some distance relative to the backing member 240.

Turning to FIGS. 12A-12D, as a female Luer connector 160 is fully threaded into the outer shell 210, it pushes the male boss 227 toward the distal end 213 of the outer shell 210. This causes the covering body 220 and shaft 230 to move toward the distal end 213 of the outer shell 210. Stated differently, as the female Luer 160 is threaded into the proximal end 215 of the outer shell 210, the outer shell 210 may be pulled proximally away from the male boss 227 and the base portion 246 of the backing member 240, thereby moving the camming element 260 away from the base portion 246 and towards the mating member 234 on the shaft 230.

This causes the camming element 260 to contact the cam features 235 on the shaft 230, i.e., the cam features 235 are pushed against the spokes 261 of the camming element 260, which causes the shaft 230 to rotate. The angle of each hypotenuse and size of cam features 235 may be such that, when the shaft 230 is rotated to the point where the spokes 261 bottom out and abut vertical walls 235c adjacent the cam features 235. In this position, the fluid cap 236 is mismatched with the deformable membrane 229, i.e., the fluid cap 236 has rotated relative to the opening 229a to create gaps 229b between the fluid cap 236 and the deformable membrane 229. The gaps 229b open a fluid path between the throughbore 233 in the shaft 230 and the proximal throughbore 216 of the outer shell 210, i.e., into the Luer fitting 160 attached to the assembly 200. Thus, the fluid path may be opened substantially simultaneously with threading the female Luer connector 160 into the assembly 200.

For example, the fluid cap 236 may be substantially evenly mismatched with the deformable membrane 229, i.e., such that each of the points of the fluid cap 236 are in substantially the midpoint of the sides of the opening 229a in the deformable membrane 229. As shown in FIGS. 11B and 12B, for example, using hexagonally shaped members, there are six equal substantially triangular gaps 229b formed between the fluid cap 236 and the deformable membrane 229 when the assembly 200 is in the actuated state, i.e., because each point of the hexagonally shaped fluid cap 236 is situated on the midpoint of the sides of the hexagonally shaped opening 229a in the deformable membrane 229. Although other degrees of deformation may work, the described deformation of the deformable membrane may maximize the rate of fluid flow.

In addition, when the female Luer connector 160 is tightened into the proximal end 215 of the outer shell 210, a region 226 of the annular portion 244 of the backing member 240 may become exposed. If desired, an actuated status indicator 226 may be provided on the annular portion 244, as shown in FIG. 12A, which may become exposed only when the female Luer connector 160 is finally tightened to the outer shell 210. The status indicator 226 may include a color (such as green), one or more words, and the like, similar to other embodiments herein, which may provide the user visual confirmation that the assembly 200 has achieved the actuated position in which the flow path is open. Optionally, the region between the actuated status indicator 226 and the base portion 240 may include another status indicator (not shown), such as a contrasting color (e.g., red), which may provide a visual indication to the user that the assembly 200 has not yet been actuated.

Turning to FIGS. 13A-16B, yet another exemplary embodiment of a valve/connector assembly 300 is shown that includes the same general components as the assembly 200. Since the corresponding structures of the assembly 300 function in the same manner as described above for the assemblies 100, 200, like components have been similarly numbered (except preceded by 300, rather than 100 or 200. As best seen in FIGS. 14A and 14B, the assembly 300 includes an outer shell 310 with a female Luer thread 314, a covering body or inner housing 320 with a deformable membrane 329, a shaft or core pin 330 with an elastic member, i.e., spring 350, and a backing member 340, generally similar to the apparatus 200. The outer shell 310 is structurally distinct from the outer shell 210 in assembly 200, and includes a proximal throughbore 316, an unthreaded portion 315, a tapered portion 317, a distal throughbore 318, and a female Luer thread 314.

Generally, the components, assembly, use, and operation of the assembly 300 is similar to the previous embodiments. Unlike the previous embodiments, however, the outer shell 300 includes a female Luer connector and thread 314 for mating with a male Luer connector 160' (shown in FIGS. 15A and 15B), e.g., communicating with a fluid line or other device (not shown).

Turning to FIGS. 17A-23C, still another exemplary embodiment of a valve/connector assembly 400 is shown that includes an outer shell 410, a covering body or inner housing 420, a shaft, core pin, or tubular member 430, a backing member 440, an elastic member 450, and a camming element 460. Generally, the components, assembly, use, and operation of the assembly 400 is similar to the previous embodiments.

Unlike the previous embodiments, the covering body 420 includes a closed cap including a plurality of openings 429 in the side thereof. In addition, the shaft 430 includes a closed proximal end 432a including a plurality of openings 437 in a side wall thereof. The elastic member 450 includes a compression member, such as one or more spring washers, which may bias the covering body 420 into the proximal end 415 of the outer shell 410. It will be appreciated that these versions of the covering body 420/shaft 430 or elastic member 450 may be utilized in other embodiments disclosed herein or may be replaced with similar components from the other embodiments herein.

In addition, the shaft 430 includes a distal end 432b that has a noncircular cross-section, e.g., a polygonal shape, similar to a passage through the elastic member 460. The camming element 460 includes one or more helical ridges that are shaped similar to helical grooves in the mating member 428 of the covering body 420. It will be appreciated that other mating helical features may be provided on or in the camming element 460 and covering body 420, e.g., to provide a camming mechanism that translates relative axial movement between the covering body 420 and the shaft 430 into rotational motion.

Turning to FIGS. 22A-22D, the assembly 400 is shown in the closed position in which the openings 437, 429 in the shaft 430 and covering body 420 are out of alignment with one another, thereby closing a fluid path between the throughbore in the shaft 430 and the proximal end 415 of the outer shell 410.

Turning to FIGS. 23A-23D, when a connector, e.g., a female Luer fitting 160, is connected to the proximal end 415 of the outer shell 410, the covering body 420 is directed distally towards the backing member 440. This causes the camming element 460 and, consequently, the shaft 430 to rotate relative to the covering body 420 due to the interaction of the helical camming features, thereby aligning the openings 437, 429 and opening the fluid path through the assembly 400.

Figure 23A:
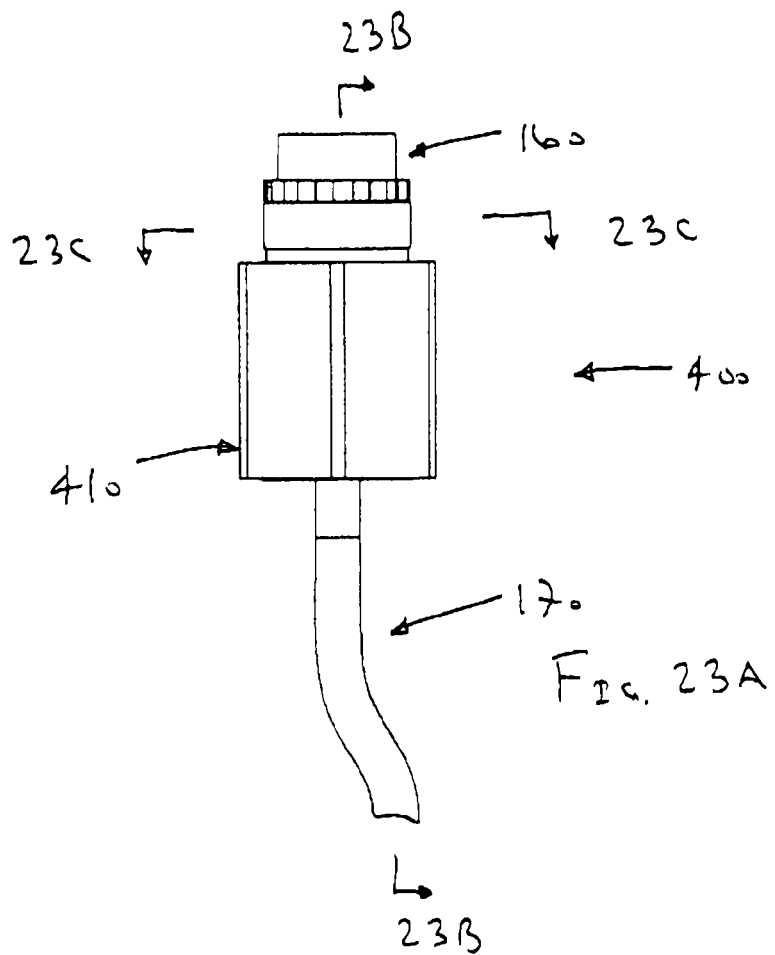
FIG. 23A is a side view of the assembly of FIGS. 17A-17C in an actuated condition after the Luer fitting has been connected to the assembly.
Figure 23D:
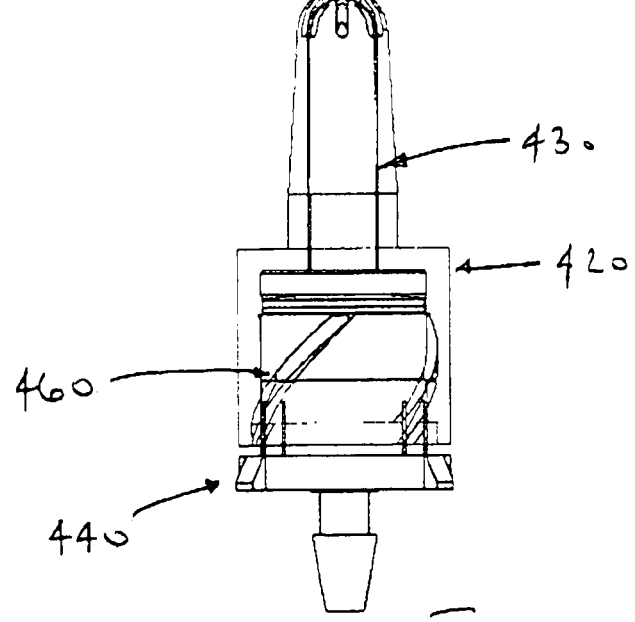
FIG. 23D is a side view of the assembly of FIG. 23A with the outer shell removed to show the position of the internal components of the assembly after actuation.
Figure 23B:
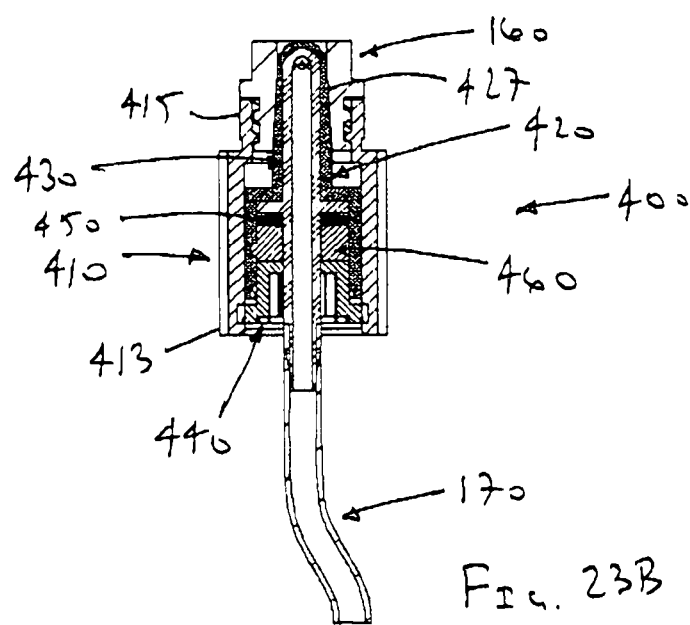
FIGS. 23B and 23C are cross-sectional views of the assembly of FIG. 23A, taken along lines 23B-23B and 23C-23C, respectively.
Figure 23C:
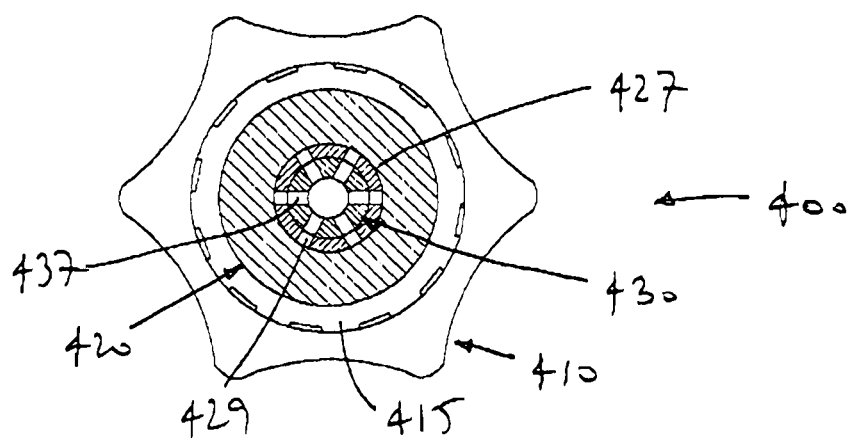

When the covering body 420 is directed distally, the elastic member 450 may be compressed, as shown in FIG. 23B. When the connector 160 is disconnected from the assembly 410, the elastic member 450 may resiliently expand, thereby biasing the covering body 420 to move proximally away from the backing member 440, and causing the shaft 430 to rotate to automatically close the fluid path through the assembly 400. Thus, unlike the previous embodiments, the fluid path may not be opened until immediately before threading is completed. Stated differently, the female Luer fitting 160 may become engaged with the proximal end 415 before the assembly 400 is actuated, i.e., before the fluid path is opened. After use, when the assembly 400 is being disengaged from the female Luer fitting 160, the assembly 400 may become deactuated, i.e., the fluid path may be closed, immediately upon beginning disengagement, thereby reducing the risk of fluid leakage from the assembly 400.

Figure 24A:
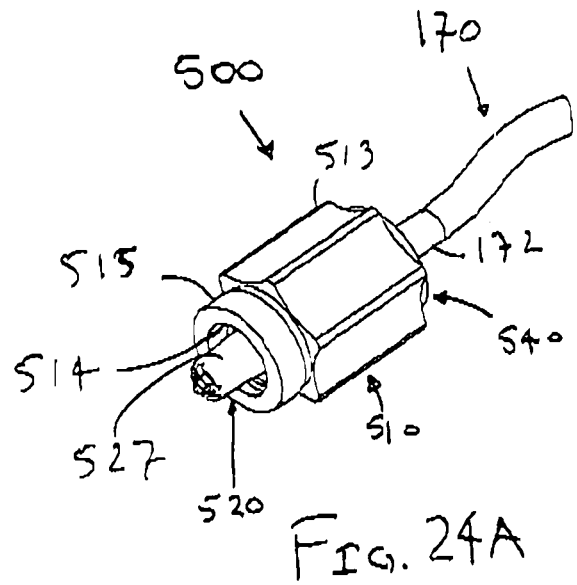
FIG. 24A is a perspective view of yet another embodiment of a connecting assembly including an outer shell with a male Luer thread connected to a distal end of a length of tubing.

Turning to FIGS. 24A-32B, yet another exemplary embodiment of a valve/connector assembly 500 is shown that includes the same general components as the previous assemblies. As best seen in FIGS. 24A-24C, the assembly 500 includes an outer shell or bezel 510 with a male Luer thread 514, a covering body or inner housing 520, a shaft or core pin 530, a spring or other elastic member 550, and a backing member 540.

Figure 25:
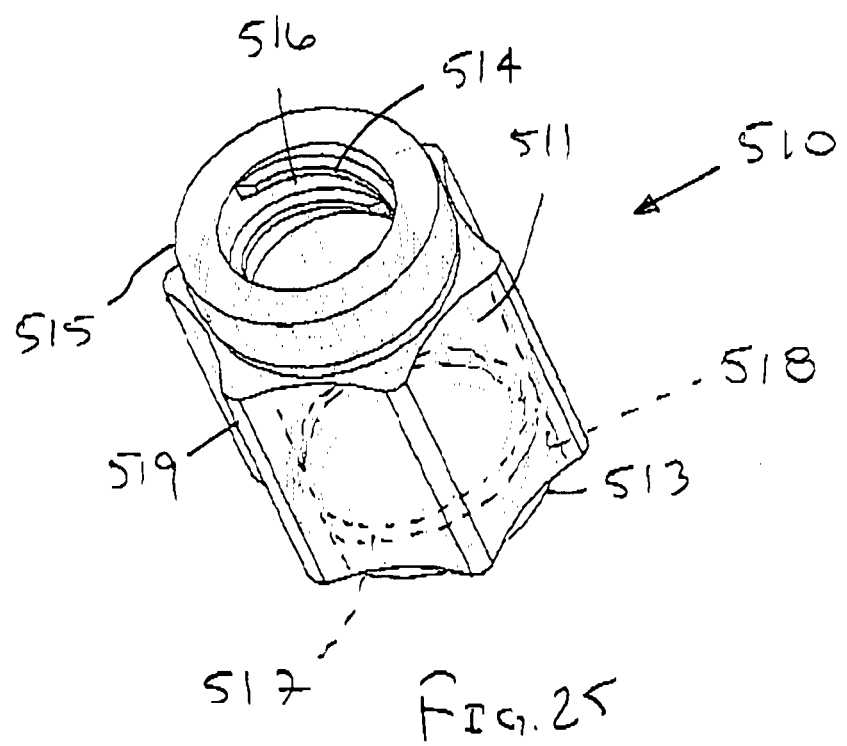
FIG. 25 is a perspective view of the outer shell of the assembly of FIGS. 24A-C.

With particular reference to FIG. 25, the outer shell 510 includes proximal and distal ends 515, 513, a distal throughbore 518 having an annular recess 517 therein, and a proximal throughbore 516 including the male Luer thread 514 therein adjacent the proximal end 515. As shown, the outer shell 510 has a hexagonal shaped outer surface 511, although, alternatively, the outer surface may have any other shape, similar to the previous embodiments. For example, the outer surface 511 may facilitate a user gripping and/or manipulating the outer shell 510, e.g., to engage and/or disengage the male Luer thread 514 with a female Luer connector from a fluid line or other device (not shown).

The distal throughbore 518 extends from the distal end 513 of the outer shell 510 to intermediate location 519. The length, size, and/or shape of the distal throughbore 518 is sufficient to accommodate at least a portion of the inner housing 520 and shaft 530 therein (not shown, see FIGS. 24A-24C). The diameter or other cross-section of the distal throughbore 518 may be larger than the proximal throughbore 516, e.g., to provide an abutment surface at the intermediate location 519 for limiting proximal movement of the covering body 520 into the distal throughbore 518, as explained further below.

The annular recess 517 may be disposed between the abutment surface at the intermediate location 519 and the distal end 513, e.g., closer to and/or immediately adjacent the distal end 513. The annular recess 517 may have a slightly larger diameter than the rest of the distal throughbore 518, e.g., having a height and diameter substantially similar to tabs 548 on the backing member 540, e.g., to couple the outer housing 510 to the backing member 540. Thus, as described further below, the outer housing 510 may be substantially fixed axially relative to the backing member 540, but may rotate freely relative to the backing member 540.

The dimensions of the proximal throughbore 516 and male Luer thread 514 may be provided according to ISO standards for Luer connectors. Alternatively, other connectors (not shown) may be provided on the proximal end 515, if desired, similar to the previous embodiments.

Figure 26A:
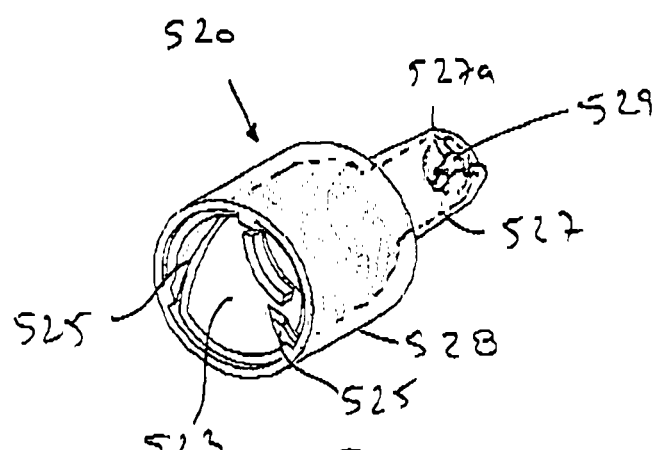
FIGS. 26A and 26B are perspective views of the covering body of the assembly of FIGS. 24A-24C.
Figure 26B:
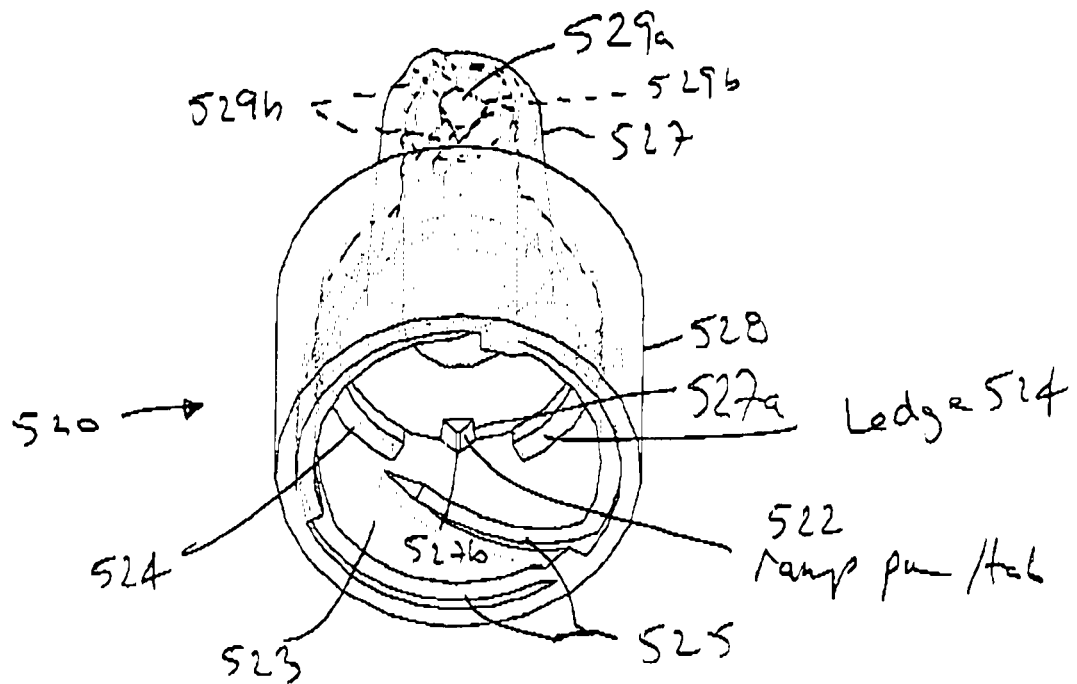

Turning to FIGS. 26A and 26B, the inner housing 520 generally includes an elongated male boss 527, a throughbore 523, and an enlarged mating portion 528. The male boss 527 may be dimensioned per ISO industry standards, e.g., having a cylindrical shape with a tapered proximal end. The male boss 527 and mating portion 528 of the inner housing 520 may be integrally molded or otherwise formed from a single piece or may be separate pieces substantially permanently attached to one another. The throughbore 523 runs the entire length of inner housing 520, e.g., through the mating portion 528 and the male boss 527, e.g., all similar to the previous embodiments.

Figure 24B:
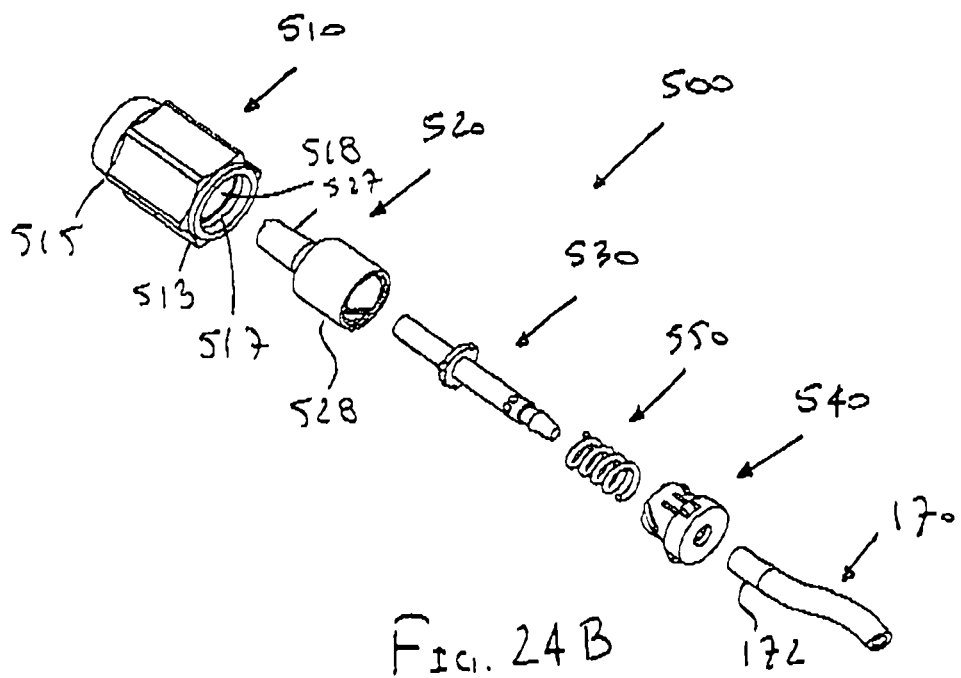
FIGS. 24B and 24C are exploded views of the assembly of FIG. 24A, including an outer shell with a proximal throughbore containing a Luer thread and a distal throughbore; a covering body including a male boss with openings and an outer mating surface; a shaft with an elastic member and a mating member; and a backing member.
Figure 24C:
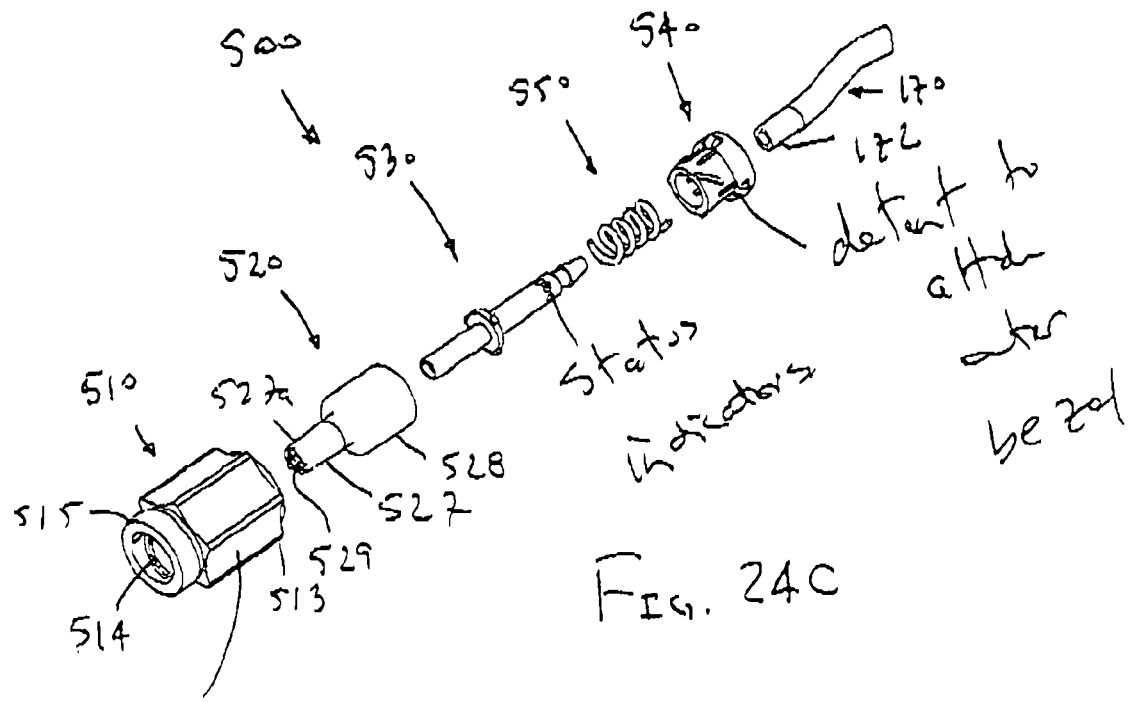

Also similar to the previous embodiments, the inner housing 520 may be received within the outer shell 510, e.g., by inserting the male boss 527 through the distal throughbore 518 into the proximal throughbore 516, as shown in FIGS. 24B and 24C. When the male boss 527 is received in the proximal throughbore 516, the mating portion 528 may be received in the distal throughbore 518, e.g., contacting the abutment surface at the intermediate location 519 (see FIG. 29B), and the male boss 527 may extend concentrically within the male Luer thread 514.

The mating portion 528 may have a diameter that substantially matches that of the distal throughbore 518, e.g., such that the mating portion 528 may rotate freely within the distal throughbore 518 without substantial lateral movement. In addition, one or more helical threads, grooves, or ridges 525 may be molded, machined, or otherwise provided along the throughbore 523 within the mating portion 528. The helical ridges 525 may correspond to similar helical ridges or grooves 545 on the backing member 540, as described further below. It will be appreciated that other ridges, grooves, and/or other features (not shown) may be provided on the mating portion 528 and the backing member 540, i.e., to provide cooperating helical features between the mating portion 528 and the backing member 540. In addition or alternatively, any number of cooperating threads or features, e.g., one or more, may be provided on the mating portion 528 and backing member 540 to allow the mating portion 528 to move helically relative to the backing member 540, as described further below.

In addition, as best seen in FIGS. 26B, 29C, 31B, and 32B, the mating portion 528 includes one or more partial circumferential ledges 524 disposed between the helical ridges 525 and the male boss 527. For example, the mating portion 528 may include three circumferential ledges 524 extending partially around the inside surface of the mating portion 528 that are spaced apart from one another, e.g., each ledge 524 extending less than a third the distance around the circumference.

Figure 31A:
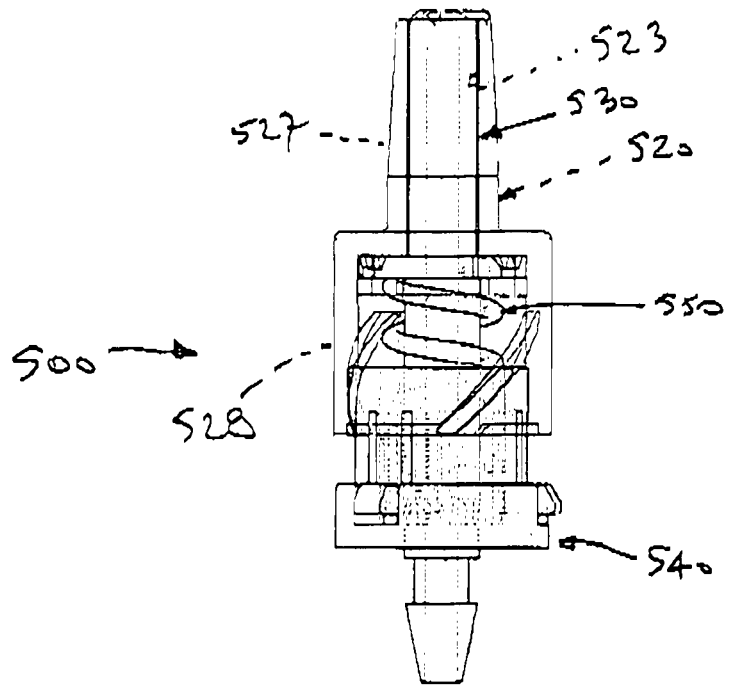
FIGS. 31A and 31B are side and perspective views, respectively, of the assembly of FIG. 29A with the outer shell removed to show the position of the internal components of the assembly before actuation.
Figure 31B:
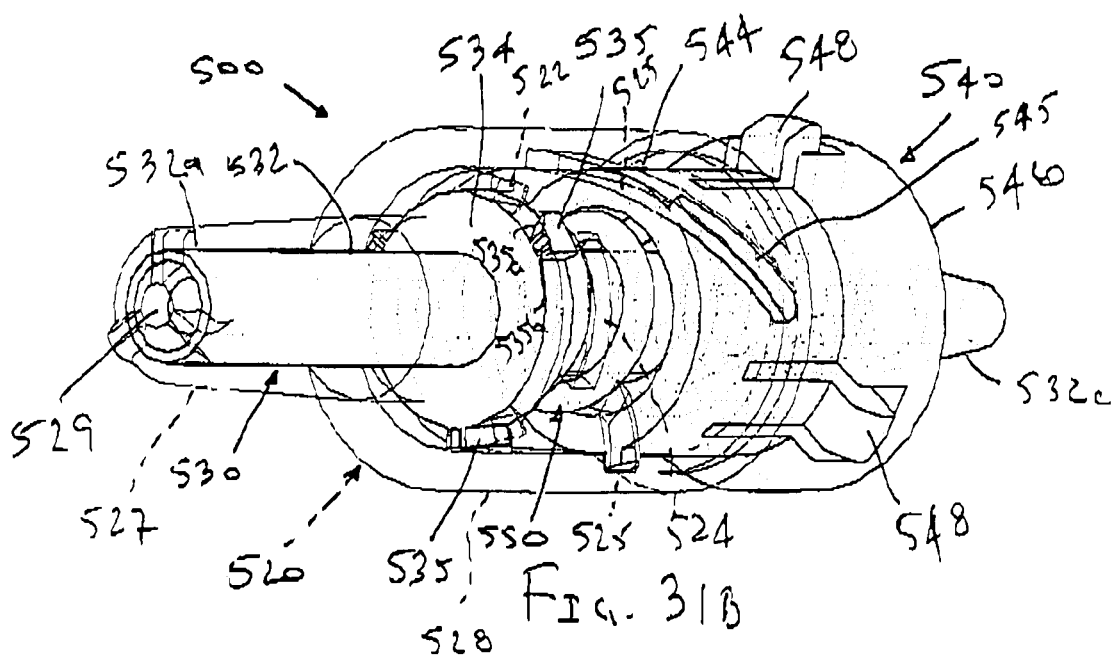
Figure 32B:
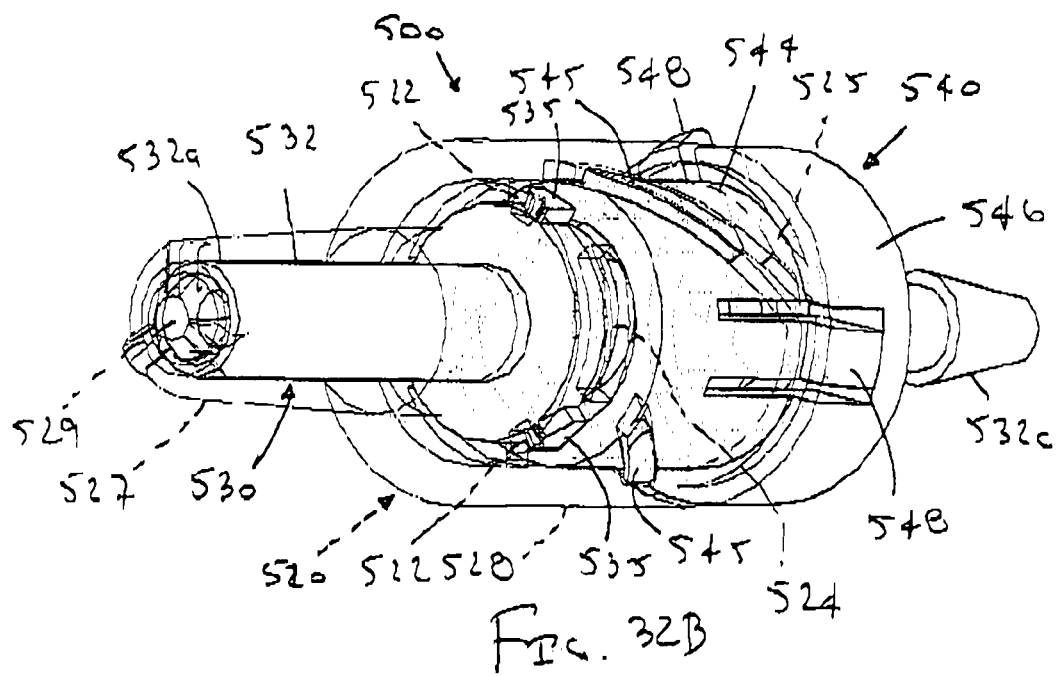

As best seen in FIGS. 26B, 31B, and 32B, in the gap between adjacent circumferential ledges 524, the mating portion 528 may include ramped tabs or ledges 522. Each ramped tab 522 includes a ramped surface 522a extending distally towards the helical ridges 525 and ending in a blunt distal surface 522b. The ramped tabs 522 may be offset axially, e.g., proximally, from the circumferential ledges 524, as explained further below.

Figure 29A:
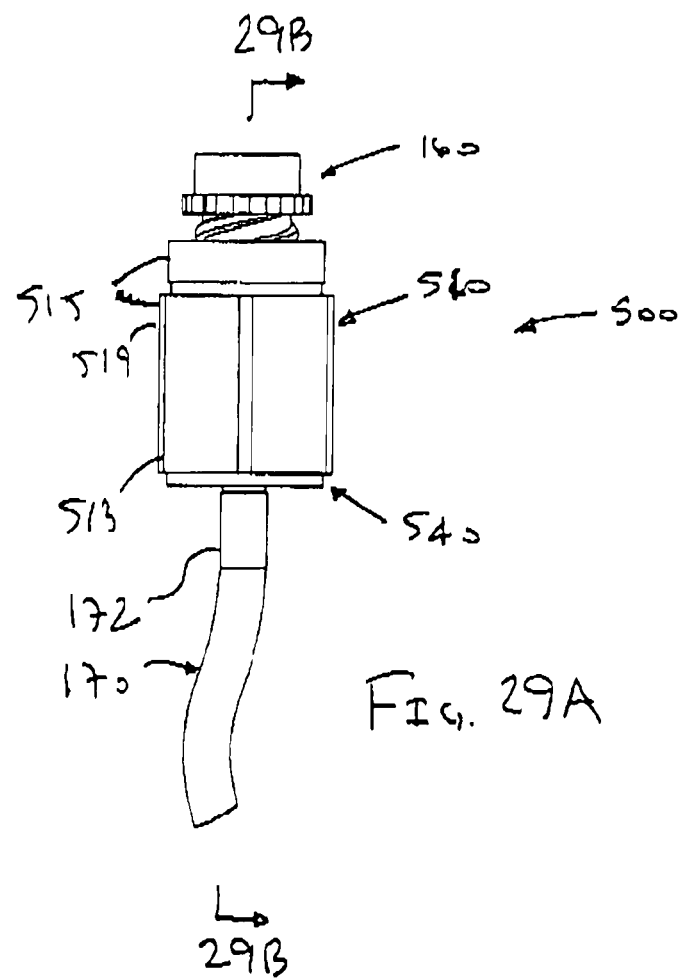
FIG. 29A is a side view of the assembly of FIGS. 24A-24C in a deactuated condition before a Luer fitting has been connected to the assembly.
Figure 29C:
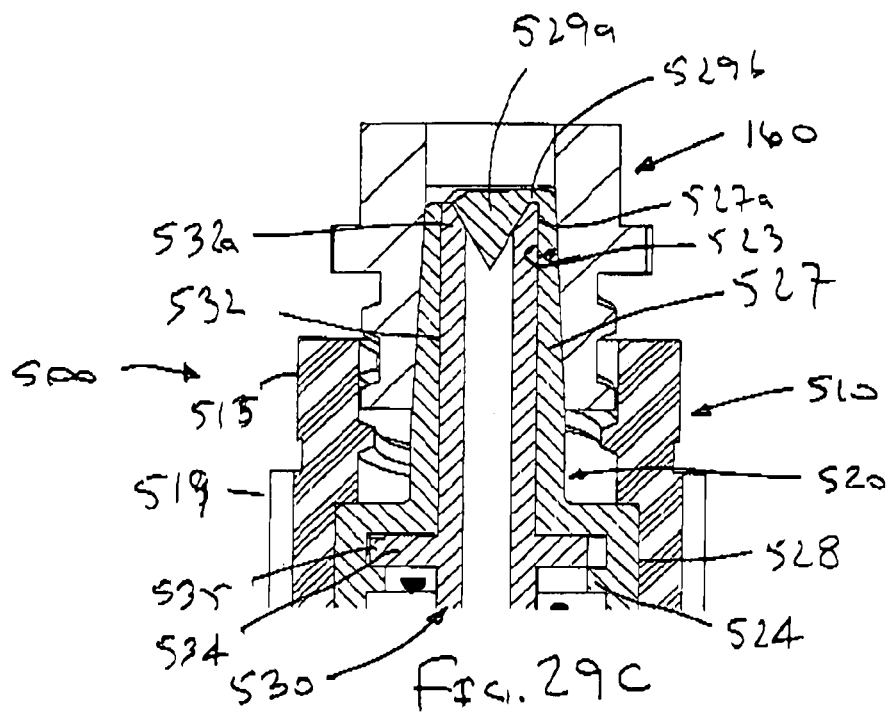

The male boss 527 may include a seal 529 disposed within the throughbore 523, e.g., at the proximal end 527a of the male boss 527 for selectively sealing the assembly 500, as described further below. For example, as shown in FIGS. 26B and 29C, the seal 529 may include a central sealing pin 529a supported by one or more supports 529b extending radially inwardly from the proximal end 527a of the male boss 527. As shown, three supports 529b may be disposed radially around the sealing pin 529a, thereby defining three openings 529c through which fluid may flow, as described further below. The sealing pin 529a may have a conical shape, as shown, or, alternatively, a frusto-conical or other shape (not shown) for sealing a throughbore 533 through the shaft 530, as described further below.

Figure 27A:
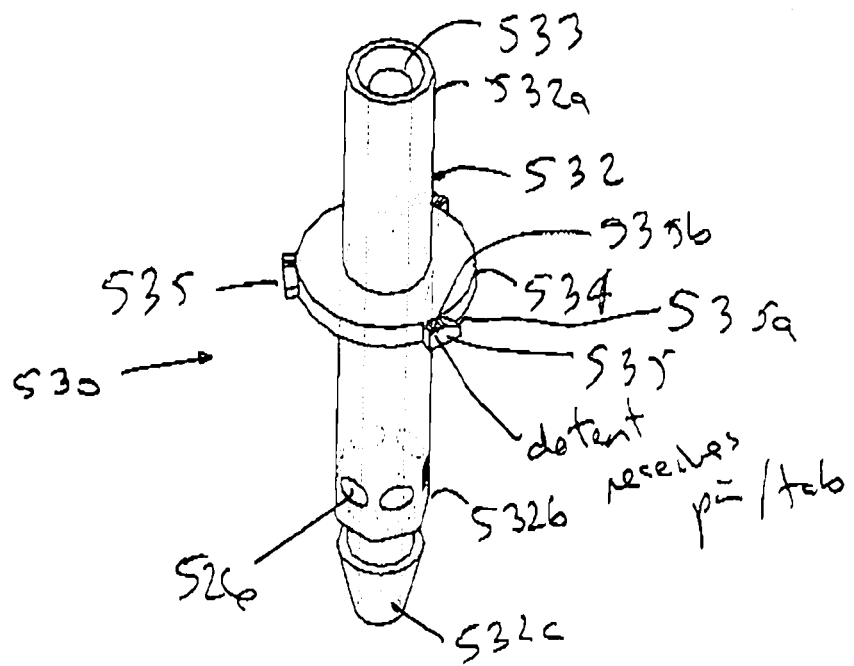
FIGS. 27A and 27B are perspective views of the shaft of the assembly of FIGS. 24A-24C.
Figure 27B:
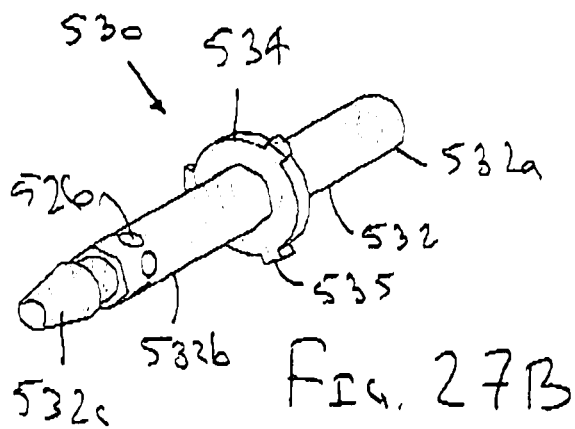

Turning to FIGS. 27A and 27B, the shaft 530 generally includes a conduit 532, the throughbore 533 extending between first and second ends 532a, 532b of the conduit 532, and a mating member 534 with a plurality of cam features 535. The mating member 534 may be located near the midpoint of the conduit 532. For example, the mating member 534 may be located along a length of the conduit 532 such that, when the shaft 530 is inserted into the inner housing 520, the mating member 534 is disposed proximal to the circumferential ledges 524 on the inner housing 520, i.e., between the circumferential ledges 524 and the male boss 527, e.g., as shown in FIGS. 29B and 29C.

The cam features 535 may extend radially or otherwise from the mating member 534, and generally include proximal ramped surfaces 535a extending to blunt pockets 535b. The ramped surfaces 525a may be configured to contact and/or otherwise interact with the ramped tabs 522 on the inner housing 520, e.g., to effect actuation and/or deactuation of the assembly 500, as described elsewhere herein. Similar to the previous assemblies, the angle of ramped surfaces of the cam features 525 and ramped tabs 522 may be changed, e.g., to correspond to the selected configuration, e.g., number and/or orientation of circumferential ledges 524, ramped tabs 522, and cam features 535, for example, to maximize fluid flow upon actuation.

Optionally, as shown in FIGS. 27A and 29C, the proximal end 532a of the conduit 532 may have a tapered inner surface, e.g., corresponding to the shape of the sealing pin 529a. Thus, when the shaft 532 is fully received in the inner housing 520, e.g., such that the mating member 534 is disposed proximal to the circumference ledges 524, the proximal end 532a of the conduit 532 may abut and/or otherwise engage the sealing pin 529, thereby substantially sealing the throughbore 533 through the conduit 532. During use, the proximal end 532a of the conduit 532 may be directed away from the sealing pin 529a to open the throughbore 533, as described further below.

Figure 30B:
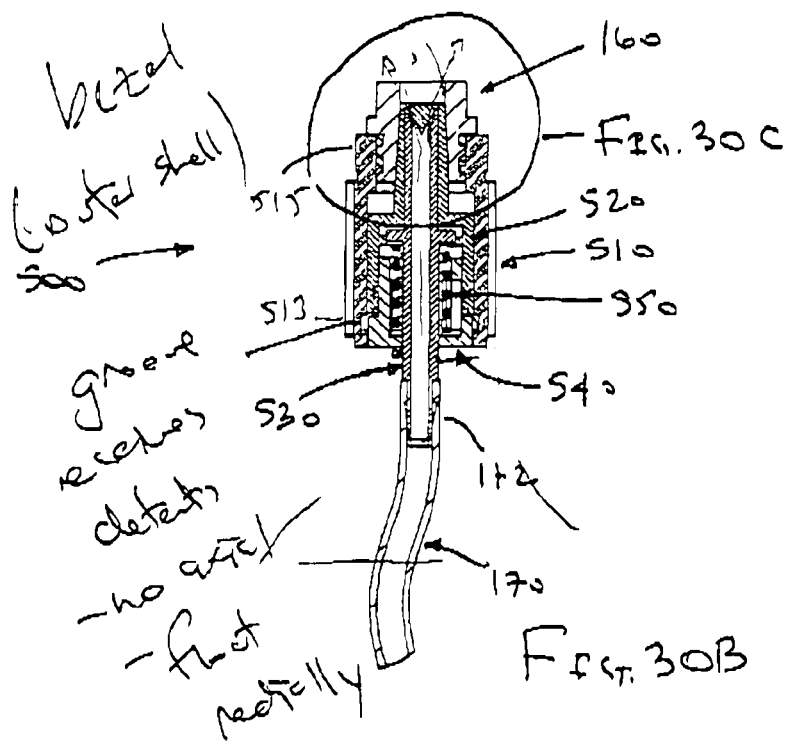
FIGS. 30B and 30C are cross-sectional views of the assembly of FIG. 30A, taken along lines 30B-30B.

As best seen in FIG. 27B, the distal end 532b of the conduit 532 may have a noncircular cross-section, e.g., a hexagonal or other polygonal shape. In addition, the distal end 532b may include one or more visual indicators 526, e.g., for indicating when the assembly 500 is actuated (and/or deactuated), similar to previous embodiments and/or as described further below. In addition or alternatively, the distal end 532b may include a nipple or other connector 532c, e.g., for connecting the assembly to tubing or other fluid line 170, as shown in FIGS. 29B and 30B.

Figure 28A:
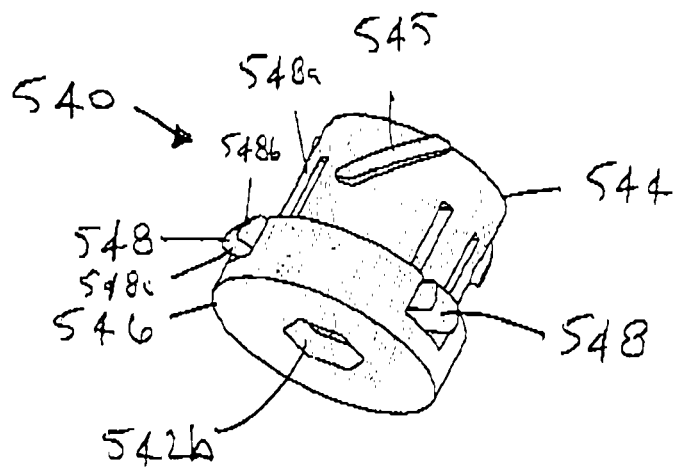
FIGS. 28A and 28B are perspective views of the backing member of the assembly of FIGS. 24A-24C.
Figure 28C:
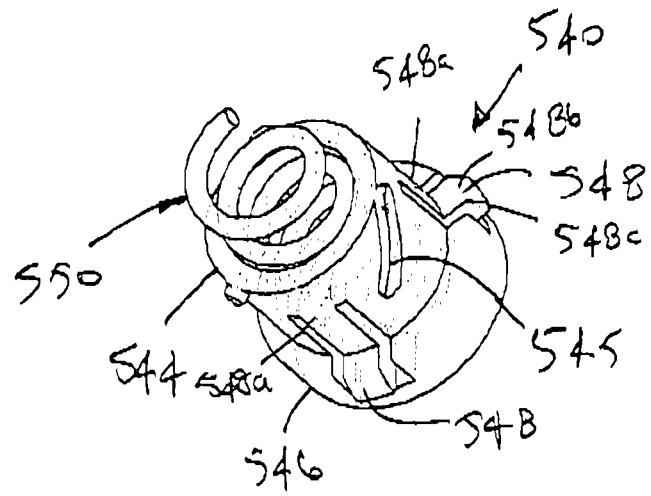
FIG. 28C is a perspective view of the backing member of FIGS. 28A and 28B, also showing the elastic member of the assembly of FIGS. 24A-24C.
Figure 28B:
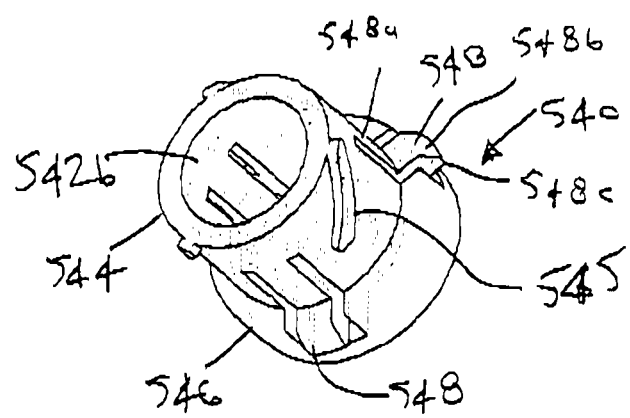

Turning to FIGS. 28A-28C, the backing member 540 includes a relatively wide base portion 546, and a relatively narrow annular portion 544 extending proximally from the base portion 546, together defining a throughbore 542. The throughbore 542 may include a relatively large proximal passage 542a through the annular portion 544 (best seen in FIG. 28B) and a relatively narrow distal passage 542b through the base portion 546 (best seen in FIG. 28C). The distal passage 542b may have a noncircular, e.g., hexagonal or other polygonal, shape similar to the distal end 532b of the conduit 532 such that the conduit 532 may be free to pass axially through the distal passage 542b without rotating relative to the backing member 540.

The backing member 540 also includes one or more helical ridges and/or grooves 545, e.g., extending helically along an outer surface of the annular portion 544, e.g., for cooperating with the helical ridges 525 on the inner housing 520, as described further below. In addition, the backing member 540 may includes one or more tabs or other connectors 548, e.g., for coupling the backing member 540 to the outer shell 510. As best seen in FIGS. 28A-28C, the tabs 548 may include cantilever elements having one end 548a fixed to the backing member 540, e.g., to the annular portion 544, and radial elements including ramped proximal edges 548b and blunt distal edges 548c.

During assembly, the tabs 548 may be deflected radially inwardly. e.g., to define a size no larger than the annular portion 544, yet biased outwardly to define a size larger than the base portion 546. The annular portion 544 may have a diameter or other cross-section such that the annular portion 544 may be received within the distal throughbore 518 in the outer shell 510, as described further below.

Also shown in FIG. 28C, the proximal passage 542b may be sized to receive the elastic member 550 therein. The elastic member 550 may be a compression spring having a diameter smaller than the proximal passage 542b but larger than the distal passage 542a such that a first or distal end of the spring 550 abuts the base portion 546 of the backing member 540 when the spring 550 is inserted into the proximal passage 542b. The inner diameter of the spring 550 may be sized to be received around the conduit 532 of the shaft 530, as shown in FIGS. 29B, 30B, 31A, and 32A. As best seen in FIGS. 31A and 32A, a second or proximal end of the spring 550 may be smaller than the mating member 534 of the shaft 530 such that the proximal end of the spring 550 abuts and/or pushes against the mating member 534. Thus, the spring 550 may bias the shaft 530 away from the backing member 540, as described further below.

With reference to FIGS. 24A-24C, during manufacturing, the components of the assembly 500 may be formed and assembled together. Although exemplary methods are described herein, it will be appreciated that the order of the various stages or steps and/or the particular steps used may be changed, as desired, e.g., based upon manufacturing convenience and/or other factors. For example, the outer shell 510, inner housing 520, shaft 530, and backing member 550 may be molded, machined, or otherwise formed separately from one another, e.g., from plastic, metal, or composite material, similar to the previous embodiments.

The spring 550 may be received around the shaft 530, e.g., inserted over the distal end 532b of the conduit 532. The distal end 532b of the conduit 532 may then be inserted into the annular portion 544 of the backing member 540, e.g., through the throughbore 542, which may require aligning the distal end 532b with the distal passage 542a. The spring 550 may then be received in the proximal passage 542b within the annular portion 544 of the backing member 540. Thereafter, the shaft 530 may be movable axially relative to the backing member 540 but rotationally fixed relative to one another. For example, the shaft 530 may be directed distally into the backing member 540 with the spring 550 biasing the shaft 530 to return proximally away from the backing member 540.

Before or after inserting the shaft 530 through the backing member 540, the proximal end 532a of the shaft 530 may be inserted into the inner housing 520. For example, the proximal end 532a may be inserted into the throughbore 523 through the mating portion 528 until the mating member 534 passes the circumferential ledges 524. This may require aligning the ramped tabs 535 with the gaps between the circumferential ledges 524 to and twisting the shaft 530 to pass the cam features 535 between the tabs 522 and the ledges 524. Once the shaft 530 is fully seated in the inner housing 520, the proximal end 532a of the conduit 532 may engage the seal 529 on the male boss 527 of the inner housing 520, thereby substantially sealing the throughbore 533 of the conduit 532 from fluid flow therethrough.

If the shaft 530 has already been received through the backing member 540, the helical ridges 525, 545 on the inner housing 520 and backing member 540 should be aligned before fully seating the shaft within the inner housing 520, i.e., to allow the inner housing 520 to move helically relative to the backing member 540. Similarly, if the backing member 540 is advanced over the distal end 532b of the shaft 530 after receiving the shaft 530 within the inner housing 520, the helical ridges 525, 545 should still be aligned during advancement.

The inner housing 520 (with the shaft 530 therein) may be inserted into the outer shell 510, e.g., into the distal throughbore 518 until the male boss 527 enters the proximal throughbore 516 and/or the mating portion 5 abuts the abutment surface at the intermediate location 519.

The backing member 540 may then be connected to the outer shell 510, e.g., to capture the inner housing 520, shaft 530, and spring 550 within the outer shell 510. For example, the annular portion 544 of the backing member 540 may be inserted into the distal throughbore 518 of the outer shell 510 until the tabs 548 contact the distal end 513 of the outer shell 510. Further insertion of the backing member 540 causes the ramped surfaces 548b of the tabs 548 to contact the distal end 513, thereby directing the tabs 548 inwardly and allowing the tabs 548 to enter the distal throughbore 518. Once the tabs 548 reach the annular recess 517, the tabs 548 may be free to return radially outwardly and enter the annular recess 517. The blunt distal edges 548c prevent the backing member 540 form being disconnected from the outer shell 510. Thus, the outer shell 510 and backing member 540 may be fixed axially relative to one another, yet the outer shell 510 may be free to rotate relative to the backing member 540, e.g., such that the tabs 548 slide circumferentially within the annular recess 517.

If the assembly 500 is to be connected to tubing 170 (or another container or device, not shown), the end 172 of the tubing 170 may be connected to the connector 532c on the distal end 532b of the shaft 530, e.g., as shown in FIGS. 29B and 30B.

During use, the assembly 500 may be provided as shown in FIGS. 29A-29C and 31A-31B. In this condition, the assembly 500 may be in a closed position, e.g., with the shaft 530 in an axial position such that the proximal end 532a of the conduit 532 is substantially sealed by the seal 529 on the inner housing 520, e.g., as best seen in FIG. 29C. The outer shell 510 may freely rotate relative to the backing member 540 and the internal components of the assembly 500, e.g., the inner housing 520 and shaft 530. This may facilitate rotating the outer shell 510 to attach the assembly 500 to a fluid line or other device (not shown).

In the closed position, the mating member 534 of the shaft 530 is disposed between the circumferential ledges 524 and male boss 527 on the inner housing 520, as best seen in FIGS. 29C and 31B, thereby coupling axial movement of the shaft 530 to the inner housing 520. Thus, if the inner housing 520 is directed axially relative to the outer shell 510, the shaft 530 is also initially directed axially.

Turning to FIGS. 30A-30C and 31A-31B, a female Luer 160 is shown fully threaded into the outer shell 510. When the female Luer 160 is initially threaded into the outer shell 510, the female Luer 160 may contact the male boss 527 on the inner housing 520. Once the female Luer 160 is fully engaged with the male boss 527, further threading of the female Luer 160 causes the inner housing 520 to move distally relative to the outer shell 510 and the backing member 540. Because the inner housing 520 is coupled to the backing member 540 by helical threads 525, 545, distal movement of the inner housing 520 also causes the inner housing to rotate, i.e., move helically distally relative to the backing member 540. Because the shaft 530 is fixed rotationally relative to the backing member 540, this means that the inner housing 530 also rotates relative to the shaft 530, but also directs the shaft 530 distally relative to the backing member 540. Thus, during this initial movement, the proximal end 532a of the shaft 530 remains sealed by the seal 529 on the male boss 527.

With reference to FIGS. 31B and 32B, as the inner housing 520 rotates relative to the shaft 530, the ramped tabs 522 approach the cam features 535 and the cam features 535 slide along the circumferential ledges 524 towards the gaps between the adjacent ledges 524. In the final stage of threading the female Luer 160 into the outer shell 510, the ramped tabs 522 contact the cam features 535, i.e., the ramped surfaces 522, 535a slidably engage one another. This causes the shaft 530 to move distally relative to the inner housing 520 directing the cam features 535 into the gaps between the ledges 524. This causes the proximal end 532a of the shaft 530 to move distally away from the sealing pin 529a, as best seen in FIG. 30C, thereby opening the fluid path through the assembly 500, i.e., through the throughbore 533 of the shaft 530.

Once the tabs 522 pass over the cam features 535, the blunt distal surfaces 522b of the ramped tabs 522 enter the pockets 535b, thereby locking the assembly 500 in the open position. In addition or alternatively, the cam features 535 may abut the sides of the circumferential ledges 524, thereby preventing further rotational motion of the inner housing 520 relative to the shaft 530. At this point, the female Luer 160 is fully threaded into the outer shell 510. Thus, unlike previous embodiments, the fluid path through the assembly 500 may not be opened until the female Luer 160 is substantially fully threaded into the proximal end 515 of the outer shell 510. This configuration may reduce the risk of fluid leakage during connection or disconnection of the assembly 500 to or from a fluid line. Stated differently, the assembly 500 may be engaged before the assembly 500 is actuated, i.e., the fluid path is opened. In addition, the assembly 500 may provide a lock that substantially secures the assembly 500 in the actuated condition until the user affirmatively decides to deactuate the assembly 500.

Figure 30A:
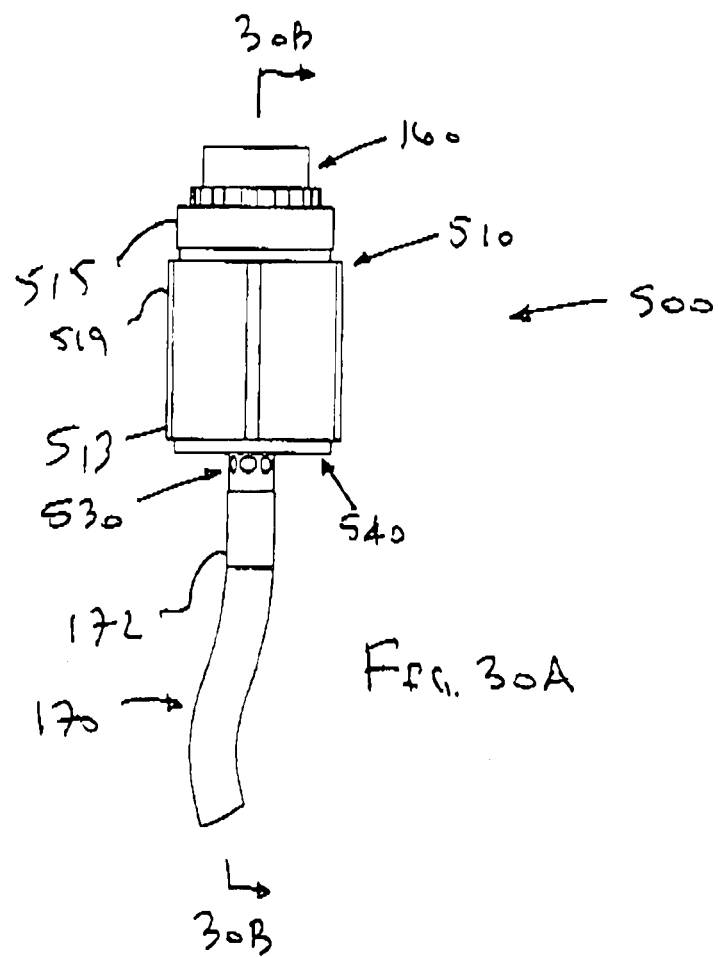
FIG. 30A is a side view of the assembly of FIGS. 24A-24C in an actuated condition after the Luer fitting has been connected to the assembly.
Figure 30C:
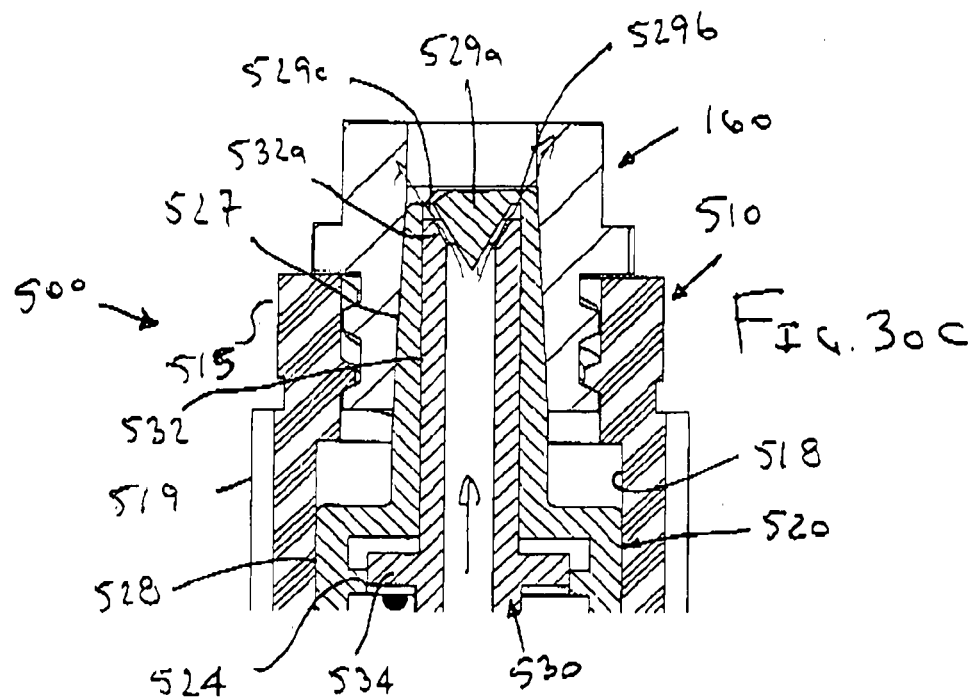

In addition, as best seen in FIG. 30A, when the female Luer connector 160 is tightened into the proximal end 515 of the outer shell 510, thereby causing the shaft 530 to be directed distally, one or more actuated status indicators 526 may become exposed below the backing member 540. The status indicator(s) 526 may include a color (such as green), one or more words, and the like, similar to other embodiments herein, which may provide the user visual confirmation that the assembly 500 has achieved the actuated position in which the flow path is open. In addition, the blunt ends 522b of the tabs 522 entering the pockets 535b of the cam features 535 may also provide a tactile indication to the user that the assembly 500 has been successfully actuated. In addition or alternatively, the tabs 522 may generate a "click" or other audible sound as they enter the pockets 535b, providing further confirmation to the user.

When it is desired to disconnect the assembly 500 and/or close the fluid path, the female Luer 160 may be unthreaded from the outer shell 510. This causes the inner housing 520 to rotate relative to the shaft 530, thereby removing the tabs 522 from the pockets 535b. As soon as the tabs 522 are disengaged from the pockets 535b, the spring 550 may bias the shaft 530 to move proximally, thereby causing the ramped surfaces 522a, 535a to again slide relative to one another and direct the mating member 534 back over the circumferential ledges 524. Thus, as the female Luer 160 begins to move proximally during unthreading, the shaft 530 may immediately move proximally relative to the inner housing 520, thereby reengaging the proximal end 532a of the shaft 530 with the sealing pin 529a on the inner housing 520. This action therefore closes the fluid path at the beginning of unthreading of the female Luer 160, thereby minimizing fluid leakage during disconnection. Thus, the assembly 500 may be deactuated immediately, while the assembly 500 is still engaged to the female Luer fitting 160. Thereafter, the female Luer fitting 160 may be unthreaded from the assembly 500 without substantial risk of fluid leakage.

Figure 45A:
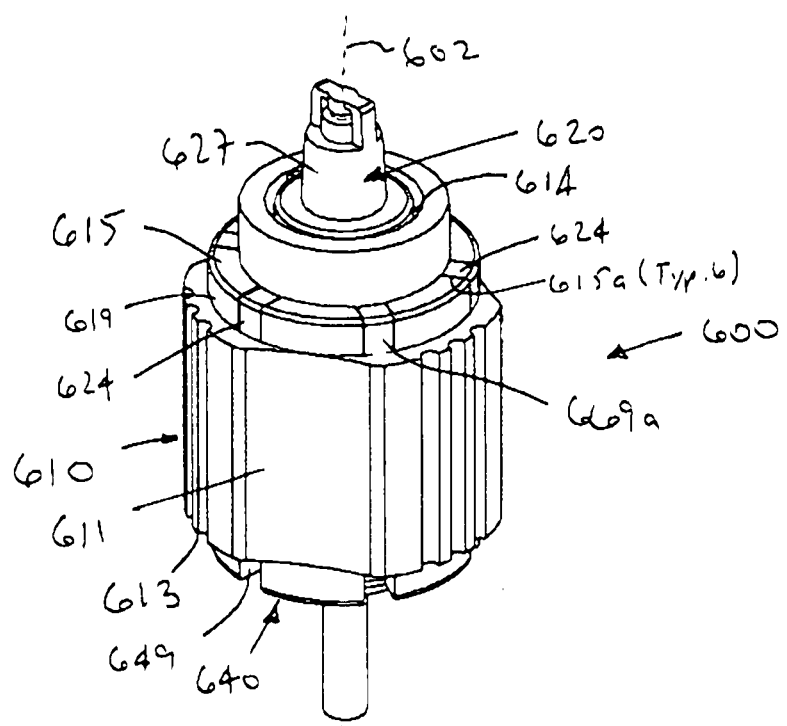
FIG. 45A is a perspective view of another embodiment of a connecting assembly including an outer shell with a male Luer thread connected to a distal end of a length of tubing.

Turning to FIGS. 45A-50B, yet another embodiment of a valve/connector assembly 600 is shown that includes similar general components as the previous assemblies. As shown in FIGS. 45A-45C, the assembly 600 includes an outer shell or bezel 610 with a male Luer thread 614, a covering body or inner housing 620, and a spring or other elastic member 650 disposed between a backing member 640 and a camming element 660. Unlike the previous embodiments, a length of tubing 630 is used instead of a separate shaft within the assembly 600, although alternatively, the camming element 660 may be incorporated into a shaft (not shown), similar to the previous embodiments. The components of the assembly 600 are aligned generally along a central axis 602, e.g., such that one or more of the components may move axially and/or rotationally relative to the axis 602, as described further below.

Similar to the previous embodiments, the outer shell 610 includes proximal and distal ends 615, 613, and a distal throughbore 618 and a proximal throughbore 616 communicating with one another. Similar to the previous embodiments, the proximal throughbore 616 includes the male Luer thread 614 therein adjacent the proximal end 615, although alternatively, a female Luer connector or other connector (not shown) may be provided on the proximal end 615 instead, if desired. As shown, the outer shell 610 has a hexagonal shaped outer surface 611 including vertical grooves to facilitate manipulating the assembly 600, although, alternatively, the outer surface may have other shapes, similar to the previous embodiments.

The distal throughbore 618 extends axially from the distal end 613 of the outer shell 610 to intermediate location 619. The length, size, and/or shape of the distal throughbore 618 is sufficient to accommodate at least a portion of the inner housing 620, camming member 660, tubing 630, and backing member 640 therein. The diameter or other cross-section of the distal throughbore 618 may be larger than the proximal throughbore 616, e.g., to provide an abutment surface at the intermediate location 619 for limiting proximal movement of the inner housing 620 into the distal throughbore 618, as explained further below.

A circumferential ridge 617 or one or more other connectors (not shown) may be provided on or adjacent the distal end 613, e.g., within the distal throughbore 618. The ridge 617 may extend at least partially around the distal end 613 of the outer shell 610, e.g., within the distal throughbore 618. As shown, the ridge 617 may include separate ridge portions that each extends only partially around the distal end 613, along an extended portion of the outer shell 610 that are spaced apart by shortened portions of the outer shell 610. Alternatively, the ridge 617 may extend entirely around the distal end 617 (not shown). The ridge 617 may have a slightly smaller diameter than the rest of the distal throughbore 618 to engage or otherwise capture a portion of the backing member 560, e.g., to provide a "snap" connection that couples the outer shell 610 to the backing member 640. For example, the ridge 617 may include a ramped distal edge and a blunt proximal edge to allow the backing member 640 to be inserted into the distal end 613 while preventing subsequent removal. As described further below, once attached, the outer housing 610 may be substantially fixed relative to the backing member 640, i.e., preventing both relative axial and rotational movement of the outer housing 610 and the backing member 640, as described further below.

The dimensions of the proximal throughbore 616 and male Luer thread 614 may be provided according to ISO standards for Luer connectors. Alternatively, other connectors (not shown) may be provided on the proximal end 615, if desired, similar to the previous embodiments.

Figure 46A:
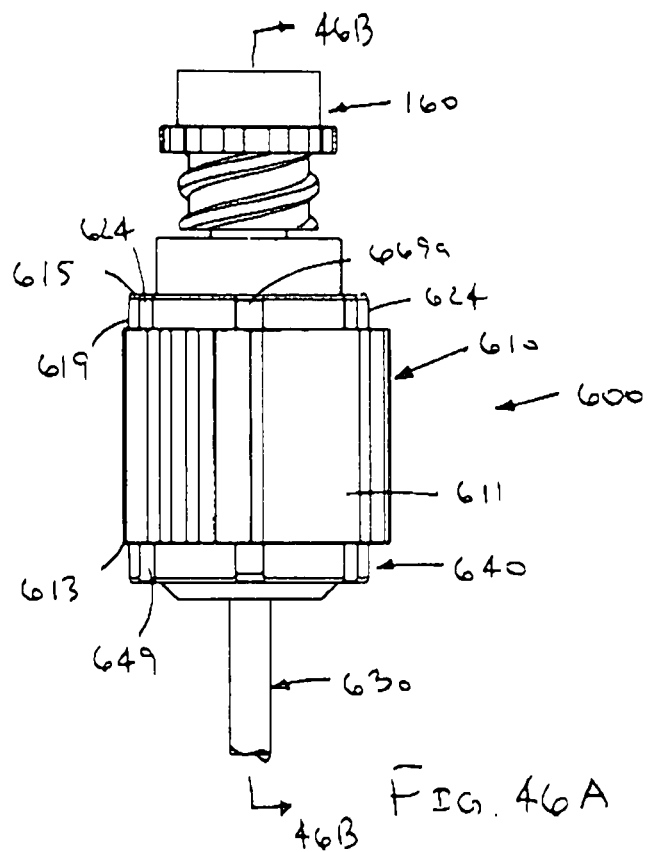
FIG. 46A is a side view of the assembly of FIGS. 45A-45C in a deactuated condition before a Luer fitting has been connected to the assembly.
Figure 46B:
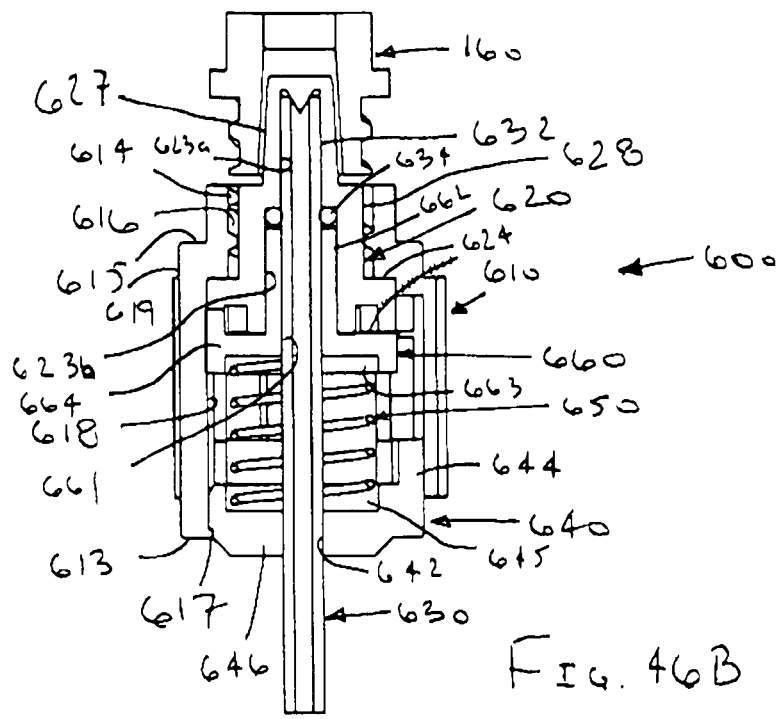
FIG. 46B is a cross-sectional view of the assembly of FIG. 46A, taken along lines 46B-46B.
Figure 47B:
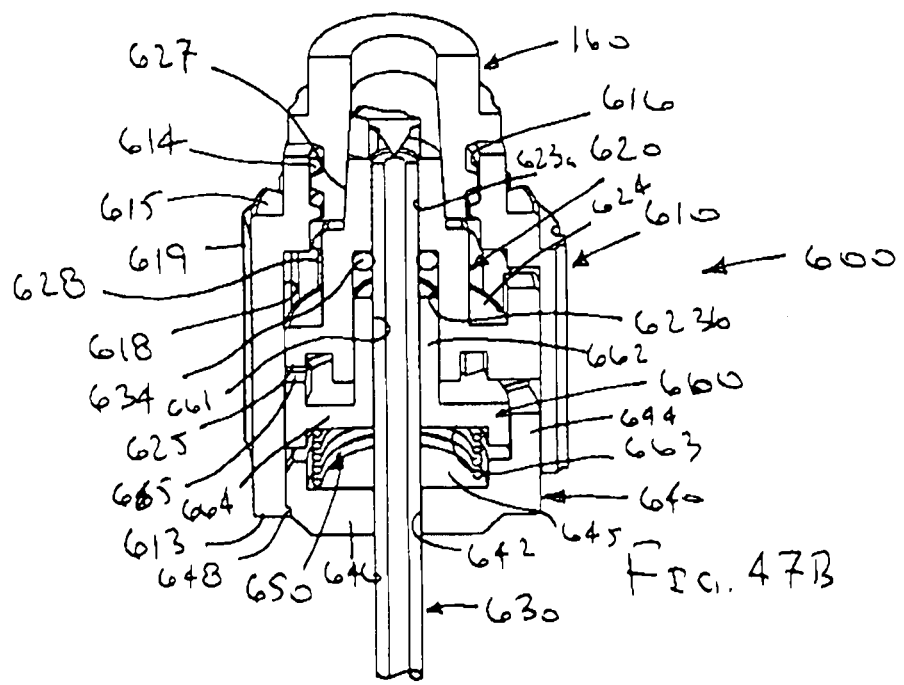
FIG. 47B is a cross-sectional view of the assembly of FIG. 47A, taken along lines 47B-47B.
Figure 46C:
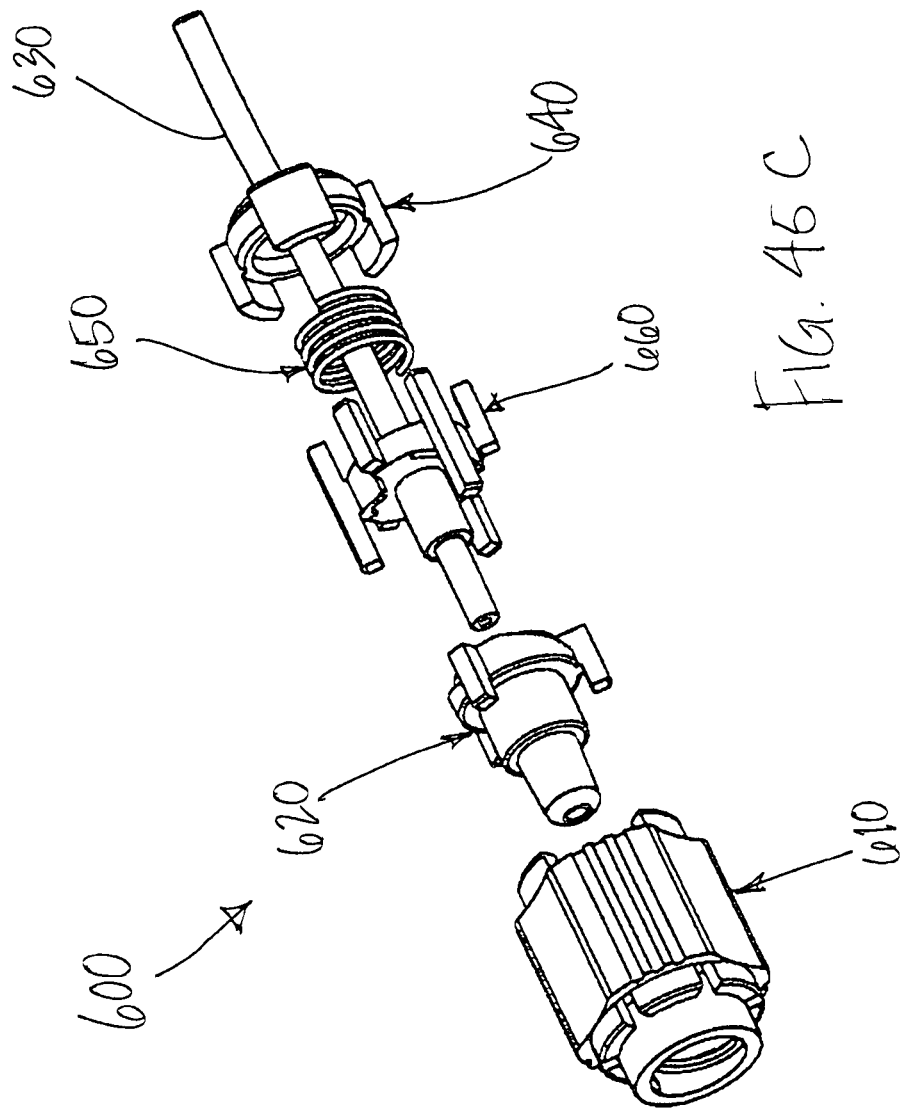
FIG. 46C is a perspective view of the assembly of FIG. 46A before the Luer fitting has been connected to the assembly.
Figure 47C:
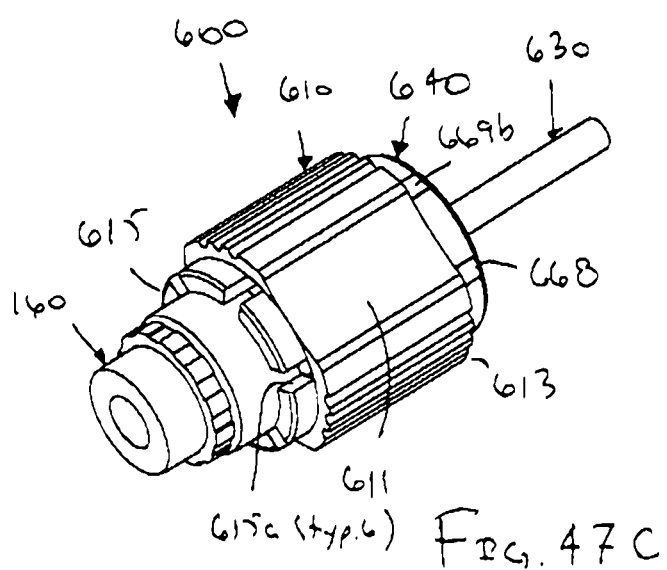
FIG. 47C is a perspective view of the assembly of FIG. 47A after the Luer fitting has been connected to the assembly.

As best seen in FIGS. 46B, 47B, and 49A-49D, the inner housing 620 generally includes an elongated male boss 627, an enlarged mating portion 628, and a throughbore 623 extending axially therethrough. The male boss 627 may be dimensioned per ISO industry standards, e.g., having a cylindrical shape with a tapered proximal end. The male boss 627 and mating portion 628 of the inner housing 620 may be integrally molded or otherwise formed from a single piece or may be separate pieces substantially permanently attached to one another. The throughbore 623 runs the entire length of inner housing 620, e.g., through the mating portion 628 and the male boss 627, e.g., similar to the previous embodiments. As best seen in FIGS. 46B and 47B, the throughbore 623 includes a relatively narrow portion 623*a* that extends through the male boss 627 and a relatively wider portion 623*b* that extends through the mating portion 628.

As described further below, the narrow portion 623*a* may accommodate receiving an end 632 of the tubing 630 therethrough, while the wider portion 623*b* may accommodate slidably receiving a guide portion 662 of the camming element 660 therein. An o-ring 634 or other seal may be provided within the throughbore 623, e.g., within the wider portion 623*b* immediately adjacent the male boss 627, to provide a fluid-tight seal between the tubing 630 and the inner housing 620, also as described further below.

Similar to the previous embodiments, the inner housing 620 may be received within the outer shell 610, e.g., by inserting the male boss 627 through the distal throughbore 618 into the proximal throughbore 616, as shown in FIGS. 46B and 47B. When the male boss 627 is received in the proximal throughbore 616, the mating portion 628 may be received in the distal throughbore 618, e.g., contacting the abutment surface at the intermediate location 619 when advanced fully into the outer shell 610, and the male boss 627 may extend concentrically within and through the male Luer thread 614.

The mating portion 628 may have a diameter similar to the distal throughbore 618, e.g., such that the mating portion 628 may slide axially and rotate freely within the distal throughbore 618 without substantial lateral movement. In addition, one or more camming surfaces 625 may be molded, machined, or otherwise provided along the mating portion 628. For example, the mating portion 628 may include one or more camming surfaces 625 (three shown) spaced apart from one another about the circumference of the mating portion 628 that extend helically partially around the mating portion 628, thereby defining a lower surface of the inner housing 620. The camming surfaces 625 may correspond to similar camming surfaces 665 on the camming element 660, as described further below. Alternatively, other cooperating surfaces, ridges, grooves, and/or other features (not shown) may be provided on the mating portion 628 and the camming element 660, i.e., to provide guiding features between the mating portion 628 and the camming element 660. In addition or alternatively, any number of cooperating surfaces or other features, e.g., one or more, may be provided on the mating portion 628 and camming element 660 to allow the mating portion 628 to move axially and/or helically relative to the camming element 660 during actuation of the assembly 600, as described further below.

In addition, as best seen in FIGS. 45B and 49A-49D, the inner housing 620 may include one or more indicator posts 624 spaced apart from one another about a circumference of the inner housing 620. For example, as shown, three posts 624 are provided on the mating portion 628 that extend generally axially towards the proximal end 615 of the outer shell 610 and the outer shell 610 may include corresponding openings 615*a* in the proximal end 615 aligned with the posts 624. For example, the posts 624 may extend at least partially into or through the openings 615*a* when the assembly 600 is deactuated, i.e., when the assembly 600 is closed to prevent fluid flow therethrough, as described further below. Optionally, the outer shell 610 may include one or more tracks on its inner surface (not shown), if desired, for slidably receiving the posts 624, e.g., to facilitate or limit movement of the inner housing 620 relative to the outer shell 610.

Figure 50B:
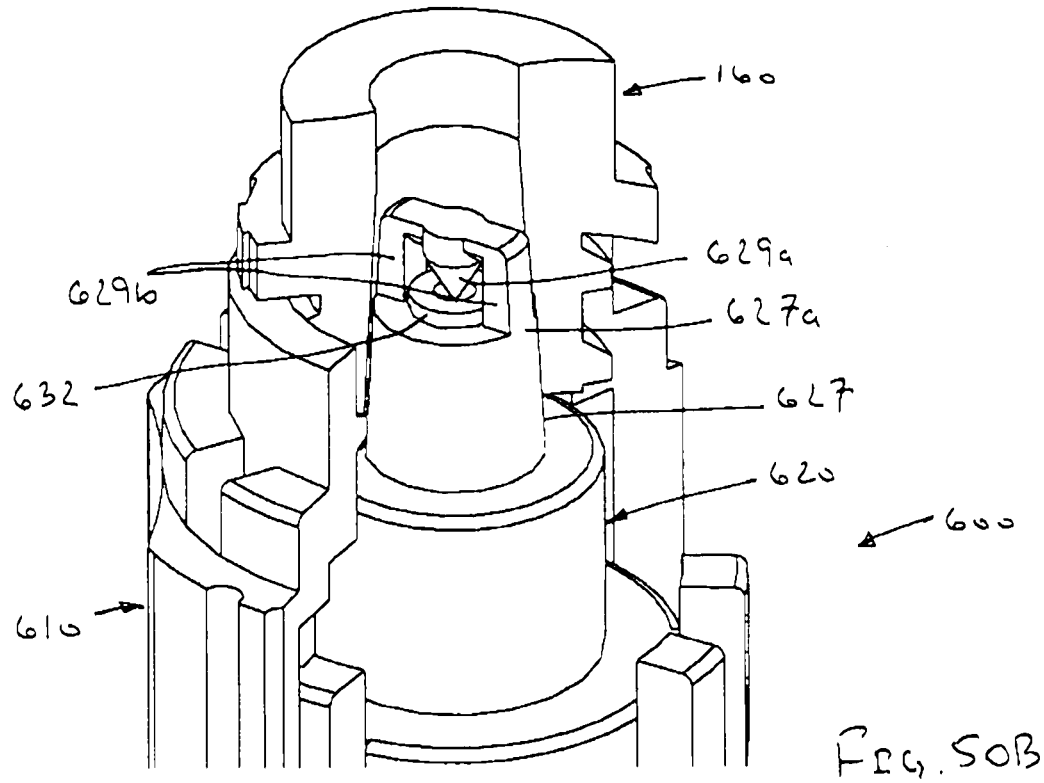
FIGS. 50A and 50B are perspective details of the assembly of FIGS. 45A-49D, showing an outlet port of the assembly closed and open, respectively.
Figure 50A:
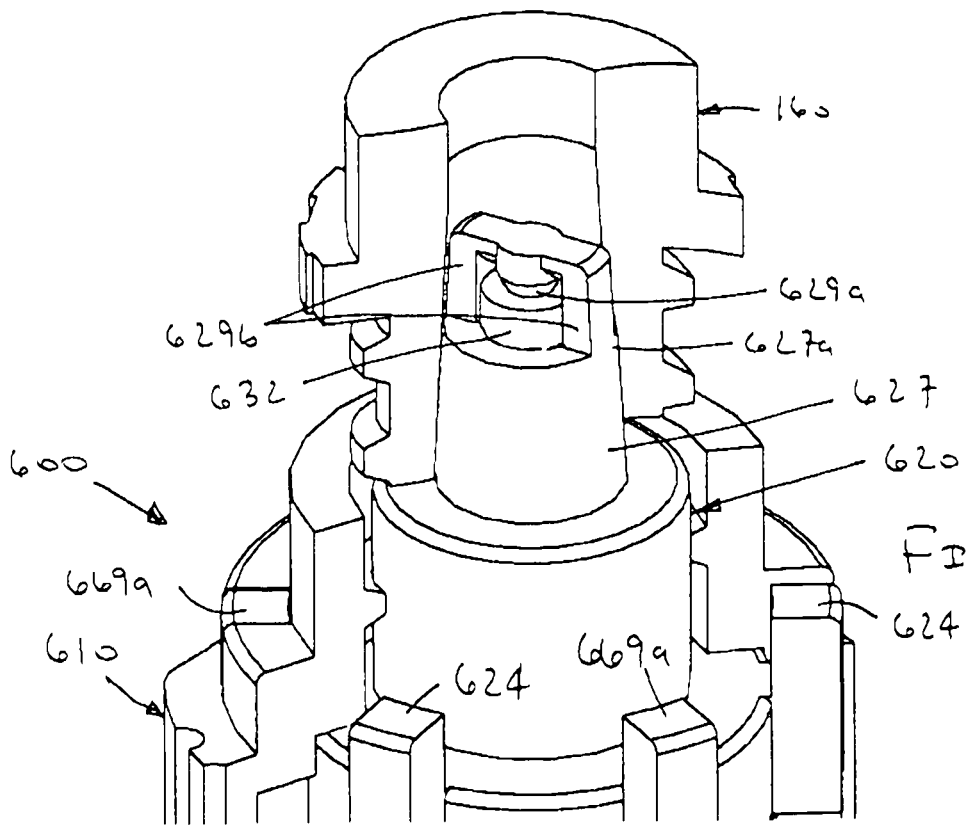

The male boss 627 may include a seal 629 aligned with the throughbore 623, e.g., at the proximal end 627*a* of the male boss 627 for selectively sealing the assembly 600, as described further below. For example, as best seen in FIGS. 50A and 50B, the seal 629 may include a central sealing pin 629*a* supported by one or more supports 629*b* extending radially inwardly from the proximal end 627*a* of the male boss 627. As shown, two supports 629*b* may be disposed radially around the sealing pin 629*a*, thereby defining a pair of openings through which fluid may flow, although alternatively only one or three or more supports (not shown) may be provided. The sealing pin 629*a* may have a conical shape, as shown, or, alternatively, a frusto-conical or other shape (not shown) for sealing the end 632 of the tubing 630 secured in the assembly 600.

Figure 45B:
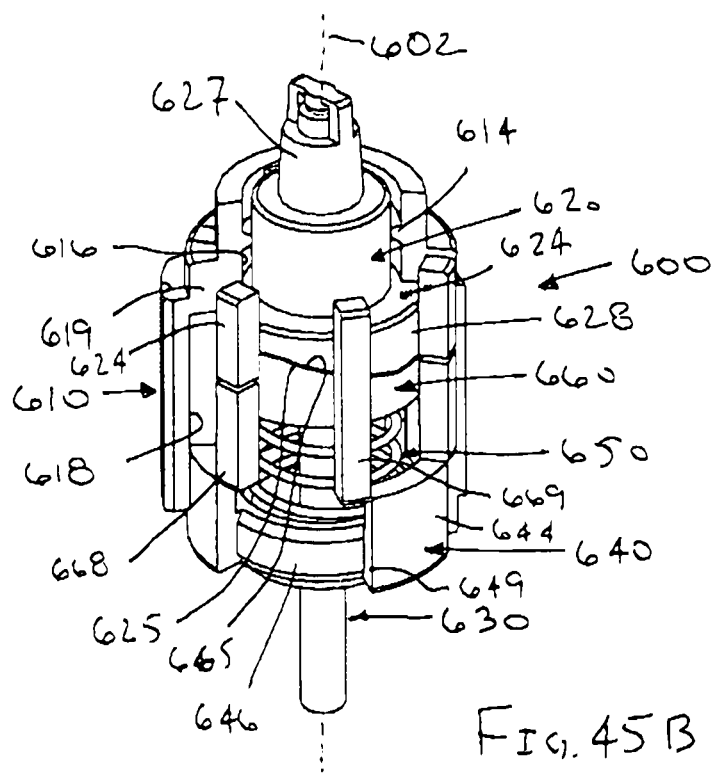
FIG. 45B is a perspective view of the assembly of FIG. 45A with portions of the outer shell and backing member removed to show internal components of the assembly.
Figure 47A:
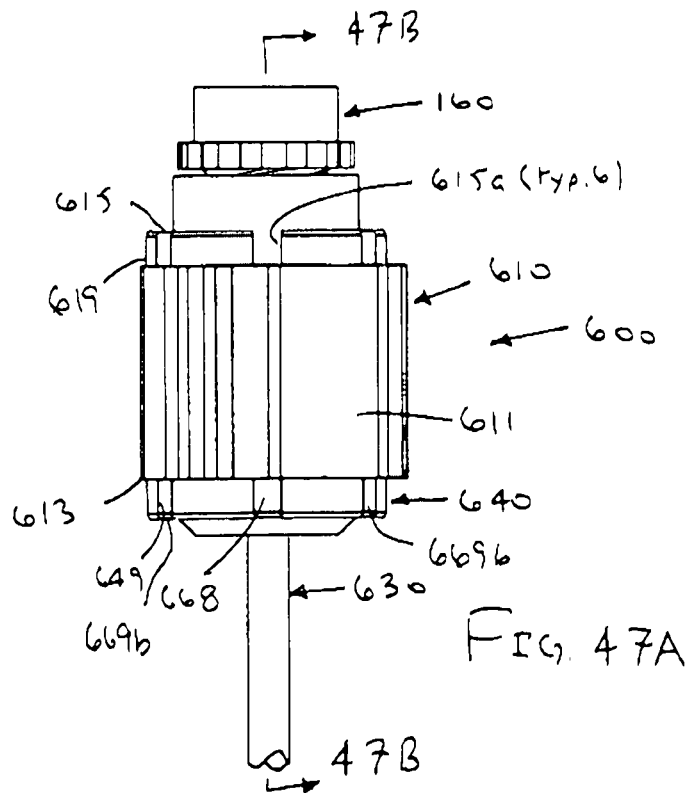
FIG. 47A is a side view of the assembly of FIGS. 45A-45C in an actuated condition after the Luer fitting has been connected to the assembly.

With particular reference to FIGS. 45B, 46B, and 47B, the camming element 660 may be slidably disposed within the outer shell 610 between the inner housing 620 and the backing member 640. The camming element 660 may include a narrow guide portion 662 that is slidably received within the inner housing 620, e.g., within wider portion 623*b* of the throughbore 623, and a wider camming portion 664 that includes the camming surfaces 665. The guide portion 662 includes an axial passage 661 therethrough, e.g., having sufficient size to receive the tubing 630 therethrough. For example, the passage 661 may be slightly larger than the tubing 630 such that the tubing 630 may be pushed through the passage 661, yet provide a sufficient interference fit such that subsequent movement of the tubing 630 relative to the inner housing 620 is coupled to the camming element 660, as described further below. Alternatively, the camming element 660 may include a seal or other feature (not shown) within the passage 661 to allow the tubing 630 to be inserted through the passage 661 but provide increased friction or other interference fit to couple movement of the tubing 630 and camming element 660. Optionally, the camming element 660 may include a recess 663 to accommodate receiving one end of the spring member 650, as described further below.

The camming surfaces 665 may be spaced apart from one another around the circumference of the camming element 660, e.g., extending helically partially around an outer edge of the camming portion 664. The camming surfaces 665 may be configured to slidably contact and/or otherwise interact with the camming surfaces 625 on the inner housing 520, e.g., to effect actuation and/or deactuation of the assembly 600, as described elsewhere herein. Similar to the previous embodiments, the angle of the camming surfaces 625, 665 may be changed, e.g., to correspond to the selected configuration, e.g., number and/or orientation of the camming surfaces 625, 665, for example, to maximize fluid flow upon actuation.

In addition, the camming element 660 includes a plurality of indicator posts 668, 669 spaced apart about a circumference of the camming element 660, e.g., extending from the outer surface of the camming portion 664. For example, as shown, the camming element 660 includes three relatively short posts 668 and three relatively long posts 669 alternately spaced apart about the camming portion 664. The indicator posts 668 may extend axially from the camming portion 624, e.g., towards the backing member 640 to provide indicators when the assembly 600 has been actuated, i.e., open to allow fluid flow therethrough, as described further below. The indicator posts 669 also extend axially but have sufficient length such that first ends 669a of the posts 669 extend through corresponding openings 615a in the outer shell 610 when the assembly 600 is deactuated and second ends 669b of the posts 669 extend through corresponding openings 649 in the backing member 640 when the assembly 600 is actuated. The posts 668, 669 may also prevent rotation of the camming element 660 relative to the outer shell 610 and/or backing member 640, also as described further below. For example, the outer shell 610 and/or backing member 640 may include one or more tracks or other recesses for slidably receiving one or more of the indicator posts 668, 669, e.g., to allow the camming element 660 to slide axially without rotating within the outer shell 610. In addition or alternatively, the camming member 660 and the outer shell 610 or backing member 640 may include one or more features, e.g., tracks, tabs or other guide elements, and the like (not shown) to allow the camming member 660 to move axially without substantial rotational movement relative to the outer shell 610, e.g., similar to the previous embodiments.

As best seen in FIGS. 45A-47C, the backing member 640 includes a base portion 646 including a passage 642 therethrough, and an annular portion 644 extending proximally from the base portion 646. The passage 642 may have sufficient size to accommodate receiving the tubing 630 therethrough, optionally including a tapered or otherwise shaped lower surface to facilitate inserting the end 632 of the tubing 630 into the passage 642 during assembly, as described further below. The annular portion 644 may define a recess 645 for receiving one end of the elastic member 650 (or other elastic member) therein, e.g., such that opposite ends of the elastic member 650 may be received in the recesses 645, 663, thereby capturing the elastic member 650 between the backing member 640 and the camming element 660. As best seen in FIG. 45C, the annular portion 644 may be divided into separate curved portions, e.g., to accommodate receiving respective ridges 617 therebetween, e.g., to connect the backing member 640 to the outer housing 610.

The backing member 640 may include one or more openings 649, e.g., extending axially along the annular portion 644 for slidably receiving corresponding posts 668, 669 on the camming member 660, e.g., when the assembly 600 is actuated to the open condition. Optionally, the openings 649 may extend proximally a sufficient distance to provide guide tracks for the posts 668, 669, e.g., to allow axial movement of the camming element 660 without substantial rotation.

The backing member 640 may also include one or more connectors for attaching the backing member 640 to the outer shell 610. For example, grooves 648 may be provided around the base portion 646 between the curved portions of the annular portion 644 for receiving respective ridges 617 on the outer shell 610. Alternatively, the backing member 640 may include one or more other connectors (not shown) that may cooperate with corresponding connectors (also not shown) on the outer shell 610, e.g., for coupling the backing member 540 to the outer shell 510.

The elastic member 650 may be a compression spring having a diameter smaller than the recesses 645, 663. For example, the inner diameter of the spring 650 may be sized to be received around the tubing 630, e.g., such that the elastic member 650 does not interference with insertion of the end 632 of the tubing 630 into the backing member 640, camming element 660, and into the inner housing 620. Opposite ends of the elastic member 650 may press against the backing member 640 and camming element 660 such that the elastic member 650 may bias the camming element 660 and inner housing 620 away from the backing member 640 and/or towards the proximal end 615 of the outer shell 610, as described further below.

During manufacturing, the components of the assembly 600 may be formed and assembled together. Although exemplary methods are described herein, it will be appreciated that the order of the various stages or steps and/or the particular steps used may be changed, as desired, e.g., based upon manufacturing convenience and/or other factors. For example, each of the outer shell 610, inner housing 620, backing member 650, and camming element 660 may be integrally molded, machined, or otherwise formed separately from one another, e.g., from plastic, metal, or composite material, similar to the previous embodiments.

The inner housing 620 may be inserted into the distal end 613 of the outer shell 610, as described above, and the camming element 660 may be inserted into the distal end 613 of the outer shell 610, e.g., after or simultaneously with the inner housing 620. During insertion, the guide portion 662 of the camming element 660 may be inserted into the wider portion 623b of throughbore 623 of the inner housing 620, e.g., until the camming surfaces 665 contact camming surfaces 625 on the inner housing 620. The elastic member 650 may be inserted into the distal end 613 of the outer shell 610, e.g., until one end is received within the recess 663 of the camming element 660.

The backing member 640 may then be inserted into the distal end 613 of the outer shell 610, for example, by aligning the ridge portions 617 of the outer shell 610 between the curved portions of the annular portion 644, e.g., such that the ridge portions 617 engage respective grooves 648 between the curved portions 644 in the backing member 640. As the backing member 640 is secured within the outer shell 610, the opposite end of the elastic member 650 may be received within the recess 645 within the backing member 640, e.g., slightly compressing the elastic member 650 between the camming element 660 and the backing member 640.

The distal end 632 of a length of tubing or other conduit 630 may be inserted into the backing member 640 through the passage 642, through the passage 661 in the camming element 660, and through the narrow portion 623a of the throughbore 623 of the inner housing 620. The backing member 640 may include a tapered surface or other features (not shown) communicating with the passage 642, e.g., to facilitate initially inserting the tubing 630 into the passage 642. The tubing 630 may pass freely through the interior of the elastic member 650 and then through the passage 661 in the camming element 660 with sufficient force to overcome friction between the tubing 630 and the wall of the passage 661, e.g., until the tubing 630 contacts the o-ring 634. The tubing 630 may then be directed through the o-ring 634 and into the narrow portion 623a of the throughbore 623 until the distal end 632 of the tubing 630 abuts the sealing pin 629a.

The distal end 632 of the tubing 630 may substantially engage the sealing pin 629a, thereby providing a fluid-tight seal that prevents substantial fluid flow through the distal end 632 of the tubing 630. Thus, the tubing 630 may be secured axially relative to the camming element 660, e.g., such that friction provides an interference fit between the tubing 630 and the wall of the passage 661 in the camming element 660, while the tubing 630 may be free to move axially relative to the inner housing 620, outer shell 610, and/or backing member 640. In addition or alternatively, an adhesive or other fastening method may be used to fix the tubing 630 relative to the camming element 660, if desired.

The tubing 630 may be formed from flexible material, e.g., silicone and the like, which may facilitate sealing between the distal end 632 and the sealing pin 629a. In addition or alternatively, the tubing 630 may be formed from material that accommodates receiving particular therapeutic and/or diagnostic compounds or other fluids therethrough, e.g., that may be inert to corrosive or other compounds to be delivered through the assembly 600. The tubing 630 may have sufficient length such that a free end (not shown) of the tubing 630 may be connected to a fluid line, e.g., for an IV or other device (not shown). The free end of the tubing 630 may include a connector (not shown), such as a male or female Luer fitting, and the like, to facilitate connection to a fluid line. Alternatively, the tubing 630 may communicate with another device, such as those described elsewhere herein.

It will be appreciated that the tubing 630 may be inserted into the other components of the assembly 600 immediately before use, or during initial manufacturing, as desired. Alternatively, the tubing 630 may be received within the passage 661 and attached to the camming element 660 before inserting the camming element 660 into the outer shell 610 and inner housing 620, if desired. Optionally, as shown in FIG. 51, the backing member 640' may include a cavity or passage 645' for receiving excess length of the tubing 630 inserted through the backing member 640. Such a configuration may facilitate movement of the tubing 630 axially within the outer shell 610 without the tubing 630 moving into or out of the backing member 640.

During use, the assembly 600 may be initially provided as shown in FIGS. 45A, 45B, 48A, and 50A. In this condition, the assembly 600 may be in a closed position, e.g., with the end 632 of the tubing 630 substantially sealed by the seal 629 on the inner housing 620, e.g., as best seen in FIG. 50A. In the closed position, the elastic member 650 may press the camming element towards the proximal end 615 of the outer shell 610, thereby pushing the inner housing 620 proximally, e.g., until the male boss 627 is received within the male Luer thread 614 and the mating portion 628 abuts the abutment surface at the intermediate location 619 in the outer shell 610, e.g., as best seen in FIG. 45B. One advantage of this configuration is that the end 632 of the tubing 630 and the seal 629 are exposed, which may facilitate cleaning the end 632 and seal 629 during use.

Figure 48A:
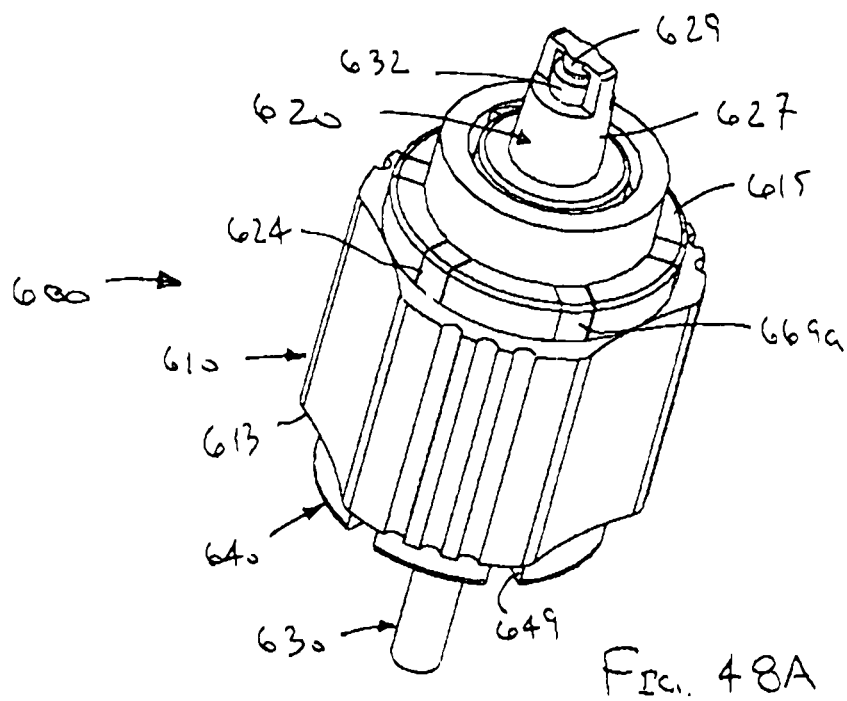
FIGS. 48A-48D are perspective views of the assembly of FIGS. 45A-47C, showing a sequence of actuation while a Luer fitting is being connected to the assembly.

As shown in FIGS. 45A and 48A, in the closed position the posts 624 and ends 669a of posts 669 may be received in the openings 615a in the outer shell 610, e.g., providing a visual confirmation that the assembly 600 is in the closed position. Optionally, the posts 624 and ends 669a may include one or more visual markers, e.g., a color, such as red, text, and the like (not shown), which may enhance identification of the status of the assembly 600, similar to the previous embodiments.

Turning to FIGS. 48B-48D and 49A-49D, a female Luer fitting 160 may be threaded into the outer shell 610, e.g., by threading the fitting 160 into the male Luer thread 614, similar to the previous embodiments, which may secure the female Luer fitting 160 to the assembly 600 and actuate the assembly 600. Alternatively, the assembly 600 may be configured to include a female Luer fitting (not shown), similar to other embodiments described herein, and a male Luer fitting (also not shown) may be coupled to the assembly 600 during use.

Figure 48B:
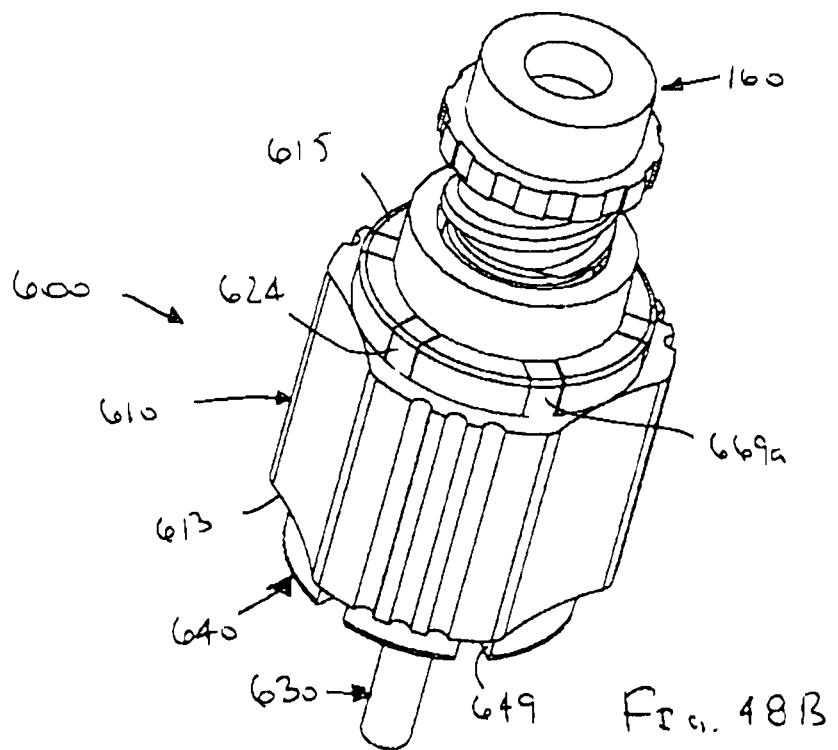
Figure 49A:
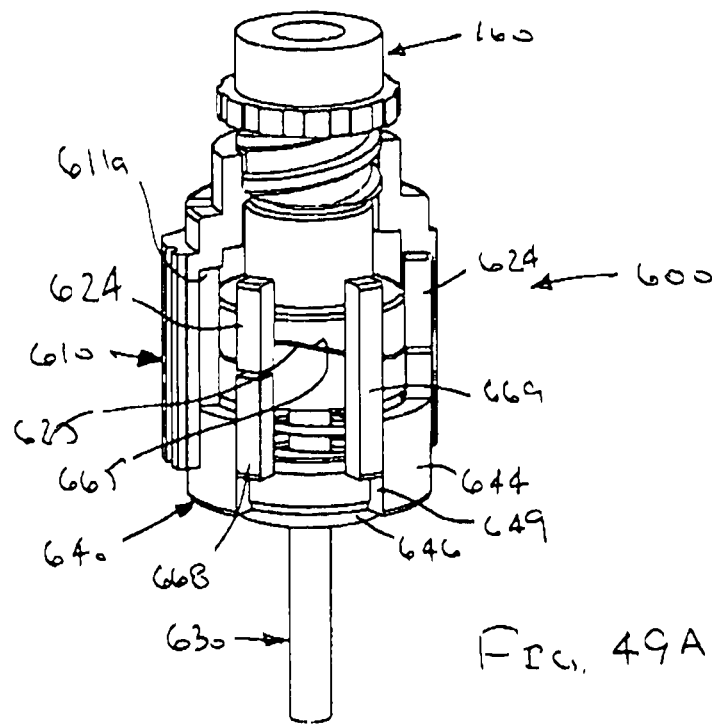
FIGS. 49A-49D are perspective views of the assembly of FIGS. 48A-48D, respectively, with portion of the outer shell and backing member removed to show movement of the internal components of the assembly during actuation.

When the fitting 160 is initially threaded into the outer shell 610, the fitting 160 may contact the male boss 627 on the inner housing 620. Once the fitting 160 is fully engaged with the male boss 627, further threading of the fitting 160 causes the inner housing 620 and camming element 660 to move distally relative to the outer shell 610 and the backing member 640, as shown in FIGS. 48B and 49A. Because the posts 624 of the inner housing 620 are received in openings 615a, the inner housing 620 initially is limited to axial distal movement without substantial rotation relative to the outer shell 610. Optionally, the openings 615a in the outer shell 610 may communicate with slots or other tracks extending along the inner surface of the outer shell 610 to slidably receive the posts 624 and prevent rotation of the inner housing 620 while the posts 624 are within the slots.

Similarly, because the posts 668, 669 on the camming element 660 are received in slots communicating with the openings 649 in the backing member 640 (and/or with slots or other tracks extending along the inner surface of the outer shell 610), the camming element 660 is limited to axial movement and limited from rotating substantially relative to the outer shell 610. As the fitting 160 is inserted, pushing the inner housing 620 and camming element 660 distally, the elastic member 650 may be compressed between the camming element 660 and backing member, thereby storing potential energy in the elastic member 650. As the inner housing 620 and camming element 660 move distally, the end 632 of the tubing 630 may remain substantially engaged with the seal 629, thus maintaining the assembly 600 in the closed position and preventing fluid from leaking from the end 632 of the tubing 630.

Figure 48D:
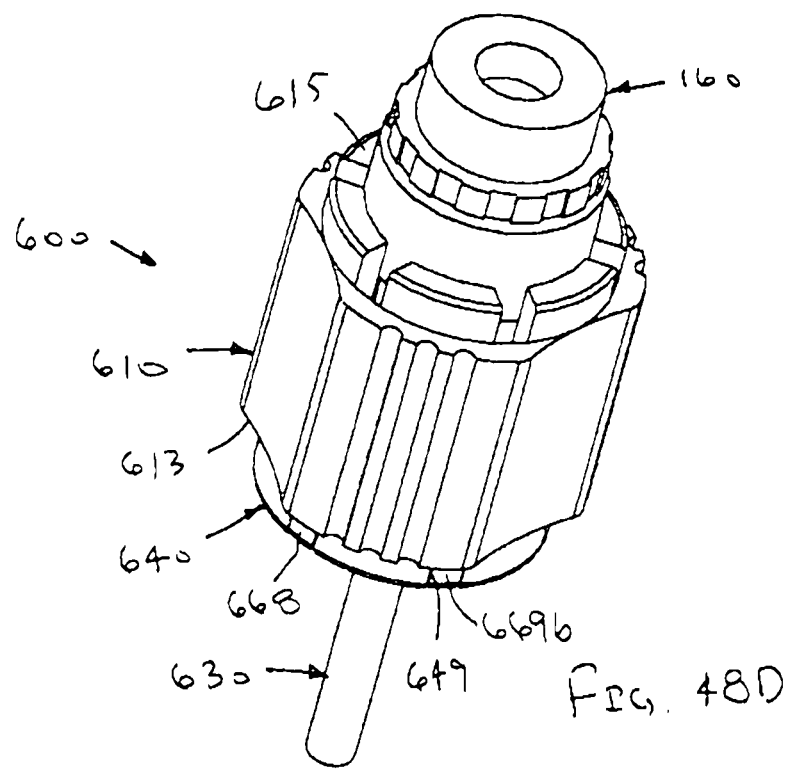
Figure 48C:
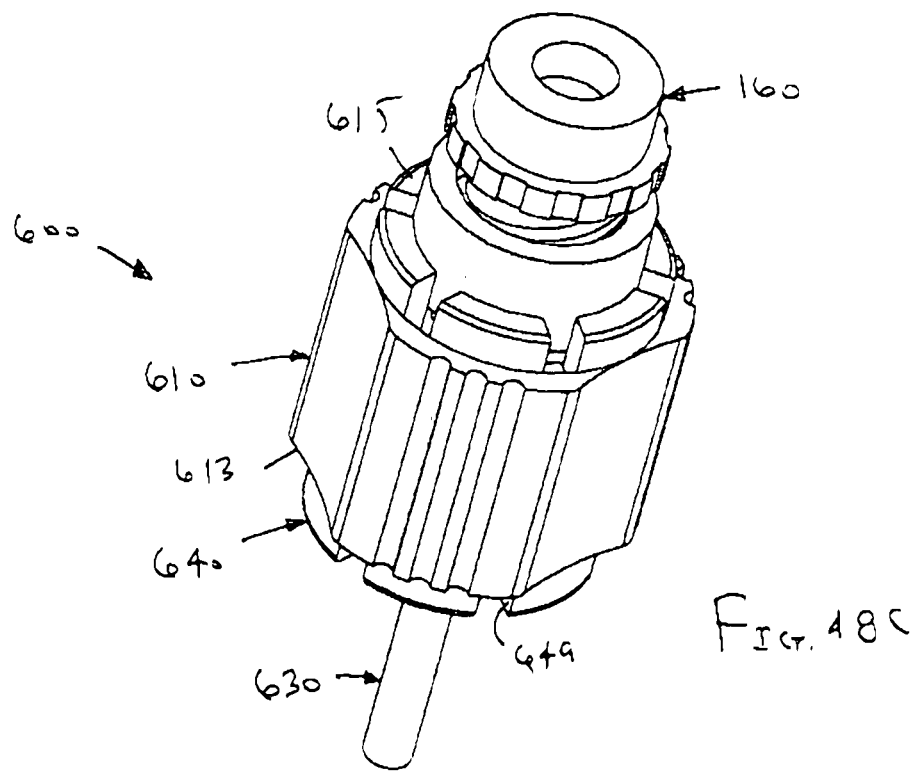
Figure 49C:
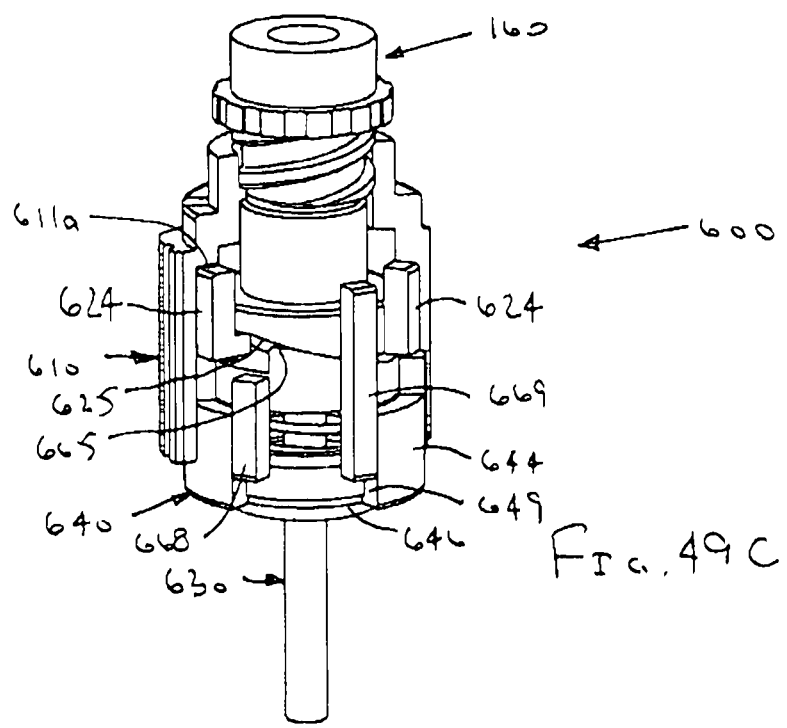
Figure 49D:
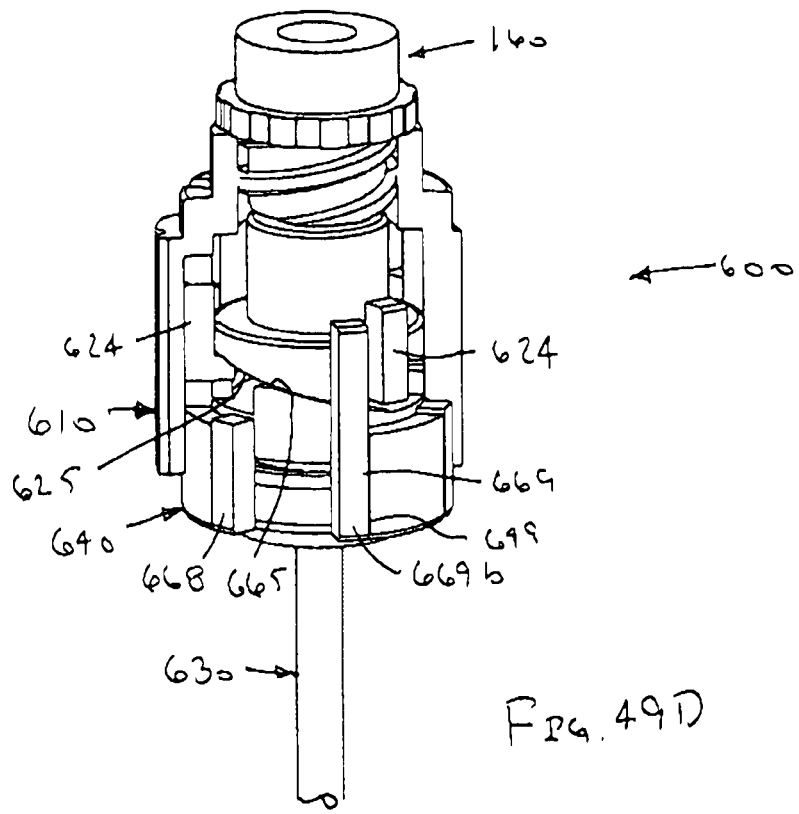
Figure 49B:
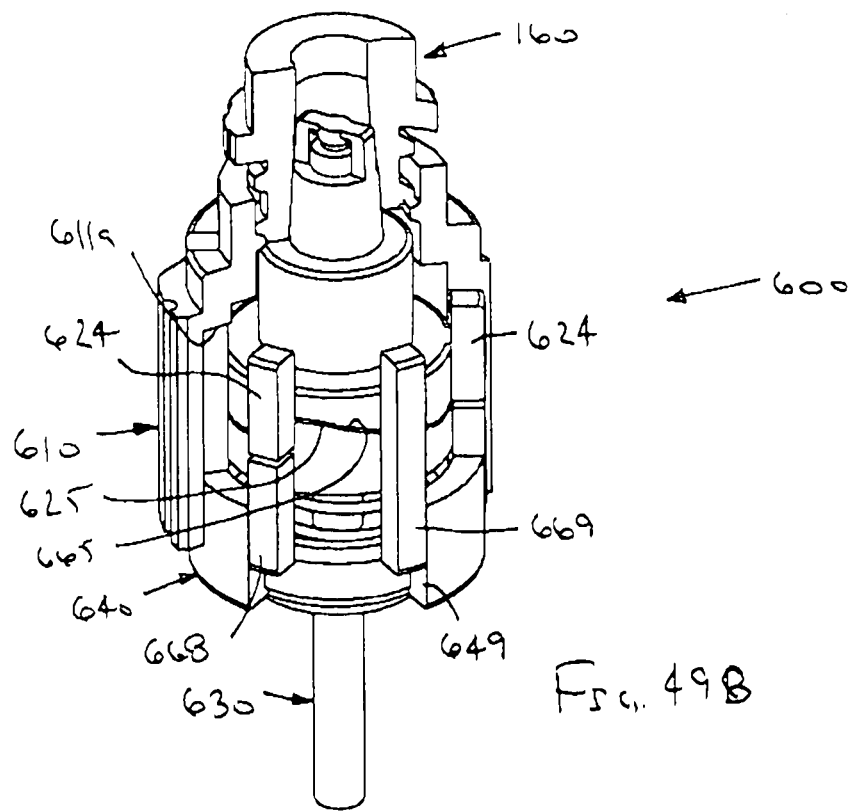

Turning to FIGS. 48C and 49C, once the posts 624 pass below the openings 615a and any slots or tracks within the outer shell 610, further threading of the fitting 160 continues to cause distal movement of the inner housing 620 but also causes the inner housing 620 to rotate, i.e., move helically distally relative to the backing member 540. Because of the cooperating camming surfaces 625, 665 on the inner housing 620 and camming element 660, the camming element 660 remains in its proximal position (shown in FIGS. 49B and 49C) until the inner housing 620 rotates completely, whereupon the camming surface 625, 665 push the camming element 660 distally relative to the inner housing 620, outer shell 610, and backing member 640, as shown in FIGS. 48D and 49D.

As the camming element 660 moves distally, the posts 668, 669 are also directed distally until the posts 668 and ends 669b of posts 669 are received in the openings 649 in the backing member 640. Because the tubing 630 is coupled to the camming element 660, as the camming element 660 moves distally relative to inner housing 620, the end 632 of the tubing 630 moves distally relative to seal 629, thereby opening the distal end 632 and allowing fluid flow through the tubing 630 and into the fitting 160, similar to the previous embodiments. Because of the cooperation of the camming surfaces 625, 655, and the movement of the posts 624, 668, 669 relative to the outer shell 610, this actuation of the assembly 600 does not occur until the fitting 160 is substantially fully threaded into the male Luer thread 614. Thus, the end 632 of the tubing 630 is not opened until the fitting 160 is substantially fully threaded into the male Luer 614 of the outer shell 610, thereby substantially reducing the risk of fluid leaking from the tubing 630 prematurely. This may be particularly important for certain corrosive, toxic, or other compounds are being delivered through the assembly 600. When the posts 668, 669b appear in the openings 649, they provide a visual indication that the assembly 600 has been opened and that fluid may then flow through the assembly 600, as shown in FIGS. 48D and 49D. Optionally, the posts 668, 669b may include markers, similar to those described above, for facilitate visually identifying that the assembly 600 is in its open condition.

Optionally, the assembly 600 may include one or more features for releasably locking the assembly 600 in the open condition. For example, as best seen in FIGS. 49A-49D, the inner surface of the outer shell 600 may include one or more pockets 611a that may receive respective posts 624 on the inner housing 620. As the inner housing 620 is displaced axially and then rotationally within the outer shell 610 during actuation, the posts 624 may enter the pockets 611a such that the posts 624, and consequently, the inner housing 620 cannot move proximally and/or rotate. Thus, if the fitting 160 is fully threaded and released, the inner housing 620 may be prevented from moving axially, which may otherwise cause the fitting 160 to unthread from the assembly 600. Alternatively, other features (not shown) may be provided, e.g., on the inner housing 620 and/or outer shell 610 to lock the assembly 600 in the open condition.

When it is desired to discontinue flow through the assembly 600, the fitting 160 may simply be unthreaded from the male Luer thread 614. As soon as the posts 624 of the inner housing 620 are withdrawn from the pockets 611a, the bias of the elastic member 650 may push the camming element 660 proximally as the fitting 160 is unthreaded. The camming surfaces 625, 665 may then cooperate to immediately direct the camming element 660 proximally relative to the inner housing 620, thereby reengaging the end 632 of the tubing 630 with the seal 629. Thus, as soon as a user begins to unthread the fitting 160, the end 632 of the tubing 630 may be immediately sealed, thereby closing the assembly 600 from further fluid flow. As the fitting 150 is unthreaded, the inner housing 620 may return to its initial rotational orientation and then move proximally along with the camming element 660 until the posts 624, 669a reappear in the openings 615a in the outer shell 610. Thus, the user knows that fluid flow has discontinued and the assembly 600 has been returned to the closed position. If desired, the assembly 600 may be cleaned and/or reconnected to a new fitting 160, as desired.

Any of the assemblies described herein may be provided directly on ends of a fluid line, e.g., an IV or other medical line, as described elsewhere herein. Alternatively, the assemblies may be provided as independent components or may be incorporated into other products or devices, e.g., to provide systems for delivering fluids, e.g., within a medical setting.

For example, turning to FIGS. 33A-34B, an exemplary embodiment of a tube holder 1100 is shown that includes an integral valve 1101 similar to the assembly 200 shown in FIGS. 7A-12D. Generally, the tube holder 1100 includes a housing 1102 including an open end 1104 and a closed end 1106, thereby defining a cavity 1108 for receiving a vacuum-sealed test tube or other container (not shown). A needle 1110 is provided in the cavity 1108, e.g., fixed to the closed end 1106 for penetrating a plenum or other penetrable seal on a test tube or container (also not shown). The closed end 1106 may include a hub 1140 including features similar to the backing member 240 shown in FIG. 10A, except that the closed end 1106 replaces the base portion 246. For example, the hub 1140 may include an annular member including slots (not shown) molded with or otherwise extending from the closed end 1106 of the tube holder 1100.

Figure 33A:
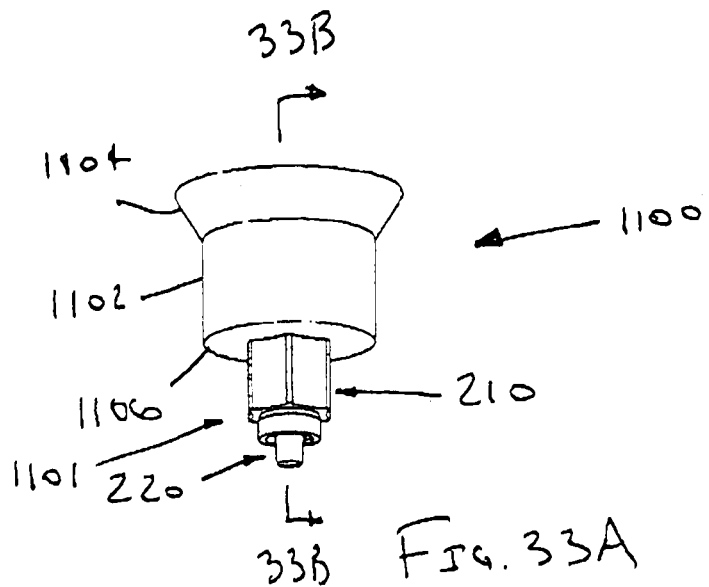
FIGS. 33A and 34A are perspective views of an exemplary embodiment of a tube holder including an integral valve in a deactuated condition and in an actuated condition after being connected to a female Luer fitting, respectively.
Figure 34A:
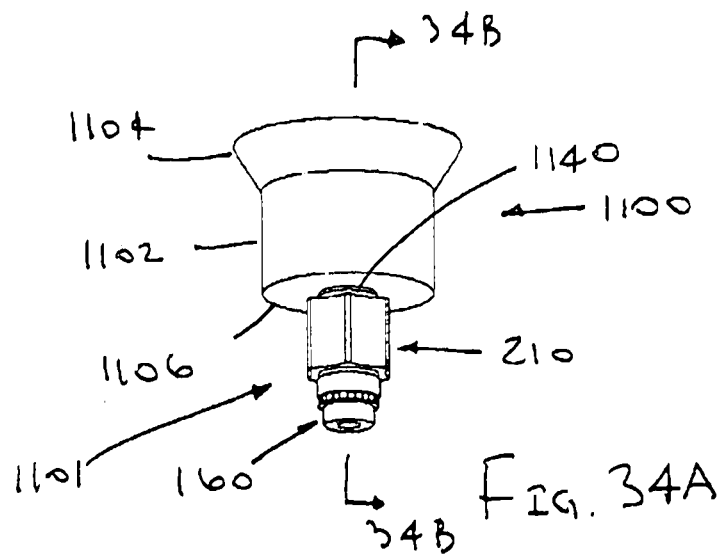
Figure 33B:
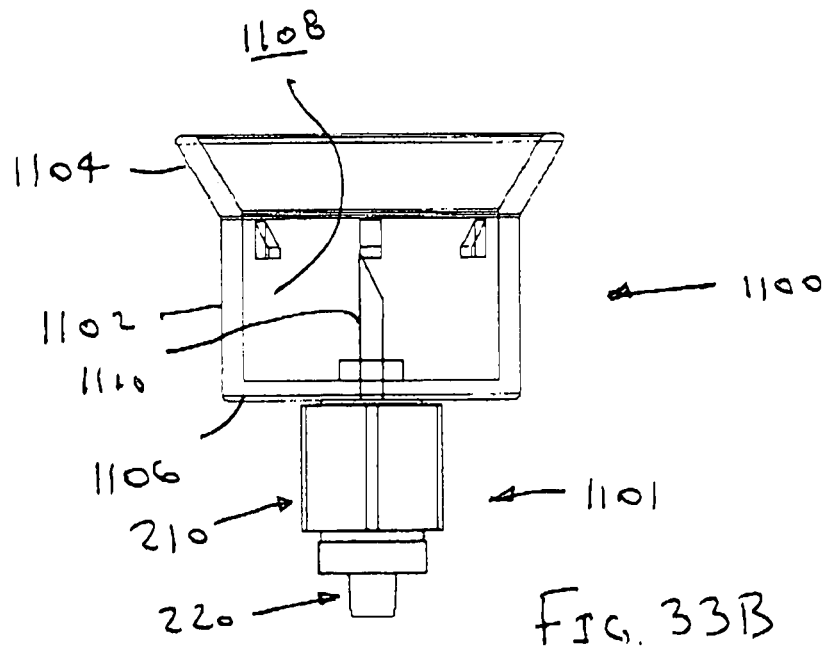
FIGS. 33B and 34B are cross-sectional views of the tube holder of FIGS. 33A and 34A taken along lines 33B-33B and 34B-34B, respectively.
Figure 34B:
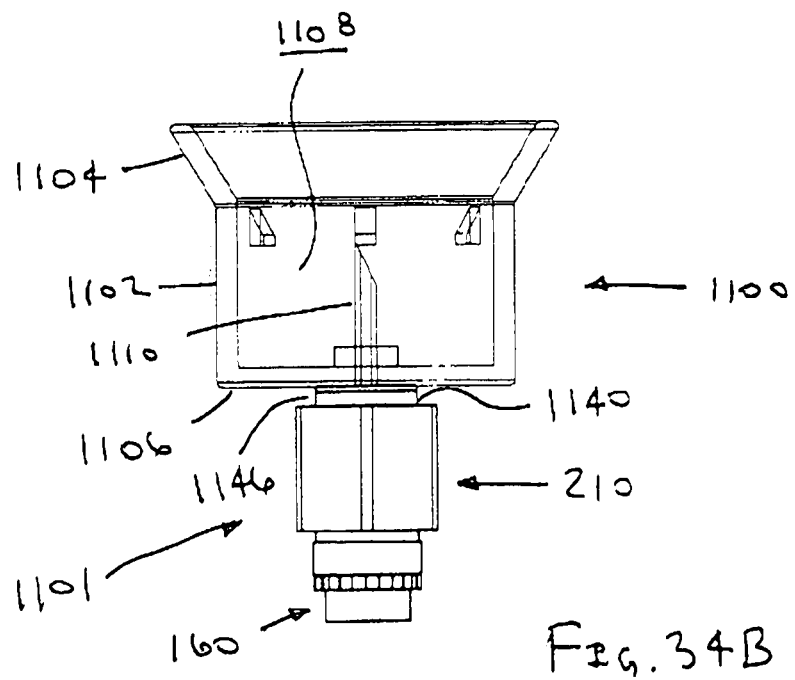
Figure 36A:
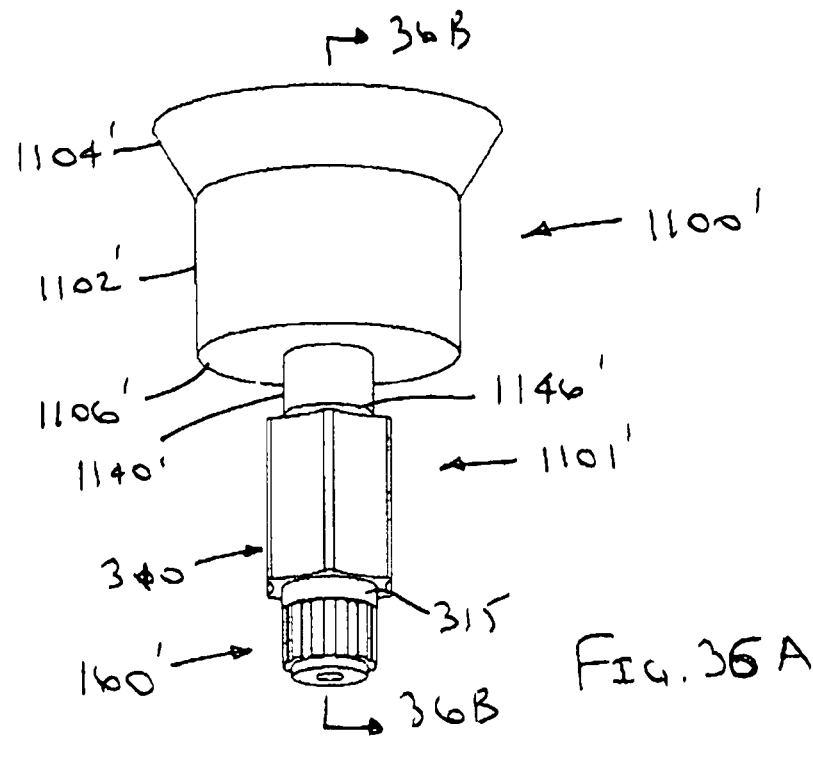
FIGS. 35A and 36A are perspective views of another embodiment of a tube holder in a deactuated condition and in an actuated condition after being connected to a male Luer fitting, respectively.

In addition, the valve 1101 includes an outer shell or bezel 210 including a covering body or inner housing 220, a shaft, camming element, and elastic member (not shown) therein, e.g., which may be connected to the hub 1140, similar to the assembly 200. It will be appreciated that any of the embodiments described herein may be provided for the valve 1101, e.g., including a male or female Luer connection. As shown in FIGS. 33A and 33B, the valve 1101 is in a closed or deactuated condition, i.e., with a fluid path therethrough closed. In contrast, as shown in FIGS. 34A and 34B, a female Luer fitting 160 has been threaded into the bezel 210, thereby actuating the valve 1101. In the actuated condition, a fluid path is opened that communicates from the needle 1110 through the valve 1101 to the female Luer fitting 160, similar to embodiments described elsewhere herein. In the actuated condition, one or more status indicators 1146 may become visible on the hub 1144.

During use, a test tube, vial, or other container (not shown) may be inserted into the open end 1104 of the tube holder 1100, e.g., until the needle 1110 penetrates the seal of the container, thereby communicating with an interior of the container. In this condition, the valve 1101 remains closed, thereby preventing fluid flow into and/or out of the container. The user may then thread the female Luer fitting 160 into the valve 1101, thereby opening the fluid path and allowing fluid to flow through the valve 1101. The user may affirmatively identify that the fluid path is opened when the status indicator(s) 1146 become visible.

For example, the female Luer fitting 160 may be coupled to a fluid line, e.g., a Butterfly needle or other tube communicating with a vein of a patient. When the female Luer fitting 160 is threaded into the valve 1101, the fluid path is opened, which exposes the female Luer fitting 160 (and fluid line) to the vacuum within the container received in the tube holder 1100, thereby pulling blood from the patient's vein through the fluid line and valve 1101, and into the container. When sufficient blood is received within the container, the user may simply unthread the female Luer fitting 160, thereby closing flow through the valve 1101 into the container. If desired, the container may be replaced with another container, and the female Luer fitting 160 connected to fill another container, and the process may be repeated as desired. The valve 1101 may minimize leakage that may otherwise occur when containers are exchanged on a tube holder without the valve 1101.

Turning to FIGS. 35A-36B, another exemplary embodiment of a tube holder 1100' is shown that includes an integral valve 1101' similar to the assembly 300 shown in FIGS. 13A-16B. Similar to the previous embodiment, the tube holder 1100' includes a housing 1102' including an open end 1104,' a closed end 1106,' a cavity 1108' for receiving a container (not shown), and a needle 1110,' e.g., fixed to the closed end 1106' for penetrating a seal on the container (also not shown). The closed end 1106' may include a hub 1140' including features similar to the backing member 340 shown in FIGS. 14A, 14B.

Figure 35A:
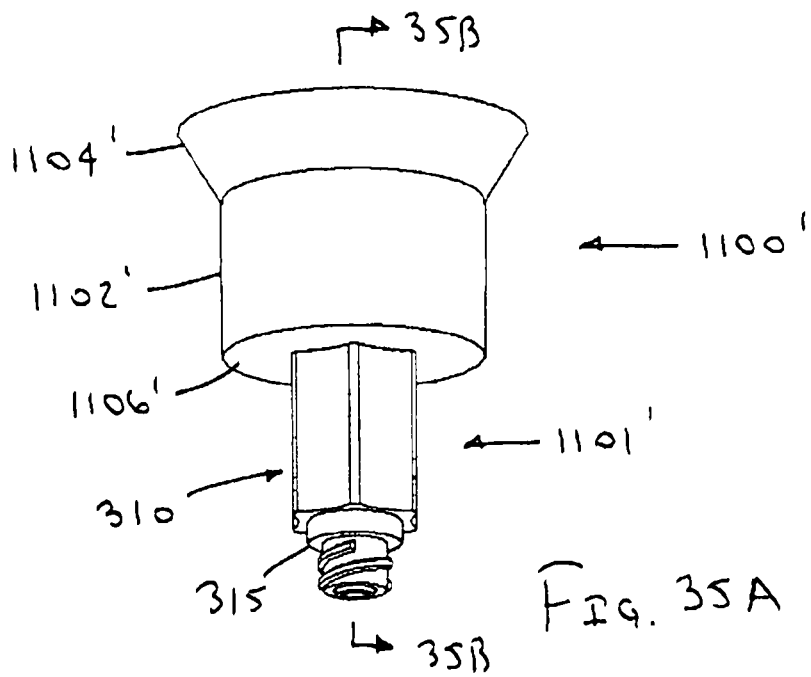
Figure 36B:
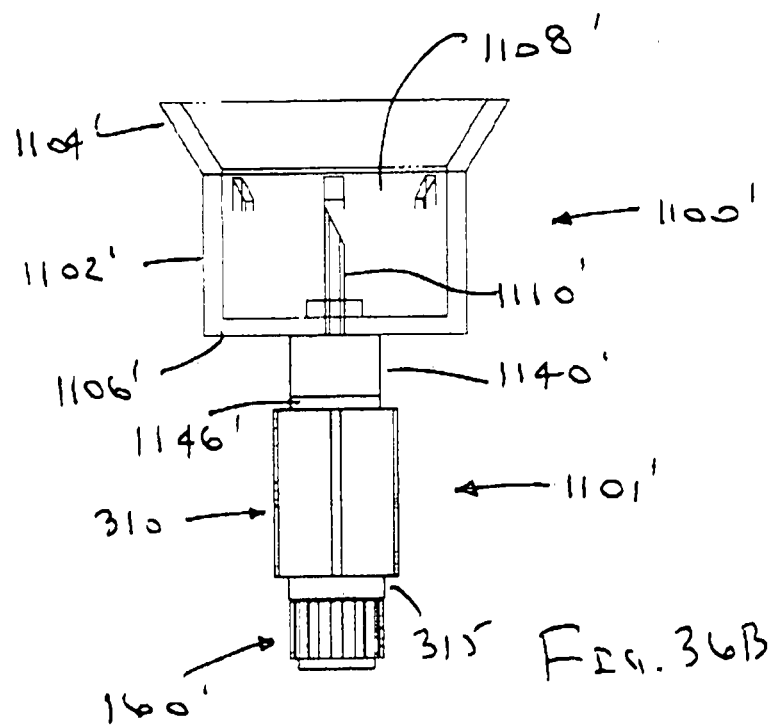
FIGS. 35B and 36B are cross-sectional views of the tube holder of FIGS. 35A and 36A taken along lines 35B-35B and 36B-36B, respectively.
Figure 35B:
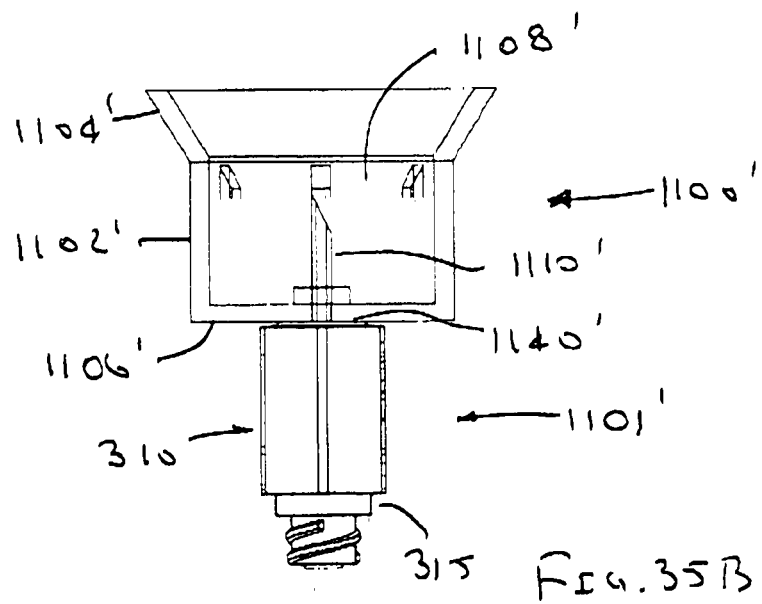

In addition, the valve 1101' includes an outer shell or bezel 310 including a covering body, shaft, camming element, and elastic member (not shown) therein, e.g., which may be connected to the hub 1140,' similar to the assembly 300. It will be appreciated that any of the embodiments described herein may be provided for the valve 1101, e.g., including a male or female Luer connection. As shown in FIGS. 35A and 35B, the valve 1101' is in a closed or deactuated condition, i.e., with a fluid path therethrough closed, while in FIGS. 36A and 36B, a male Luer fitting 160' has been threaded onto the proximal end 315 of the bezel 310, thereby actuating the valve 1101.' In the actuated condition, a fluid path is opened that communicates from the needle 1110 through the valve 1101 to the female Luer fitting 160, similar to embodiments described elsewhere herein.

Operation of the tube holder 1100' and valve 1101' are similar to the previous embodiment. For example, a container (not shown) may be inserted into the open end 1104' of the tube holder 1100,' e.g., until the needle 1110' penetrates the seal of the container. In this condition, the valve 1101' remains closed, thereby preventing fluid flow into and/or out of the container. The user may then thread the male Luer fitting 160' onto the valve 1101,' thereby opening the fluid path and allowing fluid to flow through the valve 1101.' The user may affirmatively identify that the fluid path is opened when the status indicator(s) 1146' become visible.

Turning to FIGS. 37A-38B, another embodiment of a device including an integral valve 1201 is shown. In this embodiment, the device is a syringe 1200 that includes a barrel 1202 including an open proximal end 1204, a substantially closed distal end 1206, and defining a chamber 1208 therein. A plunger 1210 is slidably disposed in the chamber 1208, e.g., that may be withdrawn to draw fluid into the chamber 1208 through the distal end 1206 and/or that may be depressed to eject fluid in the chamber 1208 out through the distal end 1206. The distal end 1206 includes a hub 1240 similar to the hub 1140 of the tube holder 1100 described above, e.g., including features similar to the backing member 240 shown in FIG. 10A, except that the closed end 1206 replaces the base portion 246. For example, the hub 1240 may include an annular member including slots (not shown) molded with or otherwise extending from the closed end 1206 of the syringe 1200.

Figure 38A:
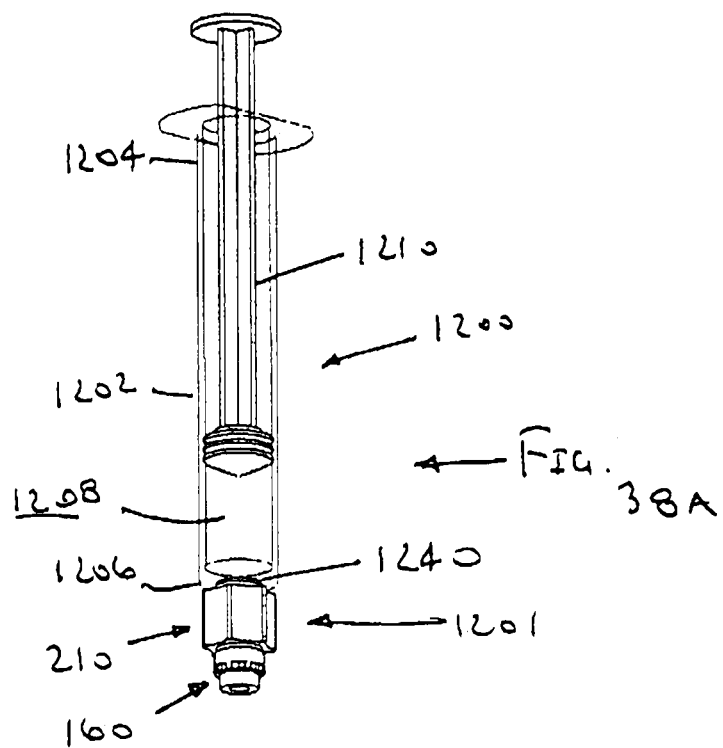
Figure 37A:
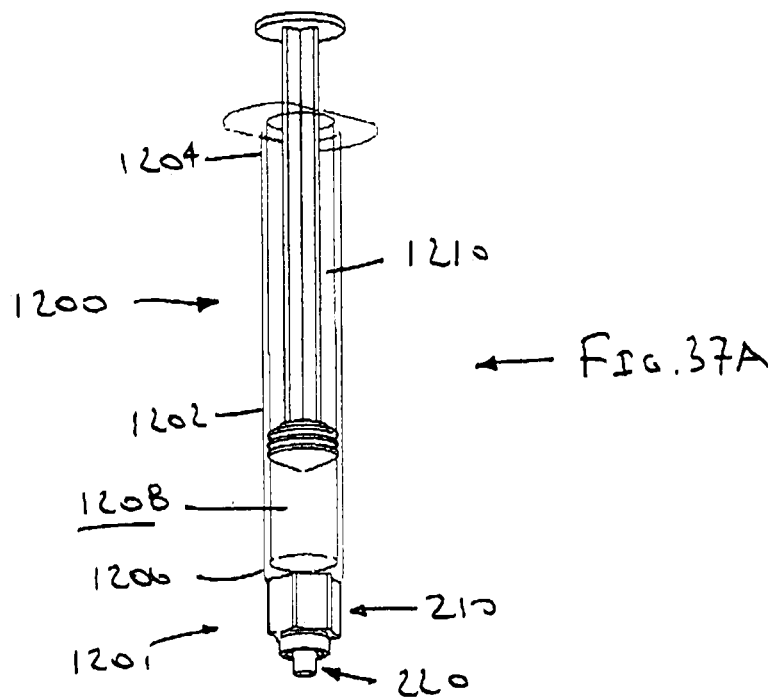

The valve 1201 includes an outer shell or bezel 210 including a covering body or inner housing 220, a shaft, camming element, and elastic member (not shown) therein, e.g., which may be connected to the hub 1240, similar to the assembly 200. It will be appreciated that any of the embodiments described herein may be provided for the valve 1201, e.g., including a male or female Luer connection. As shown in FIGS. 37A and 37B, the valve 1201 is in a closed or deactuated condition, i.e., with a fluid path therethrough closed. In contrast, as shown in FIGS. 38A and 38B, a female Luer fitting 160 has been threaded into the bezel 210, thereby actuating the valve 1201. In the actuated condition, a fluid path is opened that communicates from the chamber 1208 of the syringe 1200 through the valve 1201 to the female Luer fitting 160, similar to embodiments described elsewhere herein. In the actuated condition, one or more status indicators 1246 may become visible on the hub 1244.

During use, the syringe 1200 may be provided preloaded with a desired therapeutic and/or diagnostic fluid within the chamber 1208 of the barrel 1202, e.g., with the plunger 1210 in a proximal position. In this condition, the valve 1201 remains closed, thereby preventing the fluid from flowing out of the syringe 1200. Thus, unlike conventional syringes, the valve 1210 may prevent inadvertent advancement of the plunger 1210, which would otherwise allow fluid to be ejected or otherwise escape from the chamber 1208.

When it is desired to deliver the fluid, the user may then thread the female Luer fitting 160 into the valve 1201, thereby opening the fluid path through the valve 1201. The user may then depress the plunger 1210 distally, thereby ejecting the fluid from the chamber 1208 through the valve 1201 and female Luer fitting 160. For example, the female Luer fitting 160 may be connected to an IV or other fluid line communicating with a vein of a patient, thereby delivering the fluid to the patient. When it is desired to prevent further fluid flow, the user may cease depressing the plunger and/or may unthread the female Luer fitting 160. When the female Luer fitting 160 is unthreaded, the valve 1201 is deactuated, thereby again preventing fluid flow from the syringe 1200.

In an alternative embodiment, the syringe 1200 may be provided initially empty, and the valve 1201 may be opened upon connecting a source of fluid to the valve 1201. The plunger 1210 may then be withdrawn to draw fluid into the chamber 1208, e.g., immediately before delivery to a patient. Once sufficient fluid is loaded into the syringe 1200, the fluid may be delivered as described above. The valve 1201 may allow fluids to be loaded into and/or delivered from the syringe 1200 with enhanced safety over conventional syringes.

Figure 14A:
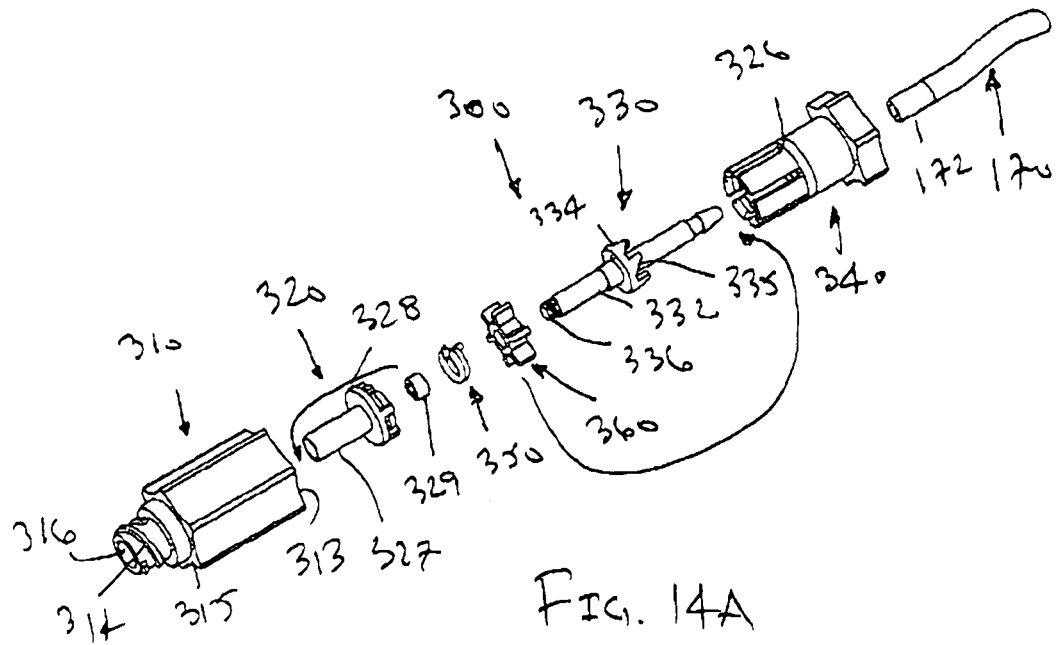
FIGS. 14A and 14B are exploded perspective views of the assembly of FIGS. 13A-13C.
Figure 14B:
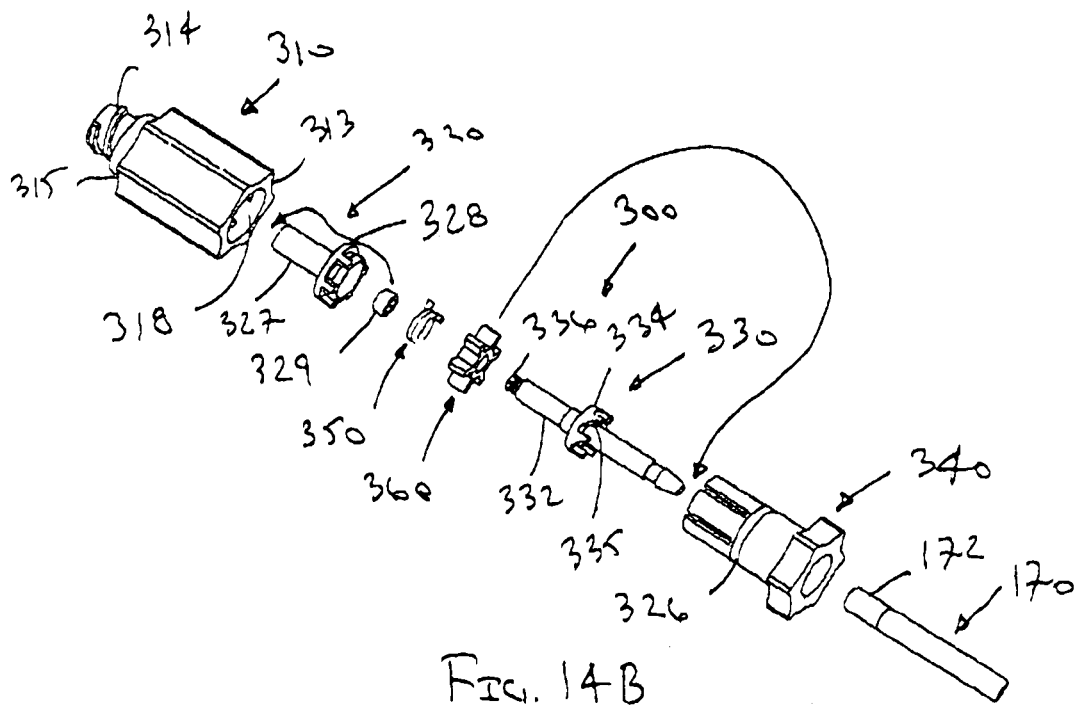
Figure 15B:
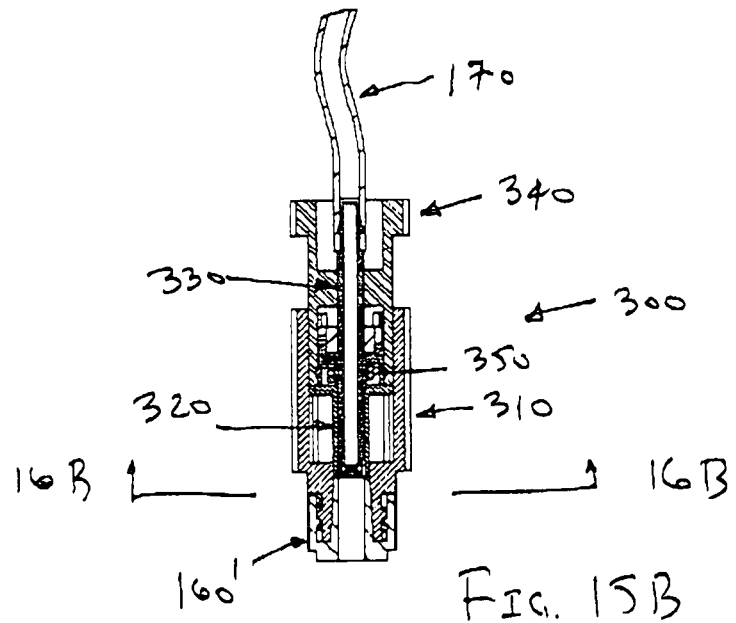
FIGS. 15A and 15B are cross-sectional views of the assembly of FIGS. 13A-13C before and after actuation, respectively.
Figure 15A:
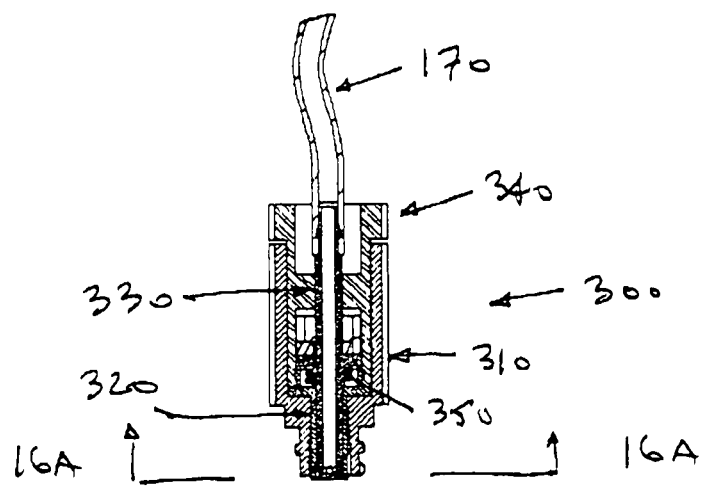
Figure 16A:
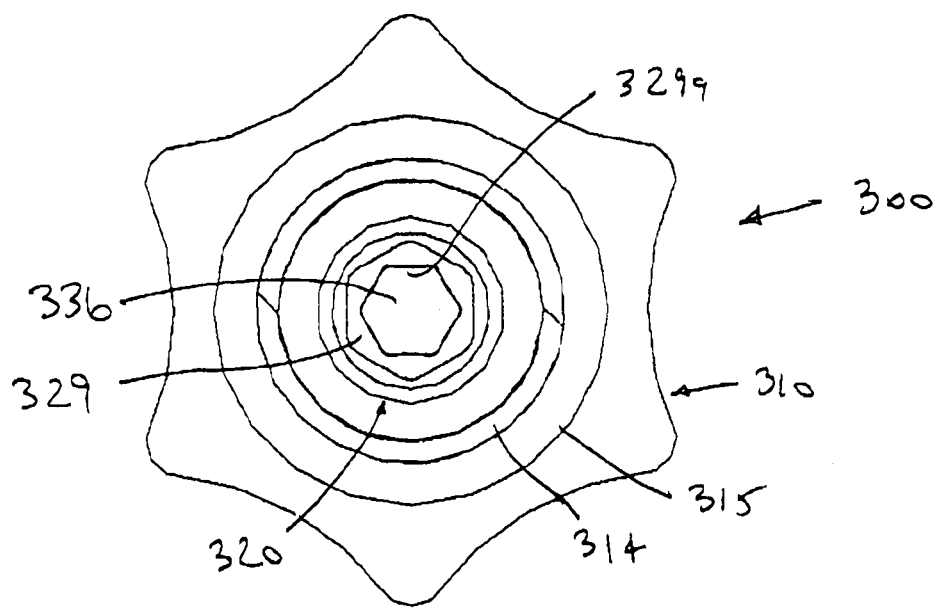
FIGS. 16A and 16B are cross-sectional views of the assembly of FIGS. 15A and 15B, taken along lines 16A-16A and 16B-16B, respectively.
Figure 16B:
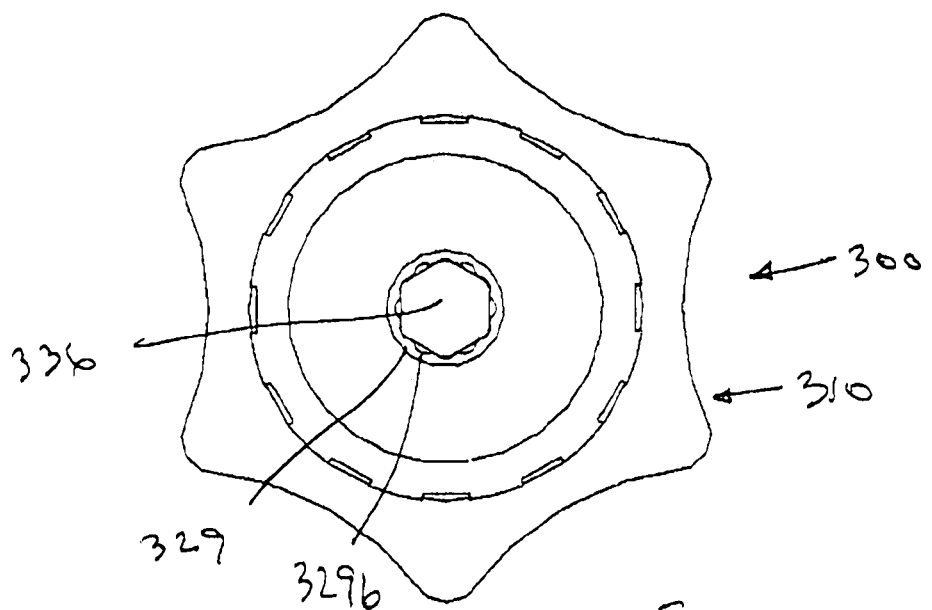
Figure 17A:
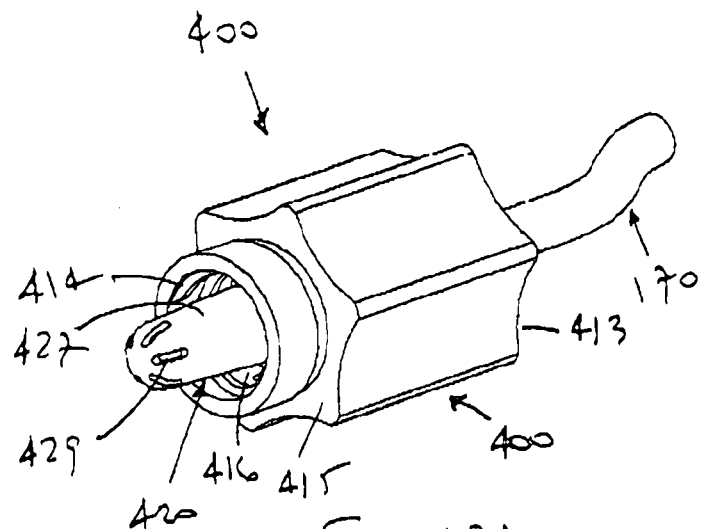
FIG. 17A is a perspective view of still another embodiment of a passive connecting assembly including an outer shell with a male Luer thread connected to an distal end of a length of tubing.
Figure 17B:
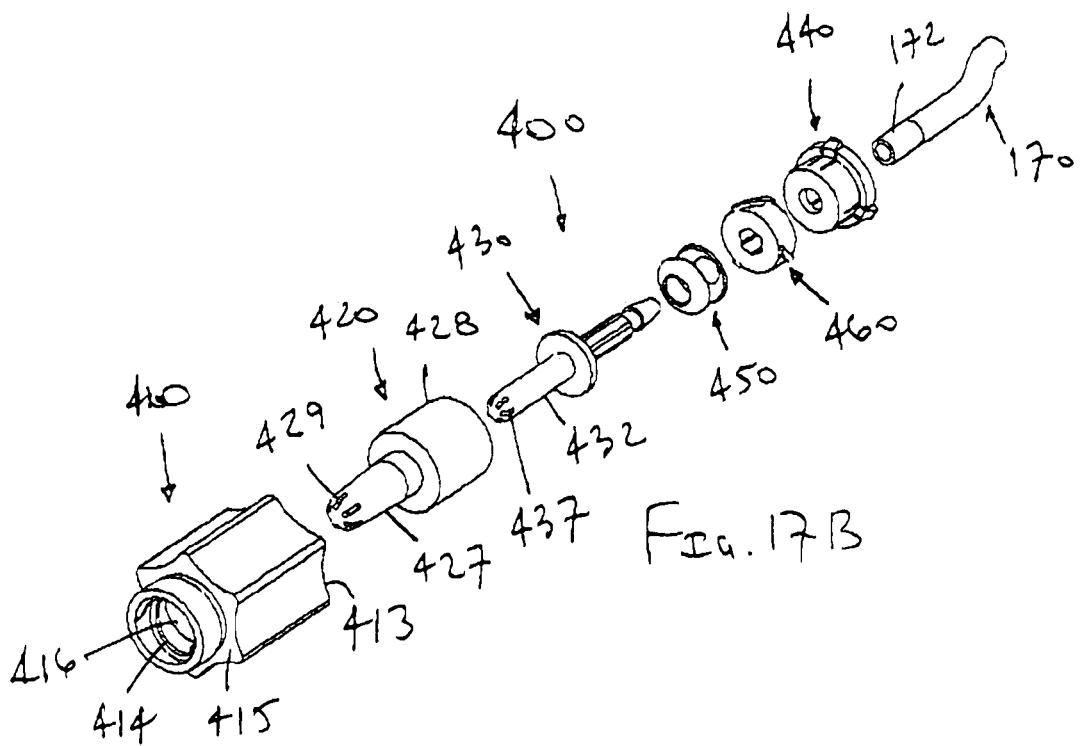
FIGS. 17B and 17C are exploded views of the assembly of FIG. 17A, including an outer shell with a proximal throughbore containing a Luer thread and a distal throughbore; a covering body including a male boss with openings and an outer mating surface; a shaft with an elastic member and a mating member; a camming element; and a backing member.
Figure 17C:
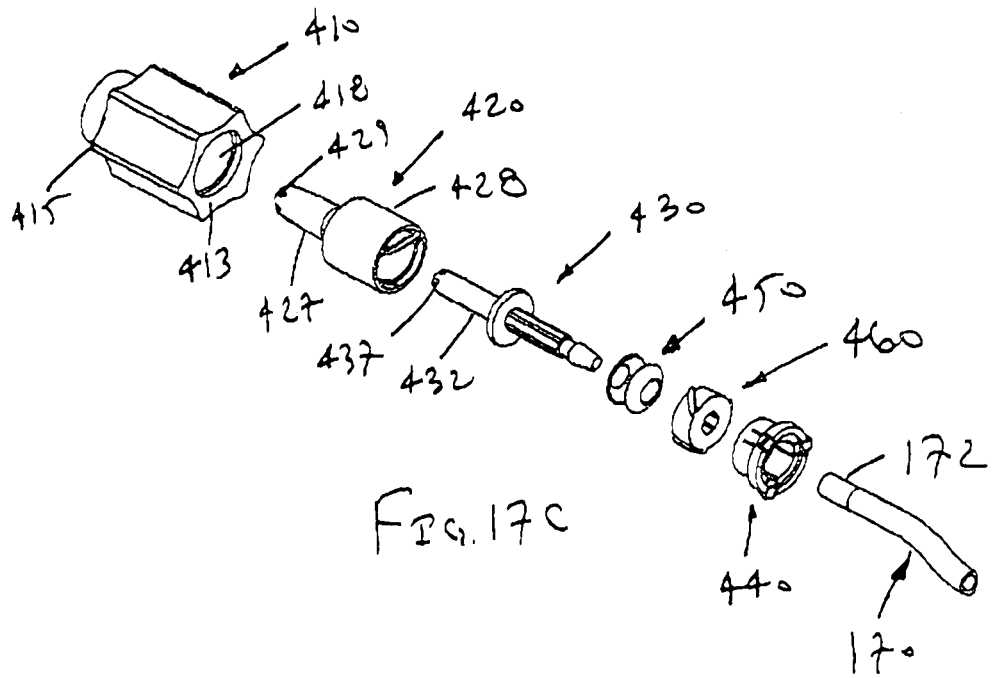
Figure 18:
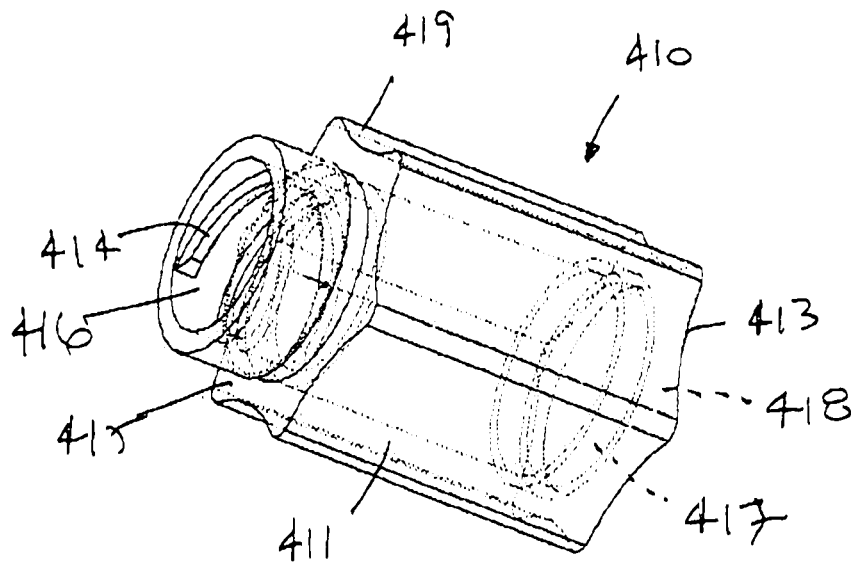
FIG. 18 is a perspective view of the outer shell of the assembly of FIGS. 17A-17C.
Figure 19:
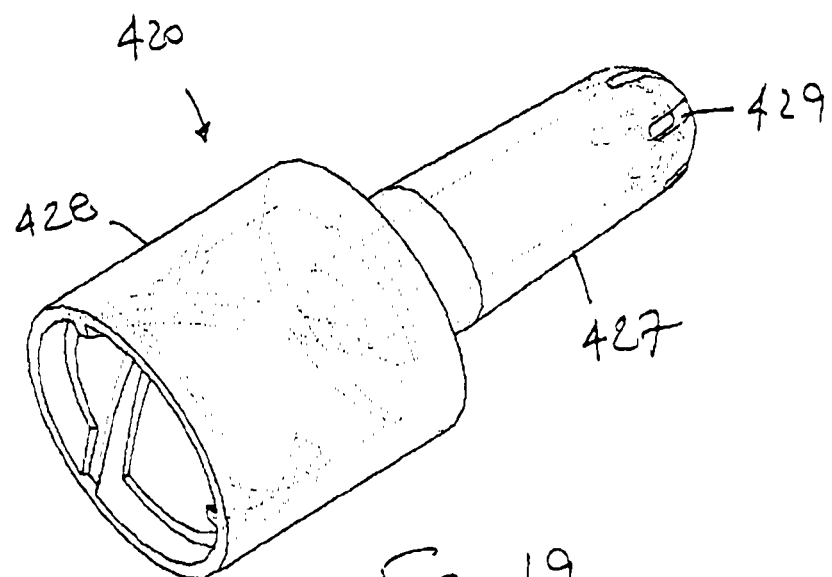
FIG. 19 is a perspective view of the covering body of the assembly of FIGS. 17A-17C.
Figure 20:
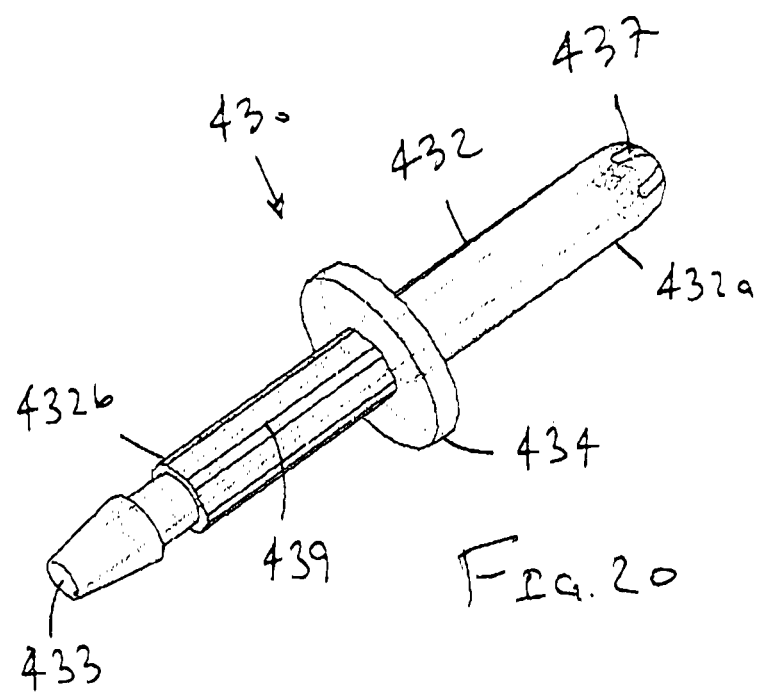
FIG. 20 is a perspective view of the shaft of the assembly of FIGS. 17A-17C.
Figure 21A:
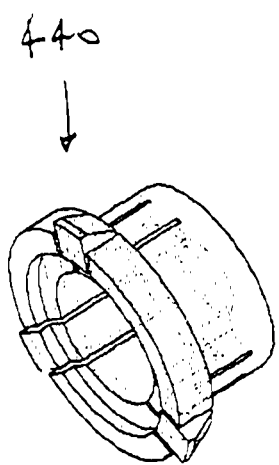
FIG. 21A is a perspective view of a backing member of the assembly of FIGS. 17A-17C.
Figure 21B:
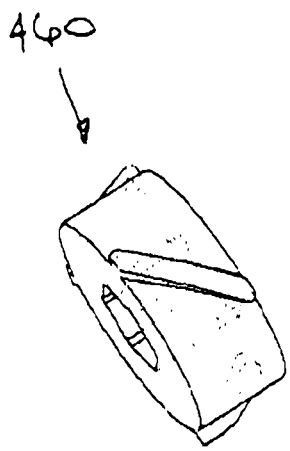
FIG. 21B is a perspective view of a camming element of the assembly of FIGS. 17A-17C.
Figure 22A:
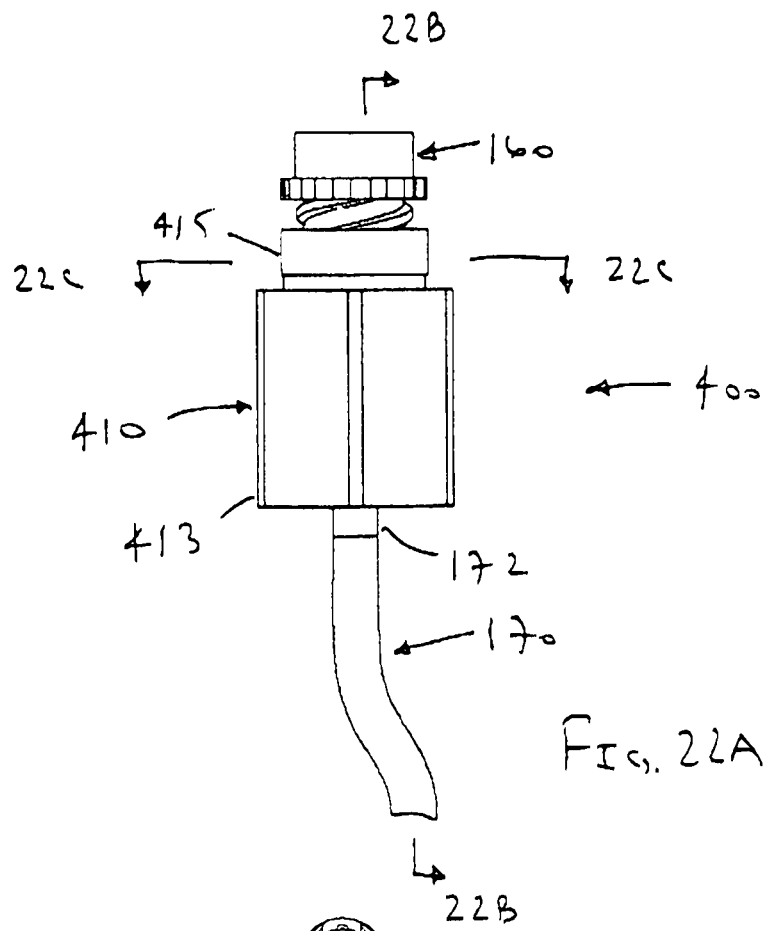
FIG. 22A is a side view of the assembly of FIGS. 17A-17C in a deactuated condition before a Luer fitting has been connected to the assembly.
Figure 22B:
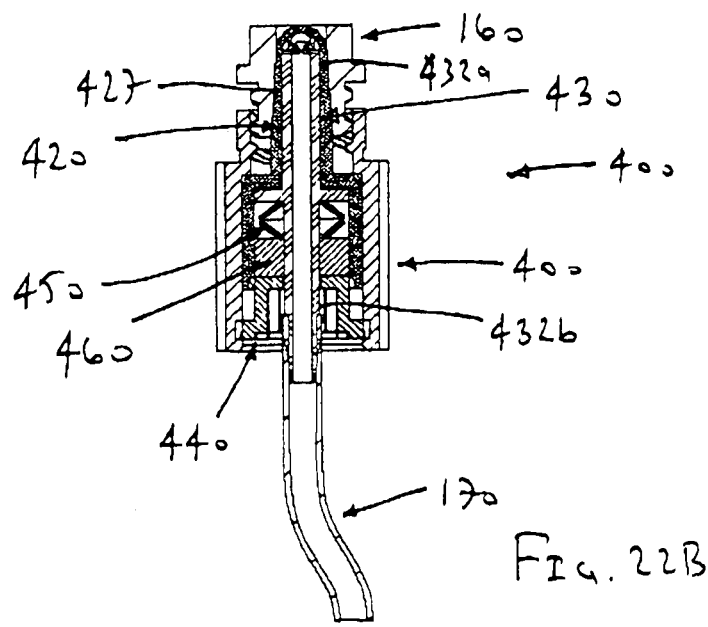
FIGS. 22B and 22C are cross-sectional views of the assembly of FIG. 22A, taken along lines 22B-22B and 22C-22C, respectively.
Figure 22C:
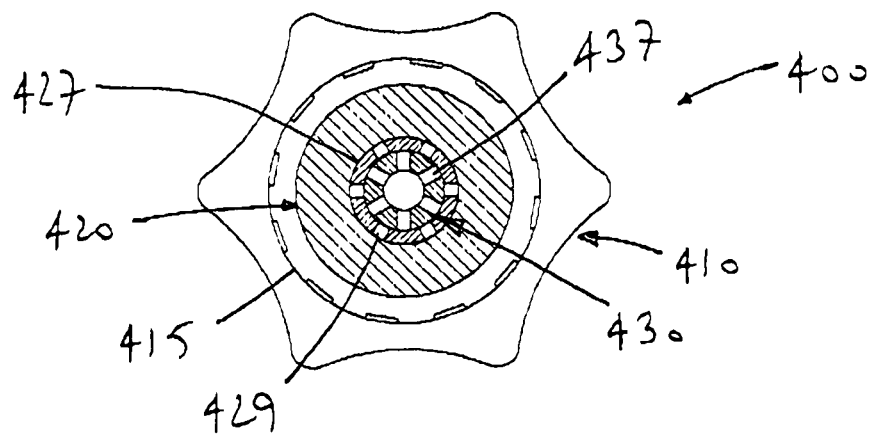
Figure 22D:
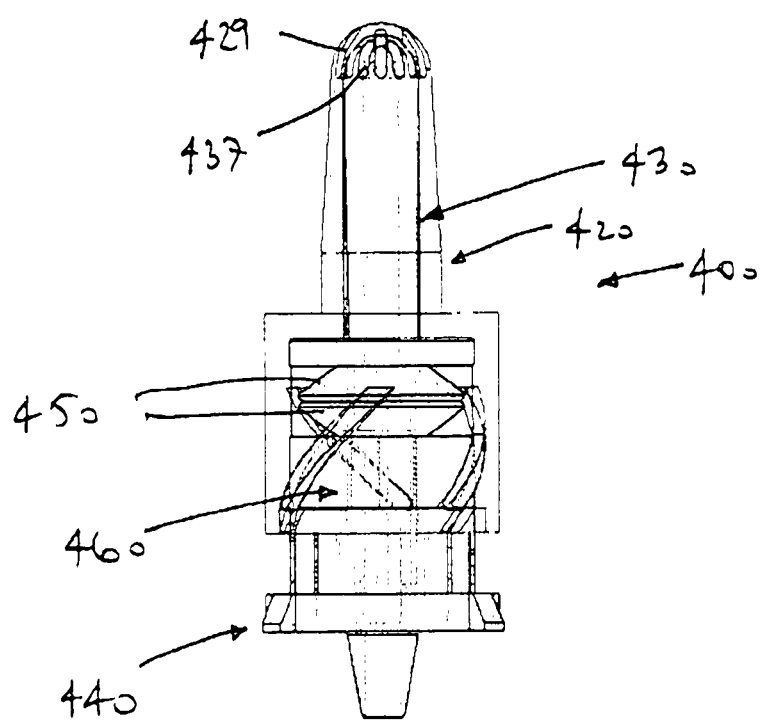
FIG. 22D is a side view of the assembly of FIG. 22A with the outer shell removed to show the position of the internal components of the assembly before actuation.

Turning to FIGS. 39A-40B, another embodiment of a syringe 1200' is shown that includes an integral valve 1201.' Similar to the previous embodiment, the syringe 1200' includes a barrel 1202' including an open proximal end 1204,' a substantially closed distal end 1206,' a chamber 1208,' and a plunger 1210' slidable in the chamber 1208.' The distal end 1206' includes a hub 1240' similar to the hub 1140' of the tube holder 1100' described above, e.g., including features similar to the backing member 340 shown in FIGS. 14A, 14B.

In addition, the valve 1201' includes an outer shell or bezel 310 including a covering body, shaft, camming element, and elastic member (not shown) therein, e.g., which may be connected to the hub 1240,' similar to the assembly 300.

Figure 40A:
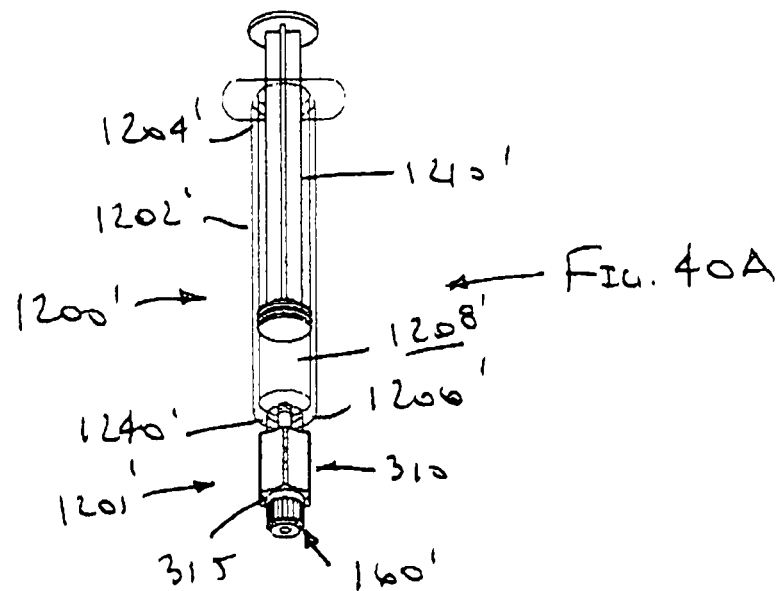
Figure 39A:
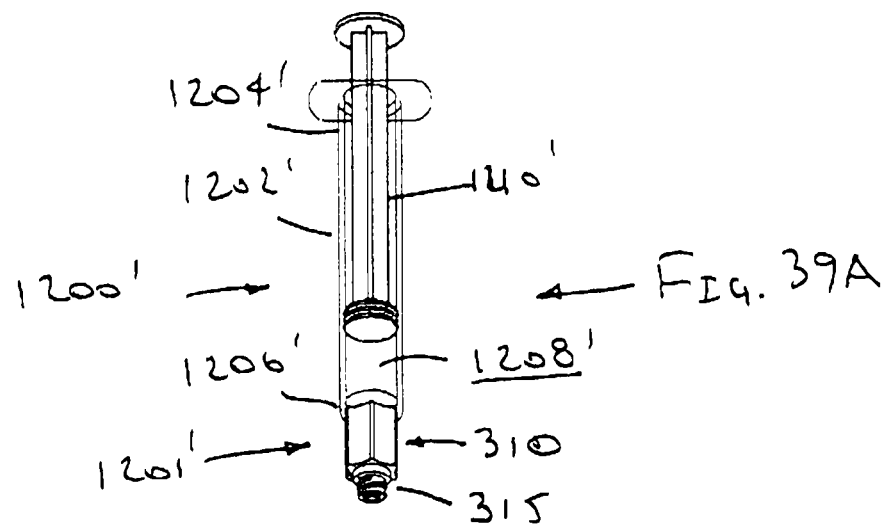

As shown in FIGS. 39A and 39B, the valve 1201' is in a closed or deactuated condition, i.e., with a fluid path therethrough closed, while in FIGS. 40A and 40B, a female Luer fitting 160' has been threaded into the bezel 310, thereby actuating the valve 1201.' Otherwise, the syringe 1200' and valve 1201' may be used similar to the previous embodiment.

Figure 41A:
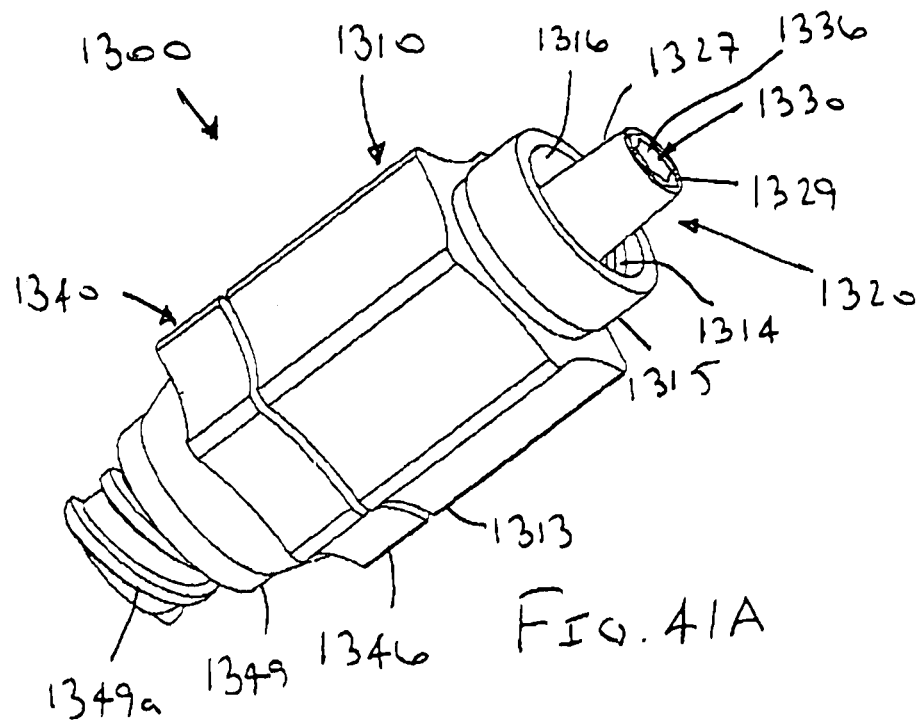
FIGS. 41A, 41B, and 41C are perspective, side, and perspective views, respectively, of an exemplary embodiment of a stand-alone valve assembly for connection to a fluid line.
Figure 41B:
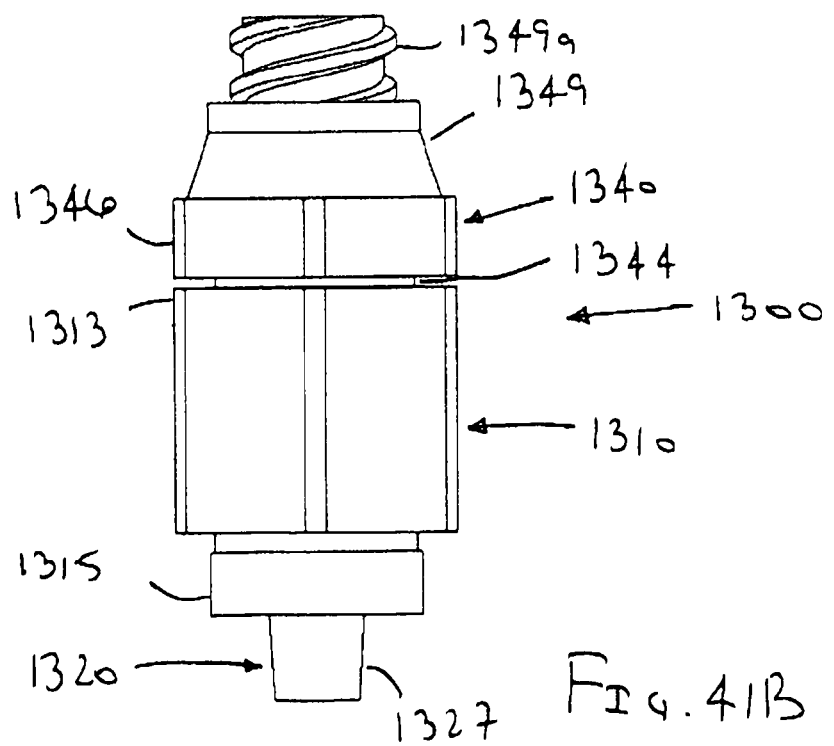
Figure 41C:
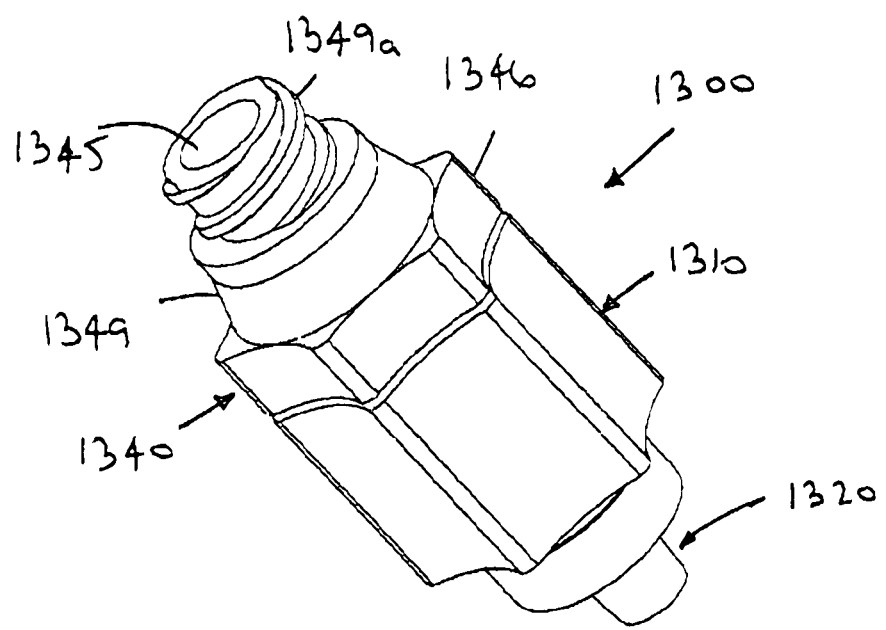

Turning to FIGS. 41A-41C, an exemplary embodiment of a valve assembly 1300 is shown that includes components similar to the assembly 200 shown in FIGS. 7A-12D. Generally, the assembly 1300 includes an outer shell or bezel 1310 and backing member 1340, together providing an outer package or housing for the assembly 1300, a covering body or inner housing 1320, a shaft, core pin, or tubular member 1330

(only partially shown in FIG. 41A), a camming member (not shown), and an elastic member (also not shown).

For example, similar to FIG. 8, the outer shell 1310 includes proximal and distal ends 1315, 1313, a distal throughbore (not shown), and a proximal throughbore 1316 including a male Luer thread 1314 therein, as best seen in FIG. 41A. Similar to FIGS. 7B and 7C, the covering body 1320 includes an elongated male boss 1327 with a deformable membrane 1329 attached thereto, as best seen in FIG. 41A. Similar to the previous embodiments, the covering body 1320 may be received within the outer shell 1310, e.g., by inserting the male boss 1327 through the distal throughbore into the proximal throughbore 1316. Similar to FIGS. 9A and 9B, the shaft 1330 generally includes a throughbore extending between first and second ends of the conduit (not shown), a mating member with a plurality of cam features (not shown), and a fluid cap 1336, only partially seen in FIG. 41A. Finally, similar to FIG. 10A, the backing member 1340 includes a base portion 1346, and an annular portion 1344 extending into the bezel 1310 from the base portion 1346, together defining a throughbore 1345.

Unlike the previous embodiments, the backing member 1340 includes a hub 1349 including a female Luer connector 1349a extending from the base portion 1346 opposite the annular portion 1344. Alternatively, other connectors (not shown) may be provided on the hub 1349 instead of the Luer connector 1349a, as desired.

Before use, the components of the assembly 1300 may be assembled together, e.g., during manufacturing, similar to previous embodiments described herein. For example, a proximal end of the shaft 1330 may be inserted into the covering body 1320 until the fluid cap 1336 is received within the opening of the deformable membrane 1329. The covering body 1320 (with the shaft 1330 therein) may be inserted into the outer shell 1310, e.g., into the distal throughbore until the male boss 1327 enters the proximal throughbore 1316. The camming element (not shown) may be inserted over and around the shaft 1330 and into the distal throughbore of the outer shell 1310, e.g., until the camming element is captured or received within the outer shell 1310. The backing member 1340 may be inserted into the distal end 1313 of the outer shell 1310, e.g., around the shaft 1330 and camming element. This may involve aligning features (not shown) in the annular portion 1344 of the backing member 1340 with corresponding features (also not shown) on the camming element and/or covering body 1320 to secure the backing member 1340 and allow camming of the shaft 1330 during actuation, similar to the assembly 200.

Once assembled, the shaft 1330 may be slidably received within the throughbore of the backing member 1340. For example, the throughbore of the backing member 1340 may be sized to receive a distal end (not shown) of the shaft 1330, e.g., such that the shaft 1330 may rotate relative to the backing member 1340 and may movable axially within the throughbore. The shaft 1330 may extend into the throughbore without extending completely through the backing member 1340, e.g., without extending into the hub 1349. The throughbore of the backing member 1340 and the distal end of the shaft 1330 may be sized to provide a substantially fluid-tight seal therebetween during use of the assembly 1300.

Unlike the assembly 200, the assembly 1300 may be provided as an independent component, which may be connected into a fluid line, as desired. For example, a syringe, tubing, container, and the like may be provided that already include a male Luer fitting (not shown). The connector 1349a may be threaded into the connector, thereby coupling the assembly 1300 to the fluid line, but with the assembly 1300 remaining in the deactuated position, as shown in FIGS. 41A-41C. When desired, e.g., to deliver fluid via the fluid line, another end of the fluid line (also not shown) may be connected to the male Luer connector 1314 on the outer shell 1310, similar to previous embodiments. This action may cause the outer shell 1310 to move proximally, thereby rotating the shaft 1330 within the covering body 1320 and opening the fluid path through the assembly 1300.

Optionally, when a female Luer connector (not shown) is tightened into the proximal end 1315 of the outer shell 1310, a region of the annular portion 1344 of the backing member 1340 may become exposed. If desired, an actuated status indicator (not shown) may be provided on the annular portion 1344, similar to that shown in FIG. 12A, which may become exposed only when the female Luer connector is finally tightened to the outer shell 1310. When it desired to discontinue fluid flow, the female Luer connector may be unthreaded from the outer shell 1310, similar to the previous embodiments.

Figure 42A:
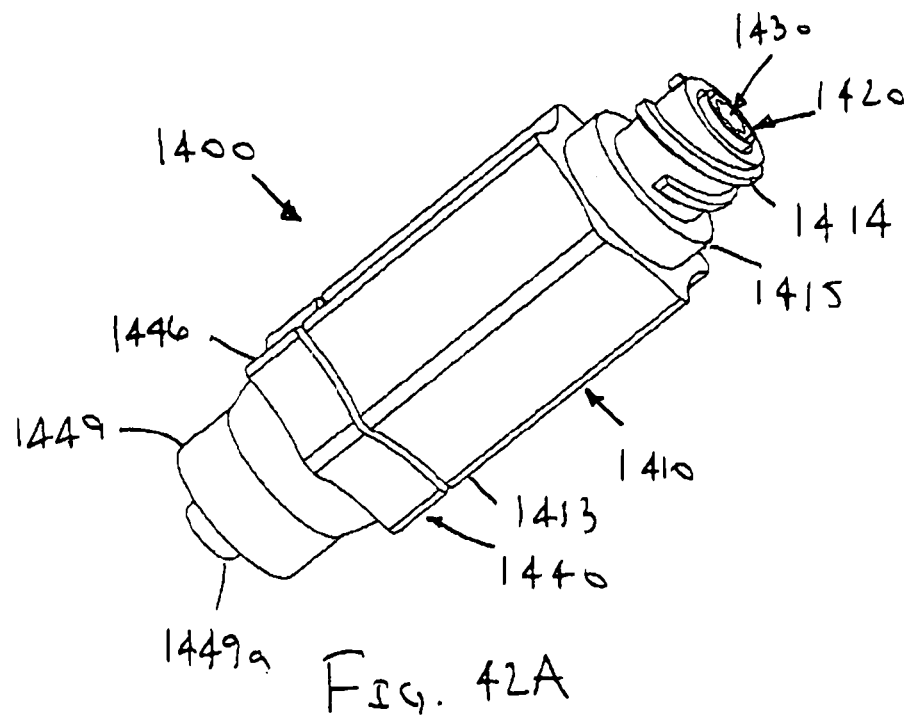
FIGS. 42A, 42B, and 42C are perspective, side, and perspective views, respectively, of another embodiment of a valve assembly for connection to a fluid line.
Figure 42B:
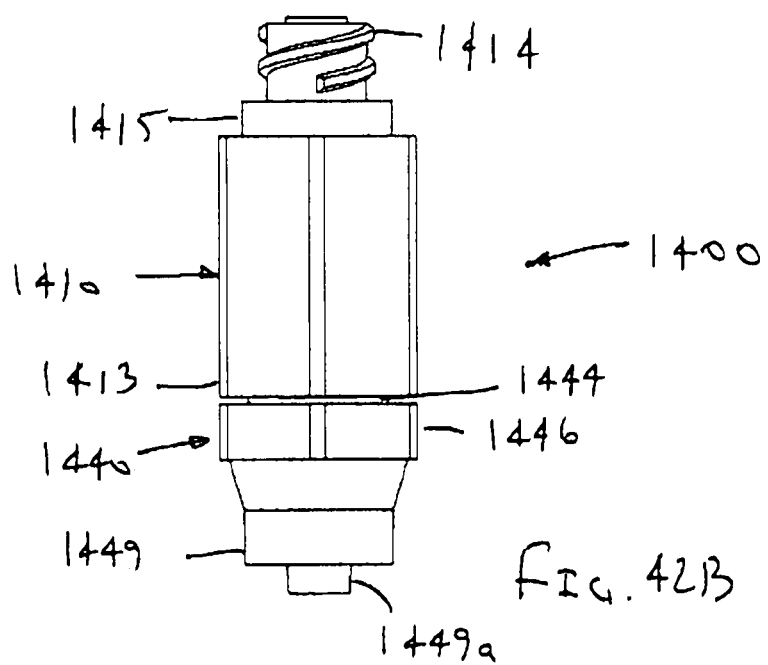
Figure 42C:
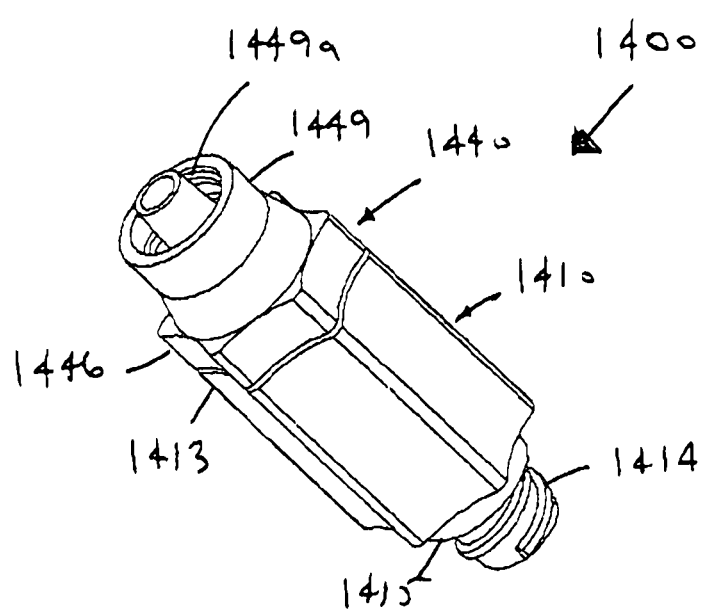

Turning to FIGS. 42A-42C, another embodiment of a valve assembly 1400 is shown that includes components similar to the assembly 300 shown in FIGS. 13A-16B. Generally, the assembly 1400 includes an outer shell or bezel 1410 and backing member 1440, together providing an outer package or housing for the assembly 1400, a covering body or inner housing 1420, a shaft, core pin, or tubular member 1430 (only partially shown in FIG. 42A), a camming member (not shown), and an elastic member (also not shown).

Unlike the assembly 300, the backing member 1440 includes a hub 1449 including a male Luer connector 1449a extending from the base portion 1446 opposite the annular portion 1444. Alternatively, other connectors (not shown) may be provided on the hub 1449 instead of the Luer connector 1449a, as desired. Otherwise, assembly and use of the assembly 1400 is similar to other embodiments described elsewhere herein.

Figure 43A:
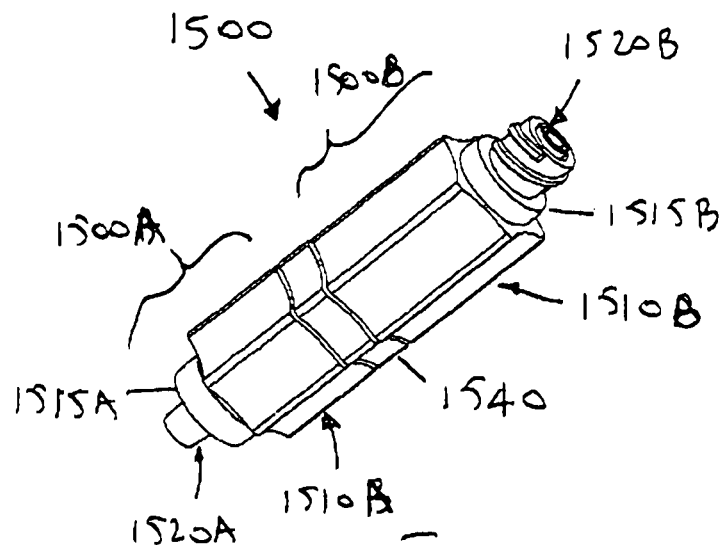
FIGS. 43A, 43B, and 43C are perspective, side, and perspective views, respectively, of an exemplary embodiment of a dual valve assembly for connection to a fluid line.
Figure 43B:
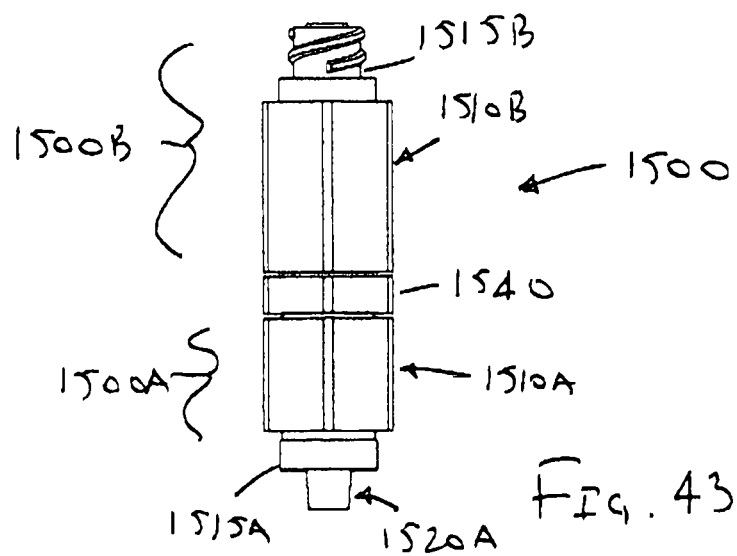
Figure 43C:
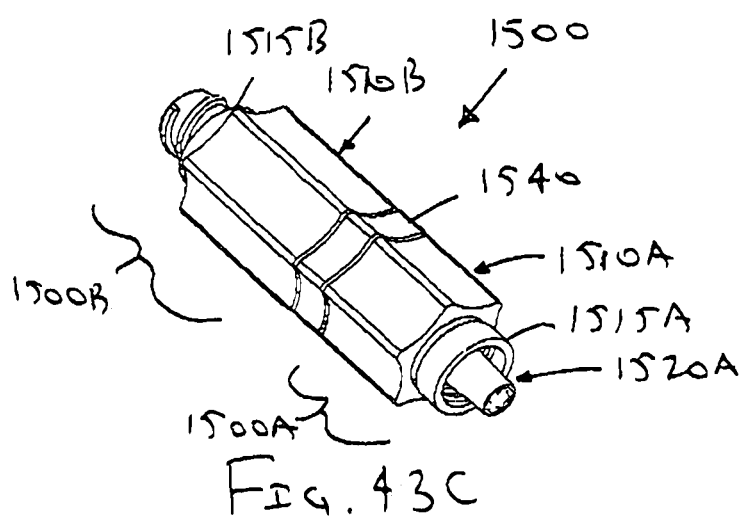

Turning to FIGS. 43A-43C, an exemplary embodiment of a dual valve assembly 1500 is shown. Generally, the assembly 1550 includes a pair of valves that share a common backing member 1540 and fluid path. In the embodiment shown, a first valve 1500A is provided, which may be similar to the assembly 200 shown in FIGS. 7A-12D, and a second valve 1500B is provided, which may be similar to the assembly 300 shown in FIGS. 13A-16B. Generally, each valve 1500A, 1500B includes an outer shell or bezel 1510A, 1510B, a covering body or inner housing 1520A, 1520B, a shaft, a camming member, and an elastic member (not shown) within the respective bezel 1510A, 1510B. The components of each valve 1500A, 1500B may be assembled together on respective sides of the backing member 1540, which includes appropriate features for connecting the components and allowing each valve 1500A, 1500B to be operated independently of the other.

The fluid path through the assembly 1500 may remain substantially closed until both valves 1500A, 1500B are actuated, i.e., secured to respective ends of a fluid line (not shown). For example, a female Luer fitting (not shown) may be threaded into the male Luer connector 1515A of the first valve 1500A, which may actuate the first valve 1500A. However, because the second valve 1500B is still closed, the fluid path through the assembly 1500 remains closed. When a male Luer fitting (not shown) is then threaded over the female Luer connector 1515B, the second valve 1500B may be actuated, thereby opening the fluid path and allowing fluid to flow through the fluid line via the assembly 1500. For example, the female Luer fitting may be connected to tubing communicating with a source of fluid (not shown), while the male Luer fitting may be connected to tubing communicating with a patient, e.g., to an infusion set previously placed in the patient's vein. With both valves 1500A, 1500B actuated, fluid may flow from the source through the assembly 1500 and into the patient.

One potential advantage of the assembly 1500 is that it may create a desired pressure within the fluid line when the valves 1500A, 1500B are actuated and/or deactuated. For example, it may be desirable to create a positive or negative pressure within the fluid path through the assembly 1500 during connection or disconnection from the fluid line. As an example, in some applications, it may be desirable to create a slight negative pressure within the assembly 1500 during disconnection, e.g., to draw any residual fluid into the assembly 1500 and reduce the risk of exposure of the residual fluid to the surrounding environment, e.g., to the user, patient, and the like. Alternatively, in some applications, it may be desirable to create a slight positive pressure during disconnection to eject any residual fluid from within the fluid path of the assembly 1500, e.g., to reduce coagulation of blood or other fluid within the assembly 1500 between fluid delivery. In another alternative, the valves 1500A, 1500B may be configured to create a net substantially zero pressure change during connection and/or disconnection.

In the exemplary assembly 1500 of FIGS. 43A-43C, either of actuation and deactuation of the valves 1500A, 1500B creates a substantially net zero pressure change within the fluid path. It will be appreciated that other embodiments of valves, such as the assemblies described elsewhere herein may be provided for either of the valves 1500A, 1500B.

Figure 44A:
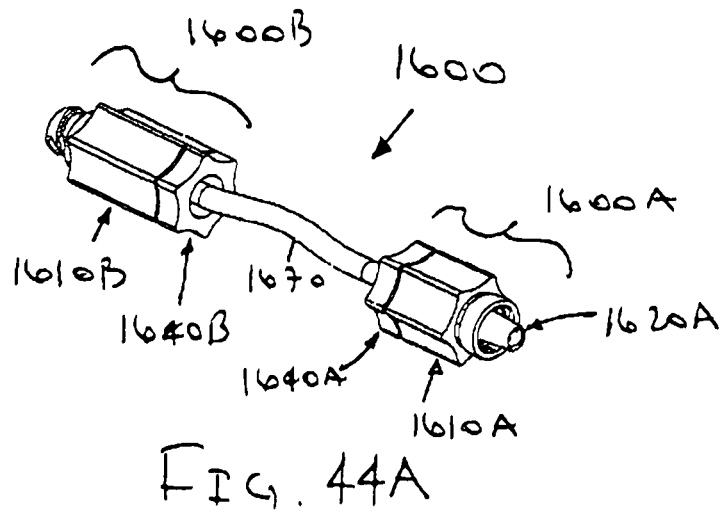
FIGS. 44A, 44B, and 44C are perspective, side, and perspective views, respectively, of another embodiment of a dual valve assembly for connection to a fluid line.
Figure 44B:
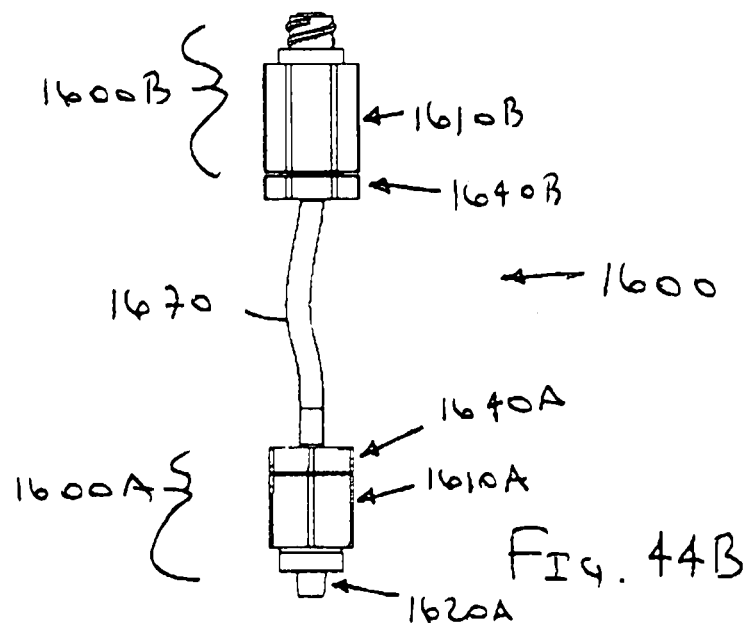
Figure 44C:
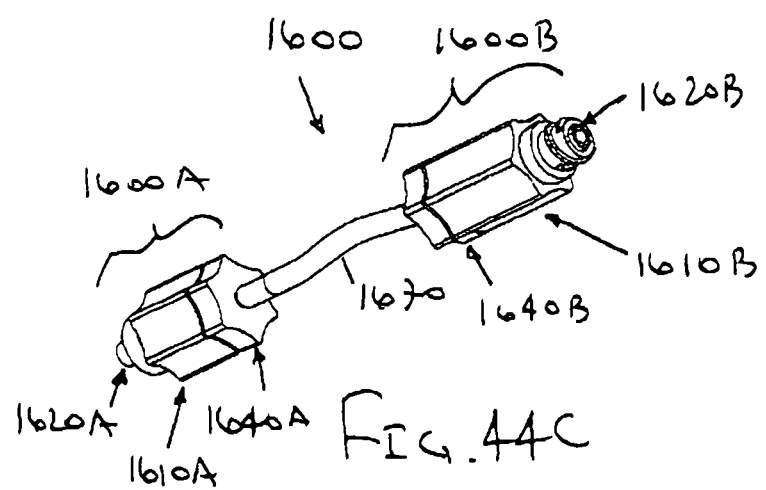

Turning to FIGS. 44A-44C, another embodiment of a dual valve assembly 1600 is shown that may generally operate similar to the dual valve assembly 1500 shown in FIGS. 43A-43C. The assembly 1600 includes a first valve 1600A, which may be similar to the assembly 200 shown in FIGS. 7A-12D, and a second valve 1600B is provided, which may be similar to the assembly 300 shown in FIGS. 13A-16B. Generally, each valve 1600A, 1600B includes an outer shell or bezel 1610A, 1610B, a backing member 1640A, 1640B, a covering body or inner housing 1620A, 1620B, a shaft, a camming member, and an elastic member (not shown). The components of each valve 1600A, 1600B may be assembled together independently of the other, unlike the preceding embodiment. Instead, respective ends of a length of tubing 1670 may be connected to the valves 1600A, 1600B. e.g., to the respective shafts and/or backing members, similar to the previous embodiments.

Each valve 1600A, 1600B may be connected to a fluid line, e.g., to a female Luer fitting and male Luer fitting, respectively. With one or both valves 1600A, 1600B deactuated, the fluid path through the assembly 1600 may remain substantially closed. Thus, fluid may only flow when both valves 1600A, 1600B are actuated, i.e., engaged to respective ends of a fluid line and opened. Similar to the previous embodiment, the configuration of the valves 1600A, 1600B may be selected to provide a net pressure differential within the fluid path during actuation and/or deactuation, as desired.

The foregoing disclosure of the exemplary embodiments has been presented for purposes of illustration and description. It is not intended to be exhaustive or to limit the invention to the precise forms disclosed. Many variations and modifications of the embodiments described herein will be apparent to one of ordinary skill in the art in light of the above disclosure. For example, elimination of some components, such as the flexible sleeve that deforms in actuation, is possible and within the scope of the present invention. Another method may include allowing the core to rotate and deform the tip of the male Luer without the need for a sleeve. The scope of the invention is to be defined only by the claims appended hereto, and by their equivalents.

Further, in describing representative embodiments, the specification may have presented the method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

I claim:

1. A connector assembly for controlling flow in a fluid line, comprising:
   an outer shell comprising a first end, a second end, and a passage extending therebetween, the first end comprising a connector for connecting the assembly to a fluid line;
   an inner housing disposed within the outer shell and comprising a boss disposed adjacent the first end, the inner housing being movable axially within the outer shell between a first position adjacent the first end and a second position further from the first end than the first position when a device is connected to the connector on the first end of the outer shell;
   a tubular member disposed within the inner housing and comprising a fluid passage therein extending between the second end of the outer shell and the boss of the inner housing, the tubular member carried by the inner housing such that the tubular member moves axially as the inner housing moves between the first and second positions; and
   a cam mechanism configured for causing the tubular member to rotate as the inner housing moves between the first and second positions, thereby opening a fluid path between the fluid passage in the tubular member and the first end of the outer shell to allow fluid flow through the assembly with the device connected to the first end of the outer shell.

2. The assembly of claim 1, further comprising a backing member, and wherein the inner housing is attached to the backing member, and wherein the outer shell is movable axially and rotationally relative to the backing member.

3. The assembly of claim 2, wherein the tubular member comprises a camming member coupled to a shaft, the camming member comprising the cam features cooperating with cam features on the inner housing such that axial movement of the inner housing member relative to the outer shell causes the camming member to rotate relative to the inner housing, thereby causing the shaft to rotate relative to the inner housing.

4. The assembly of claim 2, further comprising a syringe having a barrel, the barrel having a distal end and a proximal end, the backing member comprising part of the distal end of the syringe barrel.

5. The assembly of claim 1, further comprising:
a backing member coupled to the second end of the outer shell such that the outer shell is substantially axially fixed relative to the backing member and rotatable relative to the backing member, the backing member slidably coupled to the inner housing such that the inner housing moves helically relative to the backing member when the inner housing is directed from the first position towards the second position;
the tubular member being slidably coupled to the backing member such that the tubular member is substantially rotationally fixed relative to the backing member and is movable axially relative to the backing member, the tubular member comprising a fluid passage therein extending between the first and second ends;
a seal on the boss that engages the first end of the tubular member in the first position to substantially seal the fluid passage; and
the cam mechanism comprising cam features on the inner housing and the tubular member for coupling axial movement of the tubular member to axial movement of the inner housing when the inner housing is initially moved from the first position towards the second position, the cam features causing the tubular member to move distally relative to the inner housing immediately before the inner housing reaches the second position, thereby disengaging the seal from the first end of the tubular member and opening the fluid passage.

6. The connector assembly of claim 5, wherein the cam features substantially lock the tubular member relative to the inner housing when the inner housing reaches the second position.

7. The connector assembly of claim 6, wherein the cam features provide at least one of a tactile indication and an audible indication when the cam features substantially lock to provide an indication to a user that the fluid passage has been opened.

8. The connector assembly of claim 5, wherein the tubular member comprises one or more visual indicators that are exposed when the tubular member moves distally relative to the inner housing as the inner housing reaches the second position to provide a visual indication to a user that the fluid passage has been opened.

9. The assembly of claim 1, wherein the cam mechanism comprises cam features on the outer shell and tubular member for causing the tubular member to rotate as the inner housing moves between the first and second positions.

10. The connector assembly of claim 1, wherein the inner housing is biased to the first position, thereby biasing the tubular member to close the fluid path.

11. The assembly of claim 9, wherein the outer shell comprises a bezel and a backing member, and wherein the cam features comprise one or more cam elements on the backing member that interact with one or more mating cam features on the tubular member.

12. The assembly of claim 11, further comprising a syringe having a barrel with a proximal end and a distal end and a plunger extending into the proximal end of the barrel, the distal end of the barrel including the backing member.

13. The connector assembly of claim 10, wherein the inner housing is biased to the first position by an elastic member.

14. The connector assembly of claim 9, wherein the inner housing comprises a deformable membrane substantially closing the boss, and the tubular member comprises a fluid cap coupled to the deformable membrane to open one or more gaps between the deformable membrane and the fluid cap when the tubular member is rotated between the first and second positions.

15. The connector assembly of claim 9, wherein the inner housing comprises one or more openings, and wherein the tubular member comprises one or more openings, wherein the one or more openings in the inner housing are offset from the one or more openings in the tubular member in the first position, and wherein the one or more openings in the inner housing are aligned from the one or more openings in the tubular member in the second position, thereby allowing fluid flow through the one or more openings.

* * * * *